(12) United States Patent
Nishi et al.

(10) Patent No.: US 11,318,212 B2
(45) Date of Patent: May 3, 2022

(54) METHOD FOR PRODUCING ANTIBODY-DRUG CONJUGATE

(71) Applicant: DAIICHI SANKYO COMPANY, LIMITED, Tokyo (JP)

(72) Inventors: Yoshio Nishi, Tokyo (JP); Kohei Sakanishi, Tokyo (JP); Shigeru Noguchi, Tokyo (JP); Tadahiro Takeda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 134 days.

(21) Appl. No.: 16/642,277

(22) PCT Filed: Aug. 30, 2018

(86) PCT No.: PCT/JP2018/032055
§ 371 (c)(1),
(2) Date: Feb. 26, 2020

(87) PCT Pub. No.: WO2019/044946
PCT Pub. Date: Mar. 7, 2019

(65) Prior Publication Data
US 2020/0384121 A1     Dec. 10, 2020

(30) Foreign Application Priority Data
Aug. 31, 2017   (JP) .............................. JP2017-167690

(51) Int. Cl.
*A61K 47/68*     (2017.01)
*C07C 231/12*    (2006.01)
(Continued)

(52) U.S. Cl.
CPC ...... *A61K 47/6889* (2017.08); *A61K 47/6803* (2017.08); *C07C 231/12* (2013.01);
(Continued)

(58) Field of Classification Search
None
See application file for complete search history.

(56) References Cited

U.S. PATENT DOCUMENTS 5,480,968 A    1/1996  Kraus et al.
5,637,770 A    6/1997  Terasawa et al.
(Continued)

FOREIGN PATENT DOCUMENTS

CA    2927832 A1    11/2011
CA    2815154 A1    2/2012
(Continued)

OTHER PUBLICATIONS

Greene et al., Protective Group in Organic Synthesis Third Edition, John Willey & Sons, Inc, 1999, pp. 552-555 (Year: 1999).*
(Continued)

*Primary Examiner* — Karl J Puttlitz
(74) *Attorney, Agent, or Firm* — Foley & Lardner LLP

(57) ABSTRACT

A method for producing a compound represented by formula (C) wherein $R^1$ represents an amino group protected with a protecting group, the method comprising a step of subjecting a compound represented by formula (B) wherein $R^1$ represents the same meaning as above, to intramolecular cyclization to convert the compound into the compound represented by formula (C).

(Continued)

SEQ ID NO: 1 - Amino acid sequence of a heavy chain of the anti-HER2 antibody

EVQLVESGGGLVQPGGSLRLSCAASGFNIKDTYIHWVR
QAPGKGLEWVARIYPTNGYTRYADSVKGRFTISADTSK
NTAYLQMNSLRAEDTAVYYCSRWGGDGFYAMDYWGQGT
LVTVSSASTKGPSVFPLAPSSKSTSGGTAALGCLVKDY
FPEPVTVSWNSGALTSGVHTFPAVLQSSGLYSLSSVVT
VPSSSLGTQTYICNVNHKPSNTKVDKKVEPKSCDKTHT
CPPCPAPELLGGPSVFLFPPKPKDTLMISRTPEVTCVV
VDVSHEDPEVKFNWYVDGVEVHNAKTKPREEQYNSTYR
VVSVLTVLHQDWLNGKEYKCKVSNKALPAPIEKTISKA
KGQPREPQVYTLPPSREEMTKNQVSLTCLVKGFYPSDI
AVEWESNGQPENNYKTTPPVLDSDGSFFLYSKLTVDKS
RWQQGNVFSCSVMHEALHNHYTQKSLSLSPGK

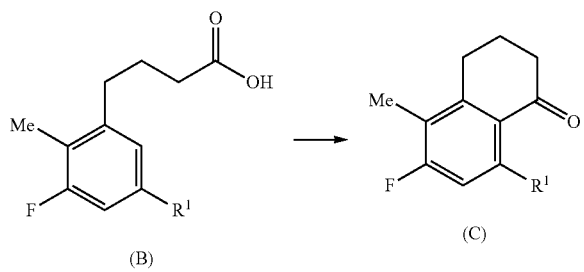

65 Claims, 5 Drawing Sheets

Specification includes a Sequence Listing.

(51) Int. Cl.
| | | |
|---|---|---|
| C07C 233/15 | (2006.01) | |
| C07C 233/33 | (2006.01) | |
| C07C 233/54 | (2006.01) | |
| C07D 491/22 | (2006.01) | |
| C07K 5/103 | (2006.01) | |
| C07K 16/00 | (2006.01) | |
| C07K 16/28 | (2006.01) | |
| C07K 16/30 | (2006.01) | |
| C07K 16/32 | (2006.01) | |

(52) U.S. Cl.
CPC .......... *C07C 233/15* (2013.01); *C07C 233/33* (2013.01); *C07C 233/54* (2013.01); *C07D 491/22* (2013.01); *C07K 5/1008* (2013.01); *C07K 16/00* (2013.01); *C07K 16/28* (2013.01); *C07K 16/2827* (2013.01); *C07K 16/30* (2013.01); *C07K 16/32* (2013.01)

(56) References Cited

U.S. PATENT DOCUMENTS

| | | | |
|---|---|---|---|
| 5,677,171 | A | 10/1997 | Hudziak et al. |
| 5,821,337 | A | 10/1998 | Carter et al. |
| 5,834,476 | A | 11/1998 | Terasawa et al. |
| 5,837,673 | A | 11/1998 | Tsujihara et al. |
| 5,849,945 | A | 12/1998 | Kamihara et al. |
| 5,892,043 | A | 4/1999 | Tsujihara et al. |
| 5,968,511 | A | 10/1999 | Akita et al. |
| 6,071,719 | A | 6/2000 | Halsey et al. |
| 6,096,868 | A | 8/2000 | Halsey et al. |
| 6,156,761 | A | 12/2000 | Bryant et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,041,818 | B2 | 5/2006 | Susaki et al. |
| 7,449,184 | B2 | 11/2008 | Allison et al. |
| 7,585,491 | B2 | 9/2009 | Govindan |
| 7,833,979 | B2 | 11/2010 | Sullivan et al. |
| 7,837,980 | B2 | 11/2010 | Alley et al. |
| 7,999,083 | B2 | 8/2011 | Govindan et al. |
| 8,226,945 | B2 | 7/2012 | Ebens et al. |
| 8,268,319 | B2 | 9/2012 | Govindan |
| 8,394,607 | B2 | 3/2013 | Ebens et al. |
| 8,425,912 | B2 | 4/2013 | Govindan |
| 8,524,865 | B2 | 9/2013 | Ebens et al. |
| 8,741,291 | B2 | 6/2014 | Bhat et al. |
| 8,802,820 | B2 | 8/2014 | Chamberlain et al. |
| 8,907,071 | B2 | 12/2014 | Sullivan et al. |
| 8,968,741 | B2 | 3/2015 | Ebens et al. |
| 9,808,537 | B2 | 11/2017 | Masuda et al. |
| 9,850,312 | B2 | 12/2017 | Agatsuma et al. |
| 9,872,924 | B2 | 1/2018 | Naito et al. |
| 10,195,288 | B2 | 2/2019 | Masuda et al. |
| 10,227,417 | B2 | 3/2019 | Agatsuma et al. |
| 10,383,878 | B2 | 8/2019 | Hettmann et al. |
| 2001/0034446 | A1 | 10/2001 | Kaminhara et al. |
| 2003/0018989 | A1 | 1/2003 | Brennan et al. |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0228007 | A1 | 10/2005 | Jagtap et al. |
| 2005/0271671 | A1 | 12/2005 | Griffiths |
| 2005/0276812 | A1 | 12/2005 | Ebens, Jr. et al. |
| 2006/0018899 | A1 | 1/2006 | Kao et al. |
| 2006/0134109 | A1 | 6/2006 | Gaitanaris et al. |
| 2006/0193865 | A1 | 8/2006 | Govindan |
| 2007/0071764 | A1 | 3/2007 | Sullivan et al. |
| 2008/0050310 | A1 | 2/2008 | Ebens et al. |
| 2008/0131363 | A1 | 6/2008 | Govindan et al. |
| 2008/0161245 | A1 | 7/2008 | Kratz et al. |
| 2008/0260744 | A1 | 10/2008 | Gaitanaris et al. |
| 2008/0305044 | A1 | 12/2008 | McDonagh et al. |
| 2009/0178153 | A1 | 7/2009 | Gaitanaris et al. |
| 2009/0274713 | A1 | 11/2009 | Chari et al. |
| 2009/0286258 | A1 | 11/2009 | Kaur et al. |
| 2009/0291093 | A1 | 11/2009 | Govindan |
| 2010/0068181 | A1 | 3/2010 | Paliwal et al. |
| 2010/0120816 | A1 | 5/2010 | Fontana et al. |
| 2010/0303802 | A1 | 12/2010 | Zoffmann Jensen et al. |
| 2011/0045587 | A1 | 2/2011 | Sullivan et al. |
| 2011/0059076 | A1 | 3/2011 | McDonagh et al. |
| 2011/0070248 | A1 | 3/2011 | Ichikawa et al. |
| 2011/0185439 | A1 | 7/2011 | Gaitanaris et al. |
| 2011/0229406 | A1 | 9/2011 | Hettmann et al. |
| 2011/0293513 | A1 | 12/2011 | Govindan et al. |
| 2012/0121615 | A1 | 5/2012 | Flygare et al. |
| 2012/0171201 | A1 | 7/2012 | Sapra |
| 2012/0201809 | A1 | 8/2012 | Bhat et al. |
| 2012/0302562 | A1 | 11/2012 | Barbosa et al. |
| 2012/0328634 | A1 | 12/2012 | Govindan |
| 2013/0089872 | A1 | 4/2013 | Nakamura et al. |
| 2013/0123178 | A1 | 5/2013 | Dimarchi et al. |
| 2013/0216561 | A1 | 8/2013 | Govindan |
| 2013/0247233 | A1 | 9/2013 | Gaitanaris et al. |
| 2014/0004078 | A1 | 1/2014 | Govindan |
| 2015/0297748 | A1 | 10/2015 | Masuda et al. |
| 2015/0352224 | A1 | 12/2015 | Naito et al. |
| 2016/0219845 | A1 | 8/2016 | Gaitanaris et al. |
| 2016/0279259 | A1 | 9/2016 | Masuda et al. |
| 2016/0282365 | A1 | 9/2016 | Gaitanaris et al. |
| 2016/0287722 | A1 | 10/2016 | Govindan |
| 2016/0297890 | A1 | 10/2016 | Agatsuma et al. |
| 2016/0333112 | A1 | 11/2016 | Naito et al. |
| 2017/0021031 | A1 | 1/2017 | Hettmann et al. |
| 2017/0035906 | A1 | 2/2017 | Naito et al. |
| 2017/0188555 | A1 | 7/2017 | Gaitanaris et al. |
| 2019/0151328 | A1 | 5/2019 | Hettmann et al. |

FOREIGN PATENT DOCUMENTS

| | | |
|---|---|---|
| CA | 2859255 A1 | 6/2013 |
| CN | 1227499 A | 9/1999 |
| CN | 1764478 A | 4/2006 |
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | H03-279343 A | 12/1991 |
| JP | H05-59061 A | 3/1993 |
| JP | H06-87746 A | 3/1994 |
| JP | H08-337584 A | 12/1996 |
| JP | H10-095802 A | 4/1998 |

(56) References Cited

FOREIGN PATENT DOCUMENTS

| | | |
|---|---|---|
| JP | H11-71280 A | 3/1999 |
| JP | H11-092405 A | 4/1999 |
| JP | 2002-060351 A | 2/2002 |
| JP | 2002-527420 A | 8/2002 |
| JP | 2004-189620 A | 7/2004 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-155273 A | 7/2009 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-534535 A | 9/2012 |
| JP | 2013-500253 A | 1/2013 |
| JP | 2013-534906 A | 9/2013 |
| JP | 2017-503784 A | 2/2017 |
| KR | 1020010052385 A | 6/2001 |
| KR | 1020110044808 A | 4/2011 |
| RU | 2404810 C2 | 7/2008 |
| RU | 2450008 C2 | 5/2012 |
| TW | 1232930 A | 5/2005 |
| TW | 20081/434 A | 4/2008 |
| WO | WO-96/26181 A1 | 8/1996 |
| WO | WO-97/46260 A1 | 12/1997 |
| WO | WO-99/46296 A1 | 9/1999 |
| WO | 0021928 * | 4/2000 |
| WO | WO-00/25825 A1 | 5/2000 |
| WO | WO-01/00244 A2 | 1/2001 |
| WO | WO-02/00734 A1 | 1/2002 |
| WO | WO-03/013602 A1 | 2/2003 |
| WO | WO-03/015826 A1 | 2/2003 |
| WO | WO-03/043583 A2 | 5/2003 |
| WO | WO-03/074566 A2 | 9/2003 |
| WO | WO-2004/040000 A2 | 5/2004 |
| WO | WO-2005/040825 A2 | 5/2005 |
| WO | WO-2005/112919 A2 | 12/2005 |
| WO | WO-2006/065533 A1 | 6/2006 |
| WO | WO-2006/092230 A2 | 9/2006 |
| WO | WO-2007/077028 A2 | 7/2007 |
| WO | WO-2008/100624 A2 | 8/2008 |
| WO | WO-2008/116219 A2 | 9/2008 |
| WO | WO-2008/144891 A1 | 12/2008 |
| WO | WO-2011/011474 A1 | 1/2011 |
| WO | WO-2011/021397 A1 | 2/2011 |
| WO | WO-201 1/068845 A1 | 6/2011 |
| WO | WO-201 1/145744 A1 | 11/2011 |
| WO | WO-201 1/155579 A1 | 12/2011 |
| WO | WO-201 2/019024 A2 | 2/2012 |
| WO | WO-201 2/064733 A2 | 5/2012 |
| WO | WO-201 3/068946 A2 | 5/2013 |
| WO | WO-201 3/077458 A1 | 5/2013 |
| WO | WO-201 3/163229 A1 | 10/2013 |
| WO | WO-201 3/188740 A1 | 12/2013 |
| WO | WO-2014/057687 A1 | 4/2014 |
| WO | WO-2014/061277 A1 | 4/2014 |
| WO | WO-201 4/107024 A1 | 7/2014 |
| WO | WO-201 5/098099 A1 | 7/2015 |
| WO | WO-201 5/115091 A1 | 8/2015 |
| WO | WO-201 5/142675 A2 | 9/2015 |
| WO | WO-201 5/146132 A1 | 10/2015 |
| WO | WO-2015/155976 A1 | 10/2015 |
| WO | WO-2015/155998 A1 | 10/2015 |
| WO | WO-2018/135501 A1 | 7/2018 |

OTHER PUBLICATIONS

Database Registry, Chemical Abstracts Service, Columbus, Ohio, US; Registry No. 1936451-40-9, 2016, 3-fluoro-5-iodo-4-methyl aniline (Year: 2016).*

Acchione et al., Impact of linker and conjugation chemistry on antigen binding, Fc receptor binding and thermal stability of model antibody-drug conjugates, mAbs, 2012, pp. 362-372—(12 pages).

Adams et al., "Humanization of a recombinant monoclonal antibody to produce a therapeutic HER dimerization inhibitor, pertuzumab," Cancer Immunol. Immunother. 55:717-727 (2006).

Alimandi et al., "Cooperative signaling of ErbB3 and ErbB2 in neoplastic transformation and human mammary carcinomas," Oncogene 10:1813-1821 (1995)—9 Pages.

Allander et al., "Gastrointestinal Stromal Tumors with KIT Mutations Exhibit a Remarkably Homogeneous Gene Expression Profile," Cancer Research, vol. 61, pp. 8624-8628, Dec. 15, 2001.

Allowance dated Jul. 4, 2017, in Japanese Patent Application No. 2016-117096.

Allowance issued in connection with Taiwanese Patent Application No. 104103127,dated Apr. 11, 2018.

Australian Intellectual Property Office, "Examination Report No. 2 for Standard Patent Application," Australian Patent Application No. 2014371934, dated Sep. 13, 2019.

Barginear et al., "Trastuzumab-DM1: A Review of the Novel Immuno-Conjugate for HER2-Overexpressing Breast Cancer," The Open Breast Cancer Journal 1:25-30 (2009).

Barok et al., "Trastuzumab-DM1 is highly effective in preclinical models of HER2-positive gastric cancer", Cancer Letters, 2011, vol. 306, No. 2, pp. 171-179.

Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3)737-744 (Mar. 1996).

Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).

Bauer et al., "Emerging Agents for the Treatment of Advanced, Imatinib-Resistant Gastrointestinal Stromal Tumors: Current Status and Future Directions," Drugs, vol. 75, 2015, pp. 1323-1334.

Beck, Alain, "The Next Generation of Antibody-drug Conjugates Comes of Age," Discovery Medicine 10(53):329-339 (Oct. 16, 2010)—8 Pages.

Behrens et al., "Methods for site-specific drug conjugation to antibodies," mAbs, vol. 6, No. 1, 2014, pp. 46-53.

Blok et al., "Cytoplasmic Overexpression of HER2: a Key Factor in Colorectal Cancer", Clinical Insights: Oncology, vol. 7, 2013 pp. 41-51.

Bouchard et al., "Antibody-drug conjugates—A new wave of cancer drugs," Bioorganic & Medicinal Chemistry Letters, vol. 24, 2014, pp. 5357-5363.

Burke, Patrick J et al.; "Design, Synthesis, and Biological Evaluation of Antibody—Drug Conjugates Comprised of Potent Campothetchin Analogues"; Bioconjugate Chemistry; Jun. 17, 2009; vol. 20, No. 6; pp. 1242-1250.

Calabrese et al., "Assignment of TACSTD1 (alias TROP 1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).

Canadian Examiner's Interview Summary issued in Canadian Patent Application No. 2885800 dated Mar. 28, 2017.

Canadian Office Action dated Apr. 13, 2018 in corresponding application No. 2939802.

Chi et al., "ETV1 is a lineage survival factor that cooperates with KIT in gastrointestinal stromal tumours," Nature, vol. 467, Oct. 14, 2010, pp. 849-855.

Chinese Office Action dated Nov. 8, 2019 for corresponding Application No. 201580019138.9—4 pages.

Chinese Office Action issued to corresponding App. No. 201480071134. 0—dated Aug. 20, 2019 (5 pages).

Chinese Search Report dated Jun. 24, 2020 for corresponding Application No. 108114649.

Colombian Reconsideration Petition dated Mar. 15, 2018 in corresponding application No. NC2016/0000187—36 pages.

Corless et al., "Gastrointestinal stromal tumours: origin and molecular oncology," Nature Reviews, Cancer, vol. 11, Dec. 2011, pp. 865-878.

(56) References Cited

OTHER PUBLICATIONS

Coussens et al., "Tyrosine Kinase Receptor with Extensive Homology to EGF Receptor Shares Chromosomal Location with neu Oncogene," Science 230(4730): 1132-1139 (Dec. 1985).
D. Loo et al.: "Development of an Fc-Enhanced Anti-B7-H3 Monoclonal Antibody with Potent Antitumor Activity", Clinical Cancer Research, vol. 18, No. 14, Jul. 15, 2012 (Jul. 15, 2012), pp. 3834-3845, XP055092714, ISSN: 1078-0432, DOI: 10.1158/1078-0432.CCR-12-0715.
Defazio et al., "Expression of c-erbB Receptors, Heregulin and Oestrogen Receptor in Human Breast Cell Lines," Int. J. Cancer 87:487-498 (2000)—12 Pages.
Demetri et al., "NCCN Task Force Report: Update on the Management of Patients with Gastrointestinal Stromal Tumors," Journal of the National Comprehensive Cancer Network, vol. 8, Supplement 2, Apr. 2010, pp. S-1-S-41.
Di Fiore et al., "erbB-2 Is a Potent Oncogene When Overexpressed in NIH/3T3 Cells," Science 237:178-182 (Jul. 1987).
Donaghy, Heather, "Effects of antibody, drug and linker on the preclinical and clinical toxicities of antibody-drug conjugates," mAbs, vol. 8, No. 4, 2016, pp. 659-671.
Dosio et al., "Antibody-targeted leucinostatin A", Journal of Controlled Release, No. 32, (1994), pp. 37-44.
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
English-language translation of International Search report issued in International Patent Application No. PCT/JP2015/002020 dated Jul. 20, 2015—Pages.
Esteva et al., "A Phase II Study of Intravenous Exatecan Mesylate (DX-8951f) Administered Daily for 5 Days Every 3 Weeks to Patients with Metastatic Breast Carcinoma", American Cancer Society,2003,900-907.
European Search Report in corresponding application No. 15776810.2 dated Aug. 11, 2017.
European Search Report issued in corresponding application No. 15743738.5 dated Aug. 9, 2017.
Extended European Search Report dated Feb. 4, 2020 for corresponding Application No. 19206764.3.
Extended European Search Report dated May 10, 2017 in European Patent Application No. 14874745.4.
Extended European Search Report dated May 13, 2016, in European Patent Application No. 13847461.4.
Extended European Search Report dated May 6, 2016, in European Patent Application No. 13845596.9.
Extended European Search Report dated Nov. 30, 2020 for corresponding European Patent Application No. 18742022.9.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 dated Nov. 13, 2017.
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011,54(12):4077-4091, abstract.

Graus-Porta et al., "ERbB-2, the preferred heterodimerization partner or all ErbB receptors, is a mediator of lateral signaling," EMBO J. 16(7): 1647-1655 (1997).
Gravalos et al., "HER2 in gastric cancer: a new prognostic factor and a novel therapeutic target," Ann. Oncol. 19:1523-1529 (2008).
Haasen Dorothea et al: "G protein-coupled receptor internalization assays in the high-content screening format", Biomembranes: Transport Theory': Cells and Model Membranes; [Methods in Enzymology, ISSN 0076-6879], Elsevier, Academic Press, NL, vol. 414, Jan. 1, 2006 (Jan. 1, 2006), pp. 121-139.
Hardwick et al., "Immunohistochemical detection of p53 and c-erbB-2 in oesophageal carcinoma; no correlation with prognosis," Eur. J. Surg. Oncol. 23:30-35 (1997).
Hinrichs et al., "Antibody Drug Conjugates: Nonclinical Safety Considerations," the AAPS Journal, vol. 17, No. 5, Sep. 2015, pp. 1055-1064.
Hirata T: "Producing monoclonal antibody of extracellular domain of metabotropic glutamate receptor 1, by hybridizing spleen cell of non-human animal immunized by olfactory tract, with myeloma cell, culturing hybridoma, screening culture supernatant", WPI/THOMSON,, vol. 2004, No. 36, Apr. 22, 2004 (Apr. 22, 2004).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
In Office Action issued in the corresponding Indian Patent Application Ser. No. 201647013640, dated Jul. 19, 2019.
International Search Report and Written Opinion for correspondence Application No. PCT/JP2018/007152 dated Apr. 24, 2018.
International Search Report for corresponding Application No. PCT/JP2014/006421 dated Mar. 17, 2015.
International Search Report for PCT/JP2013/006069, dated Dec. 17, 2013.
International Search Report for PCT/JP2013/006178, dated Dec. 17, 2013.
International Search Report issued in International Patent Application No. PCT/JP2015/000355 dated Apr. 21, 2015.
International Searching Authority, "International Search Report," issued in connection with International Patent Application No. PCT/JP2018/001065, dated Apr. 17, 2018.
International Searching Authority, "Written Opinion," issued in connection with International Patent Application No. PCT/JP2018/001065, dated Apr. 17, 2018.
Japanese Notice Of Allowance dated Oct. 18, 2016 in corresponding application No. 2016-166850.
Japanese Office Action dated Dec. 6, 2016 in corresponding application No. 2016-540705.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997)—7 Pages.
K. Yonesaka, et al., "Anti-HER3 monoclonal antibody patritumab sensitizes refractory non-small cell lung cancer to the epidermal growth factor receptor inhibitor erlotinib",Oncogene vol. 35, pp. 878-886, 2016 (10 pages.
Kamath et al., "Challenges and advances in the assessment of the disposition of antibody-drug conjugates," Biopharmaceutics & Drug Disposition, 2015, 9 pages.
Kang et al, "Engineering multivalent antibodies to target heregulin-induced HER3 signaling in breast cancer cells, mAbs", Mar./Apr. 2014, vol. 6, No. 2, pp. 340-353.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).

(56) References Cited

OTHER PUBLICATIONS

Kawakami et al—"The anti-HER3 antibody patritumab abrogates cetuximab resistance mediated by heregulin in colorectal cancer cells", Oncotarget, vol. 5, No. 23, Dec.-May 2014, 11847-11856—10 pages.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
Korean Office Action dated May 1, 2018 in corresponding application No. 10-2016-7015961.
Korkaya et al., "HER2 regulates the mammary stem/progenitor cell population driving tumorigenesis and invasion," Oncogene 27:6120-6130 (2008).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "Potent and broad antitumor effects of DX-8951f, a water-soluble camptothecin derivative, against various human tumors xenografted in nude mice," Cancer Chemother. Pharmacol. 42:210-220 (1998)—11 Pages.
Linnenbach et al., "Sequence investigation of the major gastrointestinal tumor-associatea antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
Martin et al., "Constitutive Activity among Orphan Class-A G Protein Coupled Receptors," PLOS One, Sep. 18, 2015, pp. 1-12.
Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.
McDonagh et al., "Engineered antibody-drug conjugates with defined sites and stoichiometries of drug attachment," Protein Engineering, Design & Selection, 2006, 19(7):299-307.
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995)—7 Pages.
Moghaddas et al., "Whether HER2-positive non-breast cancers are candidates for treatment with Ado-trastuzumab emtansine?", J. Res Parm Pract, vol. 5(4), 2016 pp. 227-233.
Momoko Hase et al.: Characterization of an Orphan G Protein-coupled Receptor, GPR20, That Constitutively Activates G i Proteins:, Journal of Biological Chemistry, vol. 283, No. 19, May 9, 2008 (May 9, 2008), p. 12747-12755.
Mühlmann et al., "TROP2 expression as prognostic marker for gastric carcinoma," J. Clin. Pathol. 62(2): 152-158 (2009).
N.V. Sergina, et al. "Escape from HER-family tyrosine kinase inhibitor therapy by the kinase-inactive HER3", Nature, vol. 445, pp. 437-441, 2007 (6 pages).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medical Chemistry Letters 26(6):1542-1545 (2016)—4 Pages.
Ning et al., "TROP2 expression and its correlation with tumor proliferation and angiogenesis in human gliomas," Neurol. Sci. 34(10):1745-1750 (2013).
Non-Final Office Action dated Apr. 5, 2019 in U.S. Appl. No. 15/821,697.
Non-Final Office Action issued in U.S. Appl. No. 14/435,114 dated Jul. 21, 2016.
Non-Final Office Action issued in U.S. Appl. No. 14/436,458 dated Jul. 19, 2016.
Non-Final Office Action issued in U.S. Appl. No. 15/180,203 dated Jul. 25, 2016.
Non-Final Office Action issued in U.S. Appl. No. 15/221,851 dated Jul. 17, 2017.
Non-Final Office Action issued in U.S. Appl. No. 15/821,662 dated Jan. 17, 2018.
Notice of Allowance dated Aug. 25, 2017 for corresponding U.S. Appl. No. 15/187,179.
Notice of Allowance dated May 18, 2017 for corresponding U.S. Appl. No. 15/187,179.
Notice of Allowance dated Nov. 2, 2018 for corresponding U.S. Appl. No. 15/821,662.
Notice of Allowance issued in U.S. Appl. No. 15/221,851 dated Jun. 13, 2018.
O'Dowd et al., "Cloning and chromosomal mapping of four putative novel human G-protein-coupled receptor genes," Gene. vol. 187, 1997, pp. 75-81.
Ochi et al., "A possible mechanism for the long-lasting antitumor effect of the macromolecular conjugate DE-310: mediation by cellular uptake and drug release of its active camptothecin analog DX-8951," Cancer Chemotherapy and Pharmacology 55(4): 323-332 (2004).
Office Action dated Nov. 21, 2017 in corresponding application No. PCT/JP2017/036215.
Office Action dated Apr. 22, 2016, in Singapore Patent Application No. 11201502887W.
Office Action issued in Chinese Patent Application No. 201380053256.2 dated Nov. 1, 2016.
Office Action issued in Colombian Application No. NC2016/0000187 dated May 9, 2017. An English translation is provided.
Office Action issued in U.S. Appl. No. 15/187,179 dated Oct. 21, 2016.
Office Action with Search Report dated Aug. 29, 2017, in RU 2015113767.
Ogitani et al., "Wide application of a novel topoisomerase I inhibitor-based drug conjugation technology," Bioorganic & Medicinal Chemistry Letters, vol. 26, 2016, 5069-5072.
Oguma et al., "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry", Biomedical Chromatography, 2005, vol. 19, No. 1, pp. 19-26—(8 pages).
Ohmachi et al., "Clinical Significance of TROP2 Expression in Colorectal Cancer," Res. 12(10):3057-3063 (May 15, 2006).
Opposition dated May 3, 2017, against corresponding Colombian Patent Application No. NC2016/0000187.
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, p. S2290, abstract No. P3.04-013, Nov. 2017 (3 pages).
Perez et al., "Antibody-drug conjugates: current status and future directions," Drug Discovery Today, vol. 19, No. 7, Jul. 2014, pp. 869-881.
Peters et al., "Antibody-drug conjugates as novel anti-cancer chemotherapeutics," Bioscience Reports, vol. 35, 2015, pp. 1-20.
Plowman et al., "Molecular cloning and expression of an additional epidermal growth factor receptor-related gene," Proc. Natl. Acad. Sci. USA 87:4905-4909 (Jul. 1990)—5 Pages.
Polakis, Paul, "Antibody Drug Conjugates for Cancer Therapy," Pharmacological Reviews, vol. 68, pp. 3-19, Jan. 2016.
Ripani et al., "Human Trop-2 is a Tumor-Associated Calcium Signal Transducer," Int. J. Cancer 76(5):671-676 (1998).
Rowinsky, "Preclinical and Clinical Development of Exatecan(DX-8951f)", Camptothecins in Cancer Therapy, 2005, pp. 317-318 (25 pages).
Russian Office Action dated Mar. 5, 2019 in corresponding application No. 2016143351.

(56) References Cited

OTHER PUBLICATIONS

Russian Office Action dated Oct. 11, 2018 in corresponding application No. 2016123597—13 pages.
Scott et al., "Antibody therapy of cancer," Nature Reviews, vol. 12, Apr. 2012, pp. 278-287.
Shen et al., "Conjugation site modulates the in vivo stability and therapeutic activity of antibody-drug conjugates," Nature Biotechnology, vol. 30, Jan. 22, 2012, pp. 184-189.
Shiose et al, "Systematic Research of Peptide Spacers Controlling Drug Release from Macromolecular Prodrug System, Carboxymethyldextran Polyalcohol-Peptide-Drug Conjugates," Bioconjugate Chem. 20(1):60-70(2009).
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Sievers et al, Antibody-Drug Conjugates in Cancer Therapy, Annual Review of Medicine, 2013, vol. 64, No. 1, pp. 15-29.
Slamon et al., "Human breast cancer: correlation or Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Soepenberg et al., "Phase I and Pharmacokinetic Study of DE-310 in Patients with Advanced Solid Tumors," Clin. Cancer Res. 11:703-711 (Jan. 15, 2005)—9 Pages.
Soepenberg, "Liquid chromatographic assays for DE-310, a novel camptothecin analog, and two major enzymatic products in human matrices," Journal of Chromatography B, 799, 15-22 (2004).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Taiwanese Office Action dated Jul. 30, 2018 in corresponding application No. 104111534.
Taiwanese Office Action issued in Taiwanese Patent Application No. 102136742 dated May 15, 2017.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997)—10 Pages.
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Tsuchikama et al., "Antibody-drug conjugates: recent advances in conjugation and linker chemistries," Protein & Cell, Oct. 14, 2016, 14 pages.
Velez et al., "APOE*E2 allele delays age of onset in PSEN1 E280A Alzheimer's disease," Molecular Psychiatry, 2015, pp. 1-9.
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).

Wente et al., "DE-310, a macromolecular prodrug of the topoisomerase-I-inhibitor exatecan (DX-8951), in patients with operable solid tumors," Investigational New Drugs 23:339-347 (2005)—9 Pages.
Yamaguchi, Teruhide, "Current situations and the future prospect of monoclonal antibody products," Report of the National Institute of Health, vol. 132, 2014, pp. 36-46.
Yano et al., "Comparison of HER2 gene amplification assessed by fluorescence in situ hybridization and HER2 protein expression assessed by immunohistochemistry in gastric cancer," Oncol. Rep. 15:65-71 (2006).
R. De Jager et al., "DX-8951f: summary of phase I clinical trials", Annals New York Academy of Sciences, pp. 260-273.
K. Inoue et al., "CM-Dextran-Polyalcohol-Camptothecin Conjugate", Polymer Drugs in the Clinical Stage, (2003), pp. 145-153.
Kumazawa et al., "DE-310, a novel macromolecular carrier system for the camptothecin analog DX-8951f: Potent antitumor activities in various murine tumor models", Cancer Sci, vol. 95, No. 2 (Feb. 2004), pp. 168-175.
Extended European Search Report dated Apr. 14, 2021 for corresponding European Patent Application No. 18851346.9.
Biggs et al., "Monoquaternary neuromuscular blocking agents based on 1-tetralone and 1-indanone," Journal of Medicinal Chemistry, vol. 19, No. 4, 1976, pp. 472-475.
Sugimori et al., "Synthesis and Antitumor Activity of Ring A- and F-Modified Hexacyclic Camptothecin Analogues," Journal of Medicinal Chemistry, vol. 41, No. 13, 1998, pp. 2308-2318.
Ducry et al., "Antibody—Drug Conjugates: Linking Cytotoxic Payloads to Monoclonal Antibodies," Bioconjugate Chem, vol. 21, 2010, pp. 5-13.
Alley et al., "Antibody-drug conjugates: targeted drug delivery for cancer," Current Opinion in Chemical Biology, vol. 14, 2010, pp. 529-537.
Damle, Nitin K., "Tumour-targeted chemotherapy with immunoconjugates of calicheamicin," Expert Opin. Biol. Ther., vol. 4, No. 9, 2004, pp. 1445-1452.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
International Searching Authority, "International Search Report," issued in connection with International Patent Application No. PCT/JP2018/032055, dated Nov. 13, 2018.
International Searching Authority, "Written Opinion," issued in connection with International Patent Application No. PCT/JP2018/032055, dated Nov. 13, 2018.
Greene et al., "Protective Group in Organic Synthesis Third Edition", John Wiley & Sons, Inc., 1999, pp. 552-555.
Registry (SIN) [online], Jun. 21, 2016, [retrieval date Oct. 17, 2018], CAS registration No. 1936451-40-9.

\* cited by examiner

[Figure 1]

SEQ ID NO: 1 - Amino acid sequence of a heavy chain of the anti-HER2 antibody

EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK

[Figure 2]

SEQ ID NO: 2 - Amino acid sequence of a light chain of the anti-HER2 antibody

DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

[Figure 3]

SEQ ID NO: 3 - Amino acid sequence of a heavy chain of the anti-HER3 antibody

```
QVQLQQWGAGLLKPSETLSLTCAVYGGSFSGYYWSWIR
QPPGKGLEWIGEINHSGSTNYNPSLKSRVTISVETSKN
QFSLKLSSVTAADTAVYYCARDKWTWYFDLWGRGTLVT
VSSASTKGPSVFPLAPSSKSTSGGTAALGCLVKDYFPE
PVTVSWNSGALTSGVHTFPAVLQSSGLYSLSSVVTVPS
SSLGTQTYICNVNHKPSNTKVDKRVEPKSCDKTHTCPP
CPAPELLGGPSVFLFPPKPKDTLMISRTPEVTCVVVDV
SHEDPEVKFNWYVDGVEVHNAKTKPREEQYNSTYRVVS
VLTVLHQDWLNGKEYKCKVSNKALPAPIEKTISKAKGQ
PREPQVYTLPPSREEMTKNQVSLTCLVKGFYPSDIAVE
WESNGQPENNYKTTPPVLDSDGSFFLYSKLTVDKSRWQ
QGNVFSCSVMHEALHNHYTQKSLSLSPGK
```

[Figure 4]

SEQ ID NO: 4 - Amino acid sequence of a light chain of the anti-HER3 antibody

```
DIEMTQSPDSLAVSLGERATINCRSSQSVLYSSSNRNY
LAWYQQNPGQPPKLLIYWASTRESGVPDRFSGSGSGTD
FTLTISSLQAEDVAVYYCQQYYSTPRTFGQGTKVEIKR
TVAAPSVFIFPPSDEQLKSGTASVVCLLNNFYPREAKV
QWKVDNALQSGNSQESVTEQDSKDSTYSLSSTLTLSKA
DYEKHKVYACEVTHQGLSSPVTKSFNRGEC
```

[Figure 5]

SEQ ID NO: 5 - Amino acid sequence of a heavy chain of the anti-TROP2 antibody

```
MKHLWFFLLLVAAPRWVLSQVQLVQSGAEVKKPGASVK
VSCKASGYTFTTAGMQWVRQAPGQGLEWMGWINTHSGV
PKYAEDFKGRVTISADTSTAYLQLSSLKSEDTAVYY
CARSGFGSSYWYFDVWGQGTLVTVSSASTKGPSVFPLA
PSSKSTSGGTAALGCLVKDYFPEPVTVSWNSGALTSGV
HTFPAVLQSSGLYSLSSVVTVPSSSLGTQTYICNVNHK
PSNTKVDKRVEPKSCDKTHTCPPCPAPELLGGPSVFLF
PPKPKDTLMISRTPEVTCVVVDVSHEDPEVKFNWYVDG
VEVHNAKTKPREEQYNSTYRVVSVLTVLHQDWLNGKEY
KCKVSNKALPAPIEKTISKAKGQPREPQVYTLPPSREE
MTKNQVSLTCLVKGFYPSDIAVEWESNGQPENNYKTTP
PVLDSDGSFFLYSKLTVDKSRWQQGNVFSCSVMHEALH
NHYTQKSLSLSPGK
```

Signal sequence (1-19), Variable region (20-140), Constant region (141-470)

[Figure 6]

SEQ ID NO: 6 - Amino acid sequence of a light chain of the anti-TROP2 antibody

```
MVLQTQVFISLLLWISGAYGDIQMTQSPSSLSASVGDR
VTITCKASQDVSTAVAWYQQKPGKAPKLLIYSASYRYT
GVPSRFSGSGSGTDFTLTISSLQPEDFAVYYCQQHYIT
PLTFGQGTKLEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC
```

Signal sequence (1-20), Variable region (21-129), Constant region (130-234)

[Figure 7]

SEQ ID NO: 7 - Amino acid sequence of a heavy chain of the anti-B7-H3 antibody

MKHLWFFLLLVAAPRWVLSQVQLVQSGAEVKKPGSSVK
VSCKASGYTFTNYVMHWVRQAPGQGLEWMGYINPYNDD
VKYNEKFKGRVTITADESTSTAYMELSSLRSEDTAVYY
CARWGYYGSPLYYFDYWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLPGK

Signal sequence (1-19), Variable region (20-141), Constant region (142-471)

[Figure 8]

SEQ ID NO: 8 - Amino acid sequence of a light chain of the anti-B7-H3 antibody

MVLQTQVFISLLLWISGAYGEIVLTQSPATLSLSPGER
ATLSCRASSRLIYMHWYQQKPGQAPRPLIYATSNLASG
IPARFSGSGSGTDFTLTISSLEPEDFAVYYCQQWNSNP
PTFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), Variable region (21-128), Constant region (129-233)

[Figure 9]

SEQ ID NO: 9 - Amino acid sequence of a heavy chain of the anti-GPR20 antibody

MKHLWFFLLLVAAPRWVLSEVQLVQSGAEVKKPGASVK
VSCKASGYTFTSYYISWIRQAPGQGLKYMGFINPGSGH
TNYNEKFKGRVTITADKSSTATMELSSLRSEDTAVYY
CARGAGGFLRIITKFDYWGQGTLVTVSSASTKGPSVFP
LAPSSKSTSGGTAALGCLVKDYFPEPVTVSWNSGALTS
GVHTFPAVLQSSGLYSLSSVVTVPSSSLGTQTYICNVN
HKPSNTKVDKRVEPKSCDKTHTCPPCPAPELLGGPSVF
LFPPKPKDTLMISRTPEVTCVVVDVSHEDPEVKFNWYV
DGVEVHNAKTKPREEQYNSTYRVVSVLTVLHQDWLNGK
EYKCKVSNKALPAPIEKTISKAKGQPREPQVYTLPPSR
EEMTKNQVSLTCLVKGFYPSDIAVEWESNGQPENNYKT
TPPVLDSDGSFFLYSKLTVDKSRWQQGNVFSCSVMHEA
LHNHYTQKSLSLSPGK

Signal sequence (1-19), Variable region (20-142), Constant region (143-472)

[Figure 10]

SEQ ID NO: 10 - Amino acid sequence of a light chain of the anti-GPR20 antibody

MVLQTQVFISLLLWISGAYGDTQLTQSPSSLSASVGDR
VTITCRASKSVSTYIHWYQQKPGKQPKLLIYSAGNLES
GVPSRFSGSGSGTDFTLTISSLQPEDFANYYCQQINEL
PYTFGQGTKVEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), Variable region (21-129), Constant region (130-234)

METHOD FOR PRODUCING ANTIBODY-DRUG CONJUGATE

CROSS-REFERENCE TO RELATED APPLICATIONS

The present application claims priority under 37 U.S.C. § 371 to International Patent Application No. PCT/JP2018/032055, filed Aug. 30, 2018, which claims priority to and the benefit of Japanese Patent Application No. 2017-167690, filed on Aug. 31, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122622-0114 SL.txt and is 31 kb in size.

TECHNICAL FIELD

The present invention relates to a novel method for producing exatecan, which is a component of an antibody-drug conjugate, and a novel method for producing an antibody-drug conjugate wherein the aforementioned method is used.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (Non-Patent Literatures 1 to 5).

As one such antibody-drug conjugate, an antibody-drug conjugate comprising an antibody and exatecan, which is a topoisomerase I inhibitor, as its components is known (Patent Literatures 1 to 8 and Non-Patent Literatures 6 and 7). Since these antibody-drug conjugates exert a particularly superior antitumor effect and safety, they are currently under clinical studies.

The methods described in Patent Literatures 9 to 11 are known as methods for producing exatecan.

CITATION LIST

Patent Literatures

Patent Literature 1: International Publication No. WO 2014/057687
Patent Literature 2: International Publication No. WO 2014/061277
Patent Literature 3: International Publication No. WO 2015/098099
Patent Literature 4: International Publication No. WO 2015/115091
Patent Literature 5: International Publication No. WO 2015/146132
Patent Literature 6: International Publication No. WO 2015/155976
Patent Literature 7: International Publication No. WO 2015/155998
Patent Literature 8: International Publication No. WO 2018/135501
Patent Literature 9: Japanese Patent Laid-Open No. 5-59061
Patent Literature 10: Japanese Patent Laid-Open No. 8-337584
Patent Literature 11: International Publication No. WO 96/26181 Non-Patent Literatures
Non-Patent Literature 1: Ducry, L., et al., Bioconjugate Chem. (2010) 21, 5-13.
Non-Patent Literature 2: Alley, S. C., et al., Current Opinion in Chemical Biology (2010) 14, 529-537.
Non-Patent Literature 3: Damle N. K. Expert Opin. Biol. Ther. (2004) 4, 1445-1452.
Non-Patent Literature 4: Senter P. D., et al., Nature Biotechnology (2012) 30, 631-637.
Non-Patent Literature 5: Howard A. et al., J Clin Oncol 29: 398-405.
Non-Patent Literature 6: Ogitani Y. et al., Clinical Cancer Research (2016) 22(20), 5097-5108.
Non-Patent Literature 7: Ogitani Y. et al., Cancer Science (2016) 107, 1039-1046.

SUMMARY OF INVENTION

Technical Problem

Exatecan is the compound represented by formula (2):

[Chem. 1]

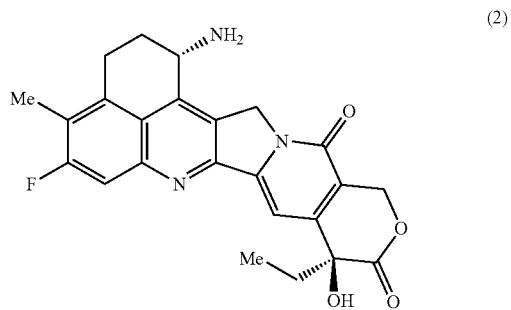

(2)

and is a compound that serves as a component of the antibody-drug conjugate according to the present invention.

The methods described in Patent Literatures 9 to 11 are known as methods for producing exatecan. Such production methods can be described as follows. That is to say, such production methods comprise reacting a compound represented by formula (19) with succinic anhydride to convert the compound into a compound represented by formula (20), reducing the compound to convert the compound into a compound represented by formula (21), converting the compound into a compound represented by formula (22) by an intramolecular cyclization reaction, converting the compound into a compound represented by formula (23) by oximation, converting the compound into a compound represented by formula (24) by Beckmann rearrangement, converting the compound into a compound represented by formula (25) by a ring opening reaction, protecting the amino group to convert the compound into a compound represented by formula (26), hydrolyzing the compound to convert the compound into a compound represented by formula (27), converting the compound into a compound represented by formula (28) by an intramolecular cyclization reaction, converting the compound into a compound represented by formula (29) by reduction, converting the compound into a compound represented by formula (9) by oxidation, then introducing a nitrogen atom to convert the compound into a compound represented by formula (10), converting the compound into a compound represented by formula (11) by selective deprotection, converting the compound into a compound represented by formula (12) by a Friedlander reaction with a compound represented by formula (1), and, finally, deprotecting the acetyl group to produce a compound represented by formula (2), i.e., exatecan. However, in this production method, the ring-opening and ring-closing reactions and the oxidation and reduction reactions have to be repeatedly performed, thus the number of steps is large, and complex operations are required. Accordingly, development of an industrially superior production method is desired.

[Chem. 2]

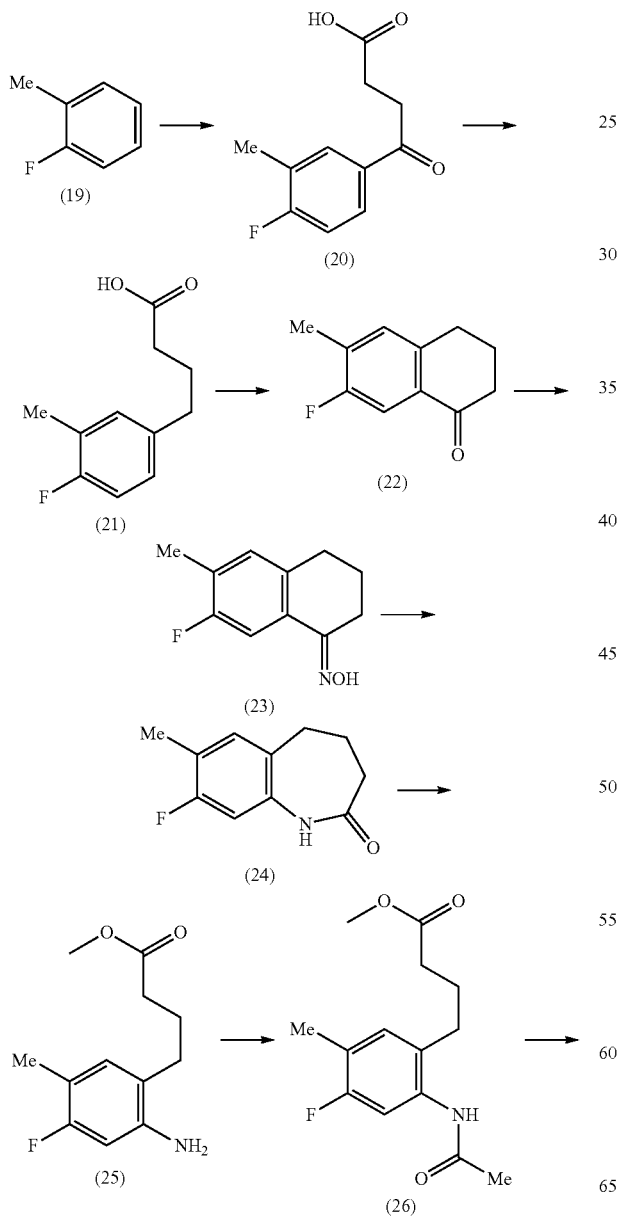

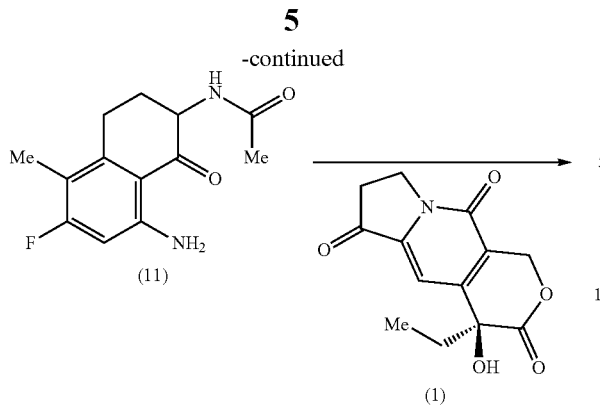

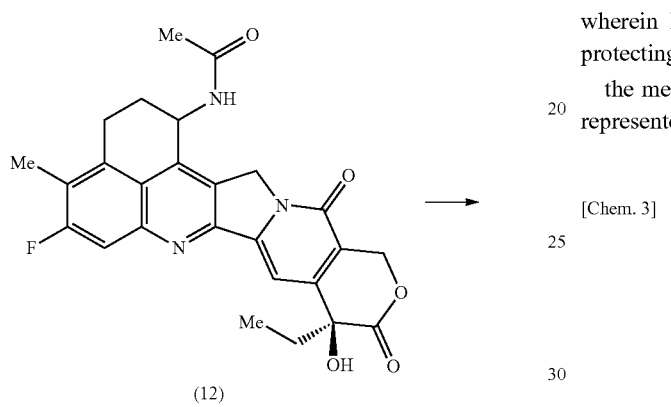

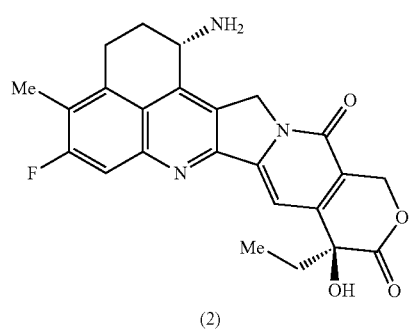

An object of the present invention is to find a novel, industrially superior method for producing exatecan, wherein the number of steps is small. Moreover, another object of the present invention is to develop a novel method for producing an antibody-drug conjugate wherein the aforementioned method is used.

Solution to Problem

As a result of having conducted diligent research on a method for producing exatecan, the present inventors found a novel, industrially superior method for producing exatecan, wherein the number of steps is small. Moreover, the inventors developed a novel method for producing an antibody-drug conjugate wherein exatecan produced by the aforementioned production method is used.

Specifically, the present invention relates to the following.

[1] A method for producing a compound represented by formula (C):

[Chem. 4]

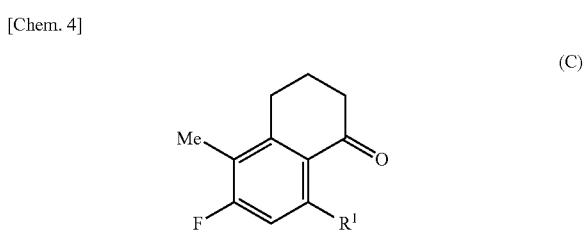

wherein $R^1$ represents an amino group protected with a protecting group, the method comprising a step of subjecting a compound represented by formula (B):

[Chem. 3]

(B)

wherein $R^1$ represents the same meaning as above, to intramolecular cyclization to convert the compound represented by formula (B) into the compound represented by formula (C).

[2] The production method according to [1], wherein $R^1$ is an amino group protected with an acetyl group, a methoxyacetyl group, a trifluoroacetyl group, a trichloroacetyl group, a pivaloyl group, a formyl group, or a benzoyl group.

[3] The production method according to [1], wherein $R^1$ is an amino group protected with an acetyl group or a trifluoroacetyl group.

[4] The production method according to [1], wherein $R^1$ is an amino group protected with an acetyl group.

[5] The production method according to any one of [1] to [4], wherein the intramolecular cyclization is performed by a method comprising reacting the compound represented by formula (B) with trifluoroacetic anhydride.

[6] The production method according to [5], wherein the intramolecular cyclization is performed in a solvent comprising trifluoroacetic acid.

[7] The production method according to any one of [1] to [4], wherein the intramolecular cyclization is performed by a method comprising reacting the compound represented by formula (B) with thionyl chloride.

[8] The production method according to [7], wherein the intramolecular cyclization is performed in the presence of aluminium chloride.

[9] A method for producing a compound represented by formula (C):

[Chem. 6]

(C)

wherein R¹ represents an amino group protected with a protecting group, the method comprising a step of subjecting a compound represented by formula (J):

[Chem. 5]

(J)

wherein Y represents a leaving group, and R¹ represents the same meaning as above, to intramolecular cyclization to convert the compound represented by formula (J) into the compound represented by formula (C).

[10] The production method according to [9], wherein R¹ is an amino group protected with an acetyl group, a methoxyacetyl group, a trifluoroacetyl group, a trichloroacetyl group, a pivaloyl group, a formyl group, or a benzoyl group.

[11] The production method according to [9], wherein R¹ is an amino group protected with an acetyl group or a trifluoroacetyl group.

[12] The production method according to [9], wherein R¹ is an amino group protected with an acetyl group.

[13] The production method according to any one of [9] to [12], wherein Y is a chloro group.

[14] The production method according to any one of [9] to [12], wherein Y is a trifluoroacetoxy group.

[15] The production method according to [13], wherein the intramolecular cyclization is performed in the presence of aluminium chloride.

[16] The production method according to [14], wherein the intramolecular cyclization is performed in a solvent comprising trifluoroacetic acid.

[17] A method for producing a compound represented by formula (C):

[Chem. 10]

(C)

wherein R¹ represents an amino group protected with a protecting group, the method comprising the steps of:
coupling a compound represented by formula (D):

[Chem. 7]

(D)

wherein X represents a leaving group, and R¹ represents the same meaning as above, with 3-butenoic acid to convert the compound represented by formula (D) into a compound represented by formula (E):

[Chem. 8]

(E)

wherein R¹ represents the same meaning as above; then
reducing the compound represented by formula (E) to convert the compound represented by formula (E) into a compound represented by formula (B):

[Chem. 9]

(B)

wherein R¹ represents the same meaning as above; and then
subjecting the compound represented by formula (B) to intramolecular cyclization to convert the compound represented by formula (B) into the compound represented by formula (C).

[18] The production method according to [17], wherein X is a bromo group, an iodo group, a trifluoromethanesulfonyloxy group, or an arylsulfonyloxy group.
[19] The production method according to [17], wherein X is a bromo group.
[20] The production method according to [17], wherein X is an iodo group.
[21] The production method according to any one of [17] to [20], wherein $R^1$ is an amino group protected with an acetyl group, a methoxyacetyl group, a trifluoroacetyl group, a trichloroacetyl group, a pivaloyl group, a formyl group, or a benzoyl group.
[22] The production method according to any one of [7] to [10], wherein $R^1$ is an amino group protected with an acetyl group or a trifluoroacetyl group.
[23] The production method according to any one of [17] to [20], wherein $R^1$ is an amino group protected with an acetyl group.
[24] The production method according to any one of [17] to [23], wherein the step of coupling the compound represented by formula (D) with 3-butenoic acid to convert the compound represented by formula (D) into the compound represented by formula (E) is performed in the presence of a palladium complex prepared from palladium(II) acetate and tri(o-tolyl)phosphine.
[25] The production method according to any one of [17] to [24], comprising the steps of: dissolving the compound represented by formula (E) in a basic aqueous solution to wash the compound represented by formula (E) with a first organic solvent and separating the solvents; and then adding an acid to the basic aqueous solution to extract the compound represented by formula (E) with a second organic solvent and separating the solvents.
[26] The production method according to [25], wherein the first organic solvent is 2-methyltetrahydrofuran.
[27] The production method according to [25] or [26], wherein the second organic solvent is 2-methyltetrahydrofuran.
[28] The production method according to any one of [25] to [27], wherein the basic aqueous solution is an aqueous sodium hydroxide solution.
[29] The production method according to any one of [17] to [28], wherein the step of reducing the compound represented by formula (E) to convert the compound represented by formula (E) into the compound represented by formula (B) is performed by a method comprising reacting the compound represented by formula (E) with hydrogen in a solvent in the presence of a palladium carbon catalyst.
[30] The production method according to any one of [17] to [29], wherein the step of subjecting the compound represented by formula (B) to intramolecular cyclization to convert the compound represented by formula (B) into the compound represented by formula (C) is performed by a method comprising reacting the compound represented by formula (B) with trifluoroacetic anhydride.

[31] The production method according to [30], wherein the intramolecular cyclization is performed in a solvent comprising trifluoroacetic acid.
[32] The production method according to any one of [17] to [29], wherein the step of subjecting the compound represented by formula (B) to intramolecular cyclization to convert the compound represented by formula (B) into the compound represented by formula (C) is performed by a method comprising reacting the compound represented by formula (B) with thionyl chloride.
[33] The production method according to [32], wherein the intramolecular cyclization is performed in the presence of aluminium chloride.
[34] A method for producing a compound represented by formula (2):

[Chem. 16]

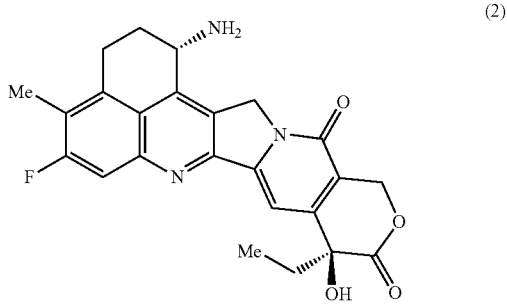

(2)

wherein a compound represented by formula (C):

[Chem. 11]

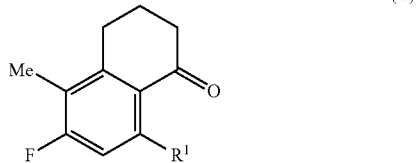

(C)

produced by the method according to any one of [1] to [33] is used as a starting material, the method comprising the steps of:
converting the compound represented by formula (C) into a compound represented by formula (F):

[Chem. 12]

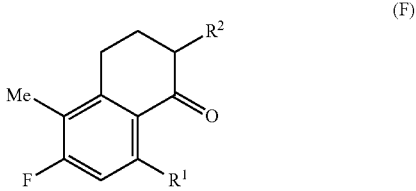

(F)

wherein $R^1$ represents the same meaning as defined in any one of claims 1 to 33, and $R^2$ represents an amino group protected with a protecting group; then converting the compound represented by formula (F) into a compound represented by formula (G):

[Chem. 13]

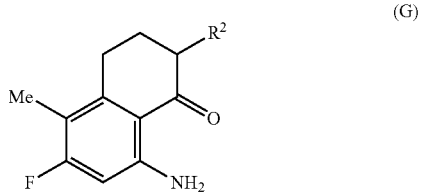

(G)

wherein R² represents the same meaning as above; then
condensing the compound represented by formula (G) with a compound represented by formula (1):

[Chem. 14]

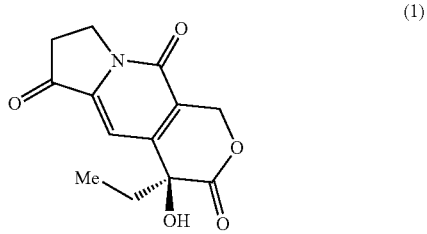

(1)

to convert the compound represented by formula (G) into a compound represented by formula (H):

[Chem. 15]

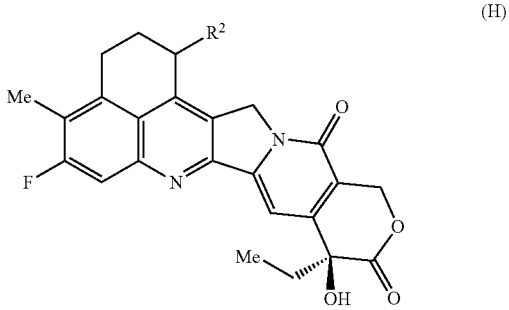

(H)

wherein R² represents the same meaning as above; and then
converting the compound represented by formula (H) into the compound represented by formula (2).

[35] The production method according to [34], wherein R² is an amino group protected with an acetyl group, a methoxyacetyl group, a trifluoroacetyl group, a trichloroacetyl group, a pivaloyl group, a formyl group, or a benzoyl group.

[36] The production method according to [34], wherein R² is an amino group protected with an acetyl group or a trifluoroacetyl group.

[37] The production method according to [34], wherein R² is an amino group protected with an acetyl group.

[38] The production method according to any one of [34] to [37], wherein the step of converting the compound represented by formula (C) into the compound represented by formula (F) comprises the sub-steps of: (i) reacting the compound represented by formula (C) with a nitrous acid ester in the presence of a base to introduce a nitroso group; (ii) introducing a protecting group to a nitrogen atom derived from the nitroso group; and (iii) reducing the compound represented by formula (C) with hydrogen in the presence of a platinum carbon catalyst.

[39] The production method according to any one of claims [34] to [38], wherein the step of converting the compound represented by formula (F) into the compound represented by formula (G) is performed in a solvent comprising hydrochloric acid/ethanol.

[40] The production method according to any one of claims [34] to [39], wherein the step of condensing the compound represented by formula (G) with the compound represented by formula (1) to convert the compound represented by formula (G) into the compound represented by formula (H) is performed in a solvent comprising o-cresol.

[41] The production method according to any one of [34] to [40], wherein the step of converting the compound represented by formula (H) into the compound represented by formula (2) is performed in a solvent comprising methanesulfonic acid.

[42] The production method according to any one of [34] to [41], wherein the compound represented by formula (2) is in the form of a methanesulfonic acid salt.

[43] The production method according to any one of [34] to [41], wherein the compound represented by formula (2) is in the form of a methanesulfonic acid salt m-hydrate wherein m is in a range of 0 to 3.

[44] The production method according to any one of [34] to [41], wherein the compound represented by formula (2) is in the form of a methanesulfonic acid salt anhydrate.

[45] The production method according to any one of [34] to [41], wherein the compound represented by formula (2) is in the form of a methanesulfonic acid salt monohydrate.

[46] The production method according to any one of [34] to [41], wherein the compound represented by formula (2) is in the form of a methanesulfonic acid salt dihydrate.

[47] The production method according to any one of [34] to [41], wherein the compound represented by formula (2) is in the form of a methanesulfonic acid salt trihydrate.

[48] A method for producing a compound represented by formula (2):

[Chem. 28]

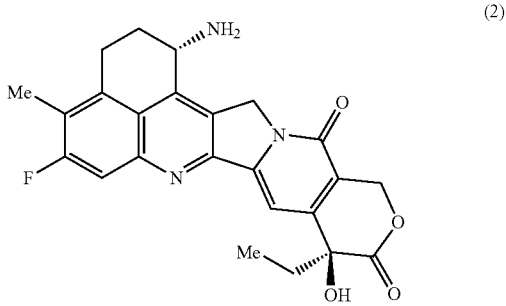

(2)

wherein the method comprises the steps of:
converting a compound represented by formula (3):

[Chem. 17]

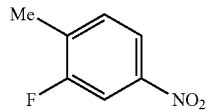
(3)

into a compound represented by formula (4):

[Chem. 18]

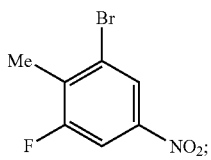
(4)

then
converting the compound represented by formula (4) into a compound represented by formula (5):

[Chem. 19]

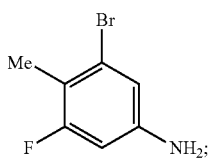
(5)

then
converting the compound represented by formula (5) into a compound represented by formula (6):

[Chem. 20]

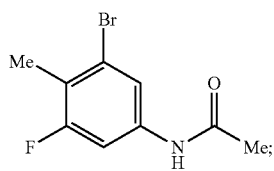
(6)

then
coupling the compound represented by formula (6) with 3-butenoic acid to convert the compound represented by formula (6) into a compound represented by formula (7):

[Chem. 21]

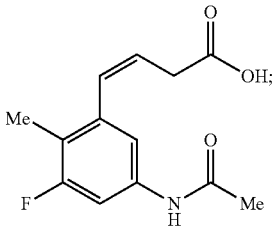
(7)

then
converting the compound represented by formula (7) into a compound represented by formula (8):

[Chem. 22]

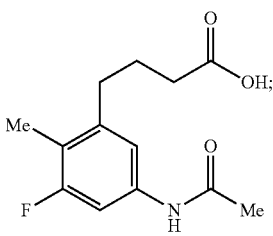
(8)

then
subjecting the compound represented by formula (8) to intramolecular cyclization to convert the compound represented by formula (8) into a compound represented by formula (9):

[Chem. 23]

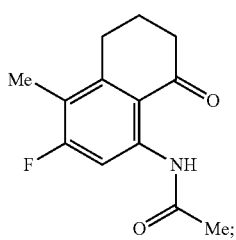
(9)

then
converting the compound represented by formula (9) into a compound represented by formula (10):

[Chem. 24]

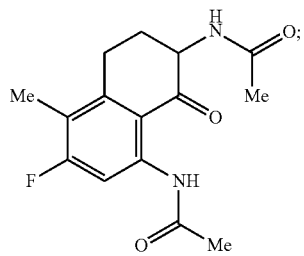
(10)

then
converting the compound represented by formula (10) into a compound represented by formula (11):

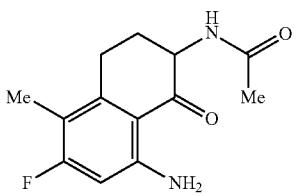

(11)

then condensing the compound represented by formula (11) with a compound represented by formula (1):

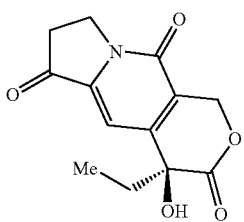

(1)

to convert the compound represented by formula (11) into a compound represented by formula (12):

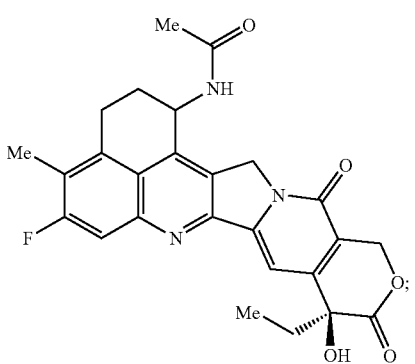

(12)

and then converting the compound represented by formula (12) into the compound represented by formula (2).

[49] The production method according to [48], wherein the step of coupling the compound represented by formula (6) with 3-butenoic acid to convert the compound represented by formula (6) into the compound represented by formula (7) is performed in the presence of a palladium complex prepared from palladium(II) acetate and tri(o-tolyl) phosphine.

[50] The production method according to [48] or [49], comprising the steps of: dissolving the compound represented by formula (7) in a basic aqueous solution to wash the compound represented by formula (7) with a first organic solvent and separating the solvents; and then adding an acid to the basic aqueous solution to extract the compound represented by formula (7) with a second organic solvent and separating the solvents.

[51] The production method according to [50], wherein the first organic solvent is 2-methyltetrahydrofuran.

[52] The production method according to [50] or [51], wherein the second organic solvent is 2-methyltetrahydrofuran.

[53] The production method according to any one of [50] to [52], wherein the basic aqueous solution is an aqueous sodium hydroxide solution.

[54] The production method according to any one of [48] to [53], wherein the step of subjecting the compound represented by formula (8) to intramolecular cyclization to convert the compound represented by formula (8) into the compound represented by formula (9) is performed by a method comprising reacting the compound represented by formula (8) with trifluoroacetic anhydride.

[55] The production method according to [54], wherein the intramolecular cyclization is performed in a solvent comprising trifluoroacetic acid.

[56] The production method according to any one of [48] to [55], wherein the step of converting the compound represented by formula (9) into the compound represented by formula (10) comprises the sub-steps of: (i) reacting the compound represented by formula (9) with a nitrous acid ester in the presence of a base to introduce a nitroso group; then (ii) introducing a protecting group to a nitrogen atom derived from the nitroso group; and (iii) reducing the compound represented by formula (9) with hydrogen in the presence of a platinum carbon catalyst.

[57] The production method according to any one of [48] to [56], wherein the step of converting the compound represented by formula (10) into the compound represented by formula (11) is performed in a solvent comprising hydrochloric acid/ethanol.

[58] The production method according to any one of [48] to [57], wherein the step of condensing the compound represented by formula (11) with the compound represented by formula (1) to convert the compound represented by formula (11) into the compound represented by formula (12) is performed in a solvent comprising o-cresol.

[59] The production method according to any one of [48] to [58], wherein the step of converting the compound represented by formula (12) into the compound represented by formula (2) is performed in a solvent comprising methanesulfonic acid.

[60] The production method according to any one of [48] to [59], wherein the compound represented by formula (2) is in the form of a methanesulfonic acid salt.

[61] The production method according to any one of [48] to [59], wherein the compound represented by formula (2) is in the form of a methanesulfonic acid salt m-hydrate wherein m is in a range of 0 to 3.

[62] The production method according to any one of [48] to [59], wherein the compound represented by formula (2) is in the form of a methanesulfonic acid salt anhydrate.

[63] The production method according to any one of [48] to [59], wherein the compound represented by formula (2) is in the form of a methanesulfonic acid salt monohydrate.

[64] The production method according to any one of [48] to [59], wherein the compound represented by formula (2) is in the form of a methanesulfonic acid salt dihydrate.

[65] The production method according to any one of [48] to [59], wherein the compound represented by formula (2) is in the form of a methanesulfonic acid salt trihydrate.

[66] A method for producing a compound represented by formula (E):

[Chem. 30]

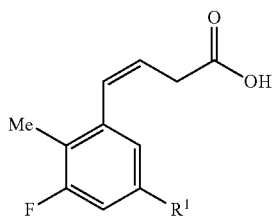

(E)

wherein R¹ represents an amino group protected with a protecting group, the method comprising a step of coupling a compound represented by formula (D):

[Chem. 29]

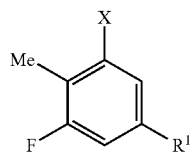

(D)

wherein X represents a leaving group, and R¹ represents the same meaning as above, with 3-butenoic acid to convert the compound represented by formula (D) into the compound represented by formula (E).

[67] The production method according to [66], wherein X is a bromo group, an iodo group, a trifluoromethanesulfonyloxy group, or an arylsulfonyloxy group.

[68] The production method according to [66], wherein X is a bromo group.

[69] The production method according to [66], wherein X is an iodo group.

[70] The production method according to any one of [66] to [69], wherein R¹ is an amino group protected with an acetyl group, a methoxyacetyl group, a trifluoroacetyl group, a trichloroacetyl group, a pivaloyl group, a formyl group, or a benzoyl group.

[71] The production method according to any one of [66] to [69], wherein R¹ is an amino group protected with an acetyl group or a trifluoroacetyl group.

[72] The production method according to any one of [66] to [69], wherein R¹ is an amino group protected with an acetyl group.

[73] The production method according to any one of [66] to [72], which is performed in the presence of a palladium complex prepared from palladium(II) acetate and tri(o-tolyl)phosphine.

[74] The production method according to any one of [66] to [73], comprising the steps of: dissolving the compound represented by formula (E) in a basic aqueous solution to wash the compound represented by formula (E) with a first organic solvent and separating the solvents; and then adding an acid to the basic aqueous solution to extract the compound represented by formula (E) with a second organic solvent and separating the solvents.

[75] The production method according to [74], wherein the first organic solvent is 2-methyltetrahydrofuran.

[76] The production method according to [74] or [75], wherein the second organic solvent is 2-methyltetrahydrofuran.

[77] The production method according to any one of [74] to [76], wherein the basic aqueous solution is an aqueous sodium hydroxide solution.

[78] A method for producing a compound represented by formula (B):

[Chem. 32]

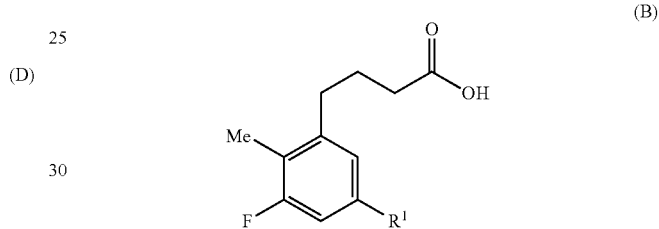

(B)

wherein R¹ represents an amino group protected with a protecting group, the method comprising a step of reducing a compound represented by formula (E):

[Chem. 31]

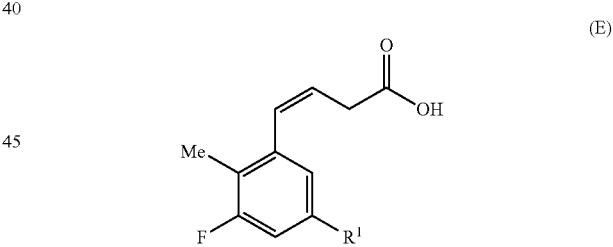

(E)

wherein R¹ represents the same meaning as above, to convert the compound represented by formula (E) into the compound represented by formula (B).

[79] The production method according to [78], wherein R¹ is an amino group protected with an acetyl group, a methoxyacetyl group, a trifluoroacetyl group, a trichloroacetyl group, a pivaloyl group, a formyl group, or a benzoyl group.

[80] The production method according to [78], wherein R¹ is an amino group protected with an acetyl group or a trifluoroacetyl group.

[81] The production method according to [78], wherein R¹ is an amino group protected with an acetyl group.

[82] The production method according to any one of [78] to [81], which is performed by a method comprising reacting the compound represented by formula (E) with hydrogen in a solvent in the presence of a palladium carbon catalyst.

[83] A method for producing a compound represented by formula (F):

[Chem. 34]

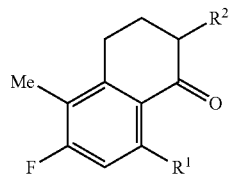
(F)

wherein $R^1$ represents an amino group protected with a protecting group, $R^2$ represents an amino group protected with a protecting group, the method comprising a step of converting a compound represented by formula (C):

[Chem. 33]

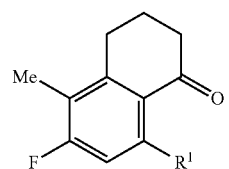
(C)

wherein $R^1$ represents the same meaning as above, into a compound represented by formula (F), wherein the step comprises the sub-steps of: (i) reacting the compound represented by formula (C) with a nitrous acid ester in the presence of a base to introduce a nitroso group; (ii) introducing a protecting group to a nitrogen atom derived from the nitroso group; and (iii) reducing the compound represented by formula (C) with hydrogen in the presence of a platinum carbon catalyst.

[84] The production method according to [83], wherein $R^1$ is an amino group protected with an acetyl group, a methoxyacetyl group, a trifluoroacetyl group, a trichloroacetyl group, a pivaloyl group, a formyl group, or a benzoyl group.

[85] The production method according to [83], wherein $R^1$ is an amino group protected with an acetyl group or a trifluoroacetyl group.

[86] The production method according to [83], wherein $R^1$ is an amino group protected with an acetyl group.

[87] The production method according to any one of [83] to [86], wherein $R^2$ is an amino group protected with an acetyl group, a methoxyacetyl group, a trifluoroacetyl group, a trichloroacetyl group, a pivaloyl group, a formyl group, or a benzoyl group.

[88] The production method according to any one of [83] to [86], wherein $R^2$ is an amino group protected with an acetyl group or a trifluoroacetyl group.

[89] The production method according to any one of [83] to [86], wherein $R^2$ is an amino group protected with an acetyl group.

[90] A method for producing a compound represented by formula (G):

[Chem. 36]

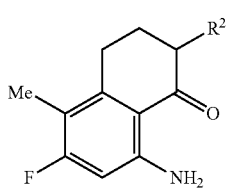
(G)

wherein $R^2$ represents an amino group protected with a protecting group, the method comprising a step of converting a compound represented by formula (F):

[Chem. 35]

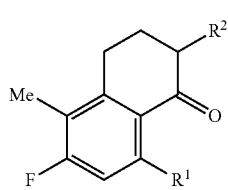
(F)

wherein $R^1$ represents an amino group protected with a protecting group and $R^2$ represents the same meaning as above, into the compound represented by formula (G) in a solvent comprising hydrochloric acid/ethanol.

[91] The production method according to [90], wherein $R^1$ is an amino group protected with an acetyl group, a methoxyacetyl group, a trifluoroacetyl group, a trichloroacetyl group, a pivaloyl group, a formyl group, or a benzoyl group.

[92] The production method according to [90], wherein $R^1$ is an amino group protected with an acetyl group or a trifluoroacetyl group.

[93] The production method according to [90], wherein $R^1$ is an amino group protected with an acetyl group.

[94] The production method according to any one of [90] to [93], wherein $R^2$ is an amino group protected with an acetyl group, a methoxyacetyl group, a trifluoroacetyl group, a trichloroacetyl group, a pivaloyl group, a formyl group, or a benzoyl group.

[95] The production method according to any one of [90] to [93], wherein $R^2$ is an amino group protected with an acetyl group or a trifluoroacetyl group.

[96] The production method according to any one of [90] to [93], wherein $R^2$ is an amino group protected with an acetyl group.

[97] A method for producing a compound represented by formula (H):

[Chem. 39]

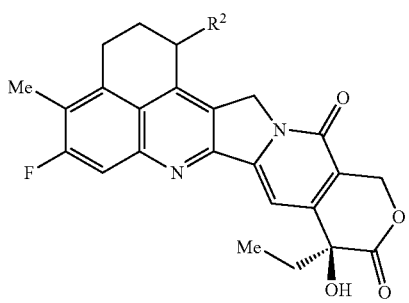

wherein R² represents an amino group protected with a protecting group, the method comprising a step of condensing a compound represented by formula (G):

[Chem. 37]

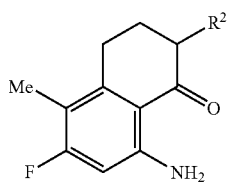

wherein R² represents the same meaning as above, with a compound represented by formula (1):

[Chem. 38]

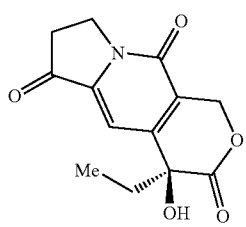

in a solvent comprising o-cresol to convert the compound represented by formula (G) into the compound represented by formula (H).

[98] The production method according to [97], wherein R² is an amino group protected with an acetyl group, a methoxyacetyl group, a trifluoroacetyl group, a trichloroacetyl group, a pivaloyl group, a formyl group, or a benzoyl group.

[99] The production method according to [97], wherein R² is an amino group protected with an acetyl group or a trifluoroacetyl group.

[100] The production method according to [97], wherein R² is an amino group protected with an acetyl group.

[101] The production method according to any one of [1] to [100], wherein no chromatography is used.

[102] A compound represented by formula (6).

[Chem. 40]

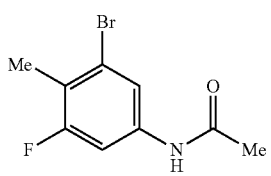

[103] A compound represented by formula (34).

[Chem. 41]

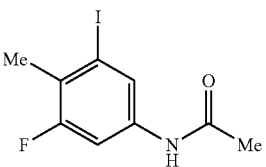

[104] A compound represented by formula (7).

[Chem. 42]

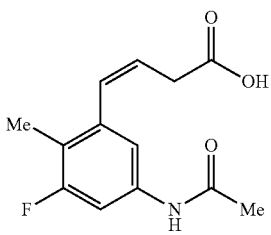

[105] A compound represented by formula (8).

[Chem. 43]

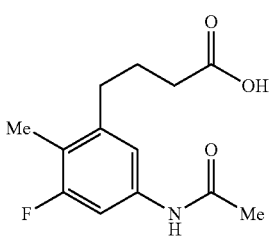

[106] A method for producing a compound represented by formula (14):

[Chem. 46]

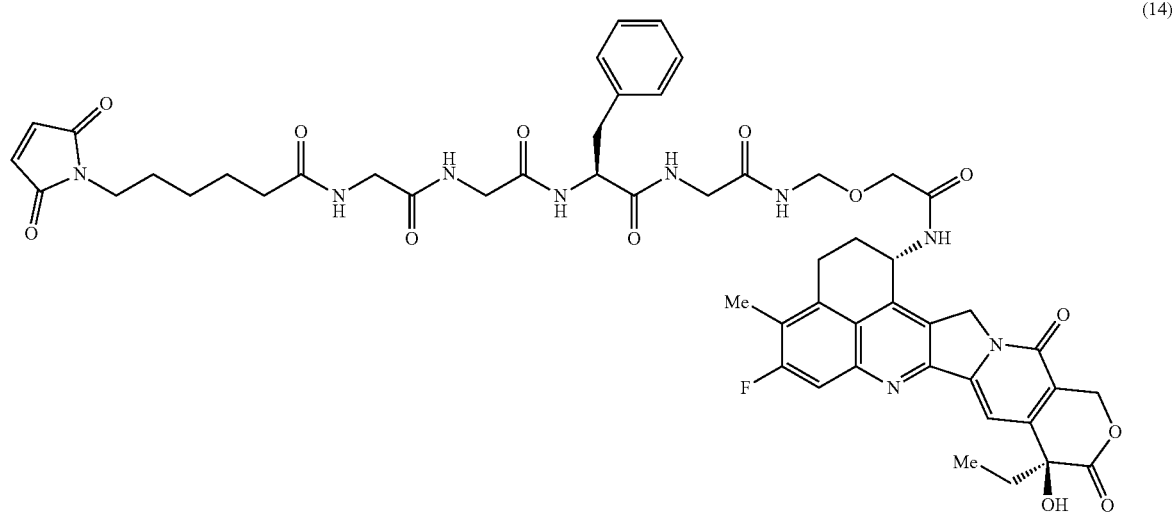

(14)

wherein a compound represented by formula (2):

[Chem. 44]

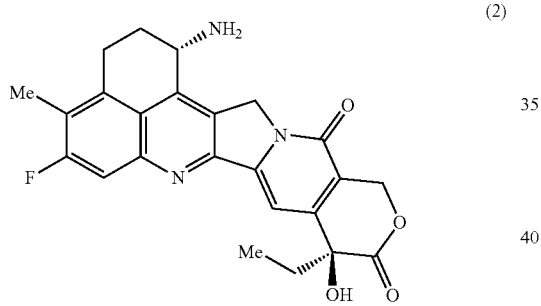

(2)

produced by the method according to any one of [34] to [65] is used as a starting material, the method comprising the steps of:
condensing the compound represented by formula (2) with a compound represented by formula (13):

[Chem. 45]

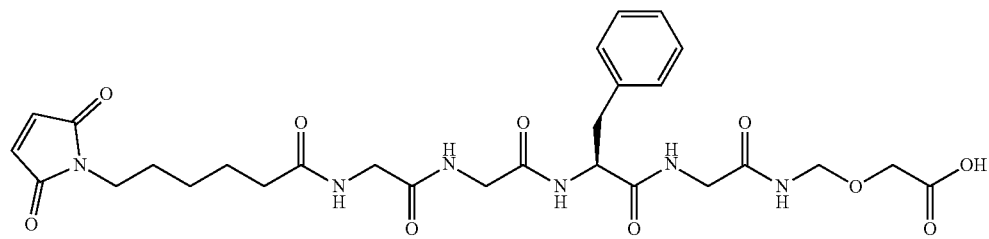

(13)

to convert the compound represented by formula (2) into the compound represented by formula (14).
[107] A method for producing an antibody-drug conjugate, in which a drug-linker represented by formula (15):

[Chem. 48]

(15)

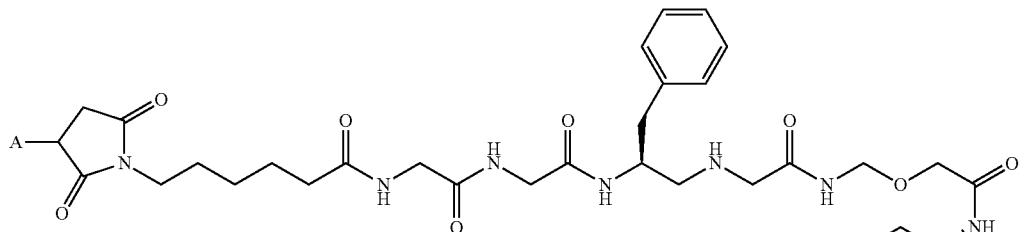
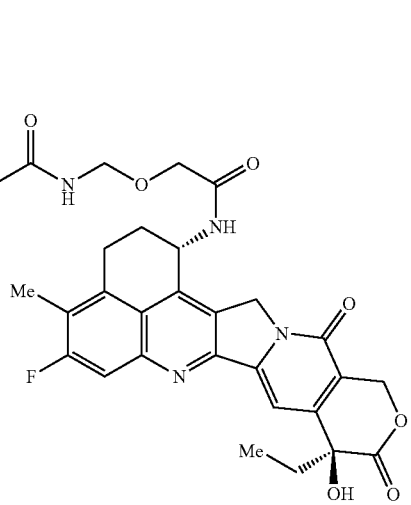

wherein A represents the connecting position to an antibody; is conjugated to the antibody via a thioether bond, wherein a compound represented by formula (14):

[Chem. 47]

(14)

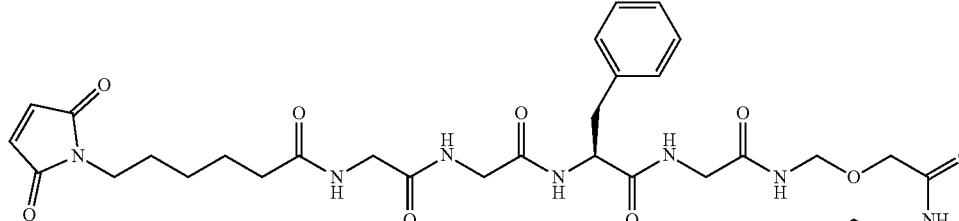
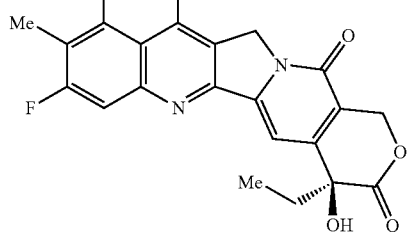

produced by the method according to [106] is used as a raw material,
the method comprising the steps of:
(i) reducing an antibody; and then
(ii) reacting the compound represented by formula (14) produced by the method with the reduced antibody.
[108] The production method according to [107], wherein the antibody is an anti-HER2 antibody, an anti-HER3 antibody, an anti-TROP2 antibody, an anti-B7-H3 antibody, or an anti-GPR20 antibody.
[109] The production method according to [108], wherein the antibody is an anti-HER2 antibody.
[110] The production method according to [109], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2; or an antibody comprising a heavy chain consisting of the amino acid sequence represented by SEQ ID NO: 1 and a light chain consisting of the amino acid sequence represented by SEQ ID NO: 2.
[111] The production method according to [109] or [110], wherein the average number of units of the drug-linker conjugated per antibody molecule in the antibody-drug conjugate is in the range of from 7 to 8.
[112] The production method according to [108], wherein the antibody is an anti-HER3 antibody.
[113] The production method according to [112], wherein the anti-HER3 antibody is an antibody comprising a heavy chain consisting of the amino acid sequence represented by SEQ ID NO: 3 and a light chain consisting of the amino acid sequence represented by SEQ ID NO: 4, or a variant of the antibody in which a lysine residue at the carboxyl terminus of the heavy chain is deleted.

[114] The production method according to [112] or [113], wherein the average number of units of the drug-linker conjugated per antibody molecule in the antibody-drug conjugate is in the range of from 7 to 8.

[115] The production method according to [108], wherein the antibody is an anti-TROP2 antibody.

[116] The production method according to [115], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or a variant of the antibody in which a lysine residue at the carboxyl terminus of the heavy chain is deleted.

[117] The production method according to [115] or [116], wherein the average number of units of the drug-linker conjugated per antibody molecule in the antibody-drug conjugate is in the range of from 3 to 5.

[118] The production method according to [108], wherein the antibody is an anti-B7-H3 antibody.

[119] The production method according to [118], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or a variant of the antibody in which a lysine residue at the carboxyl terminus of the heavy chain is deleted.

[120] The production method according to [118] or [119], wherein the average number of units of the drug-linker conjugated per antibody molecule in the antibody-drug conjugate is in the range of from 3 to 5.

[121] The production method according to [108], wherein the antibody is an anti-GPR20 antibody.

[122] The production method according to [121], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10, or a variant of the antibody in which a lysine residue at the carboxyl terminus of the heavy chain is deleted.

[123] The production method according to [121] or [122], wherein the average number of units of the drug-linker conjugated per antibody molecule in the antibody-drug conjugate is in the range of from 7 to 8.

Advantageous Effects of Invention

The present invention can provide a novel, industrially superior method for producing exatecan wherein the number of steps is small. Moreover, the present invention can provide a novel method for producing an antibody-drug conjugate wherein the aforementioned method is used.

BRIEF DESCRIPTION OF DRAWINGS

FIG. 1 shows an amino acid sequence of a heavy chain of an anti-HER2 antibody (SEQ ID NO: 1).

FIG. 2 shows an amino acid sequence of a light chain of an anti-HER2 antibody (SEQ ID NO: 2).

FIG. 3 shows an amino acid sequence of a heavy chain of an anti-HER3 antibody (SEQ ID NO: 3).

FIG. 4 shows an amino acid sequence of a light chain of an anti-HER3 antibody (SEQ ID NO: 4).

FIG. 5 shows an amino acid sequence of a heavy chain of an anti-TROP2 antibody (SEQ ID NO: 5).

FIG. 6 shows an amino acid sequence of a light chain of an anti-TROP2 antibody (SEQ ID NO: 6).

FIG. 7 shows an amino acid sequence of a heavy chain of an anti-B7-H3 antibody (SEQ ID NO: 7).

FIG. 8 shows an amino acid sequence of a light chain of an anti-B7-H3 antibody (SEQ ID NO: 8).

FIG. 9 shows an amino acid sequence of a heavy chain of an anti-GPR20 antibody (SEQ ID NO: 9).

FIG. 10 shows an amino acid sequence of a light chain of an anti-GPR20 antibody (SEQ ID NO: 10).

DESCRIPTION OF EMBODIMENTS

Hereinafter, preferred modes for carrying out the present invention are described. The embodiments described below are given merely for illustrating one example of a typical embodiment of the present invention and are not intended to limit the scope of the present invention.

[Antibody-Drug Conjugate]

The antibody-drug conjugate produced by the present invention is preferably an antibody-drug conjugate in which a drug-linker represented by formula (15):

[Chem. 49]

(15)

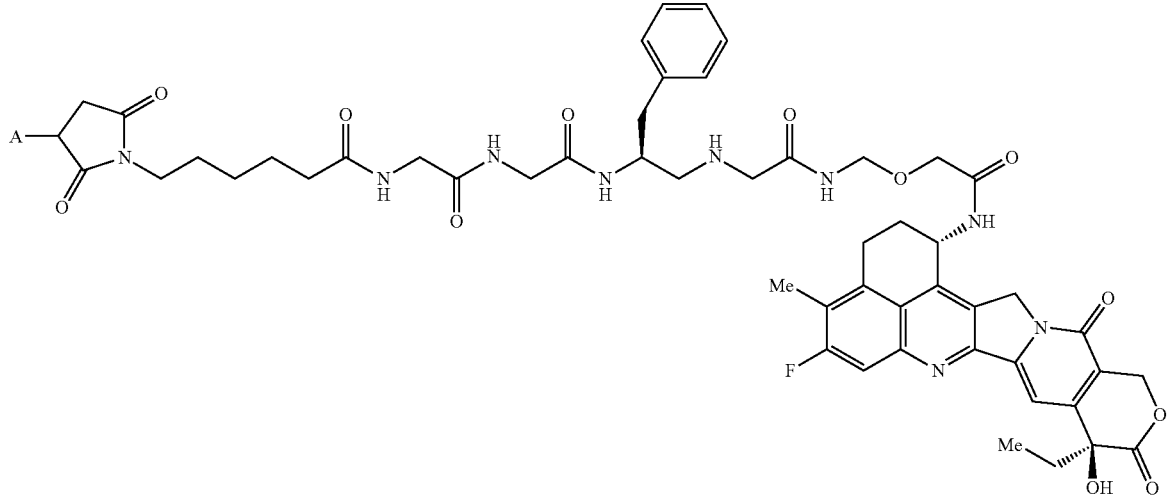

wherein A represents the connecting position to an antibody, is conjugated to the antibody via a thioether bond.

In the present invention, the partial structure consisting of a linker and a drug in the antibody-drug conjugate is referred to as a "drug-linker". The drug-linker is connected to a thiol group (in other words, the sulfur atom of a cysteine residue) formed at an interchain disulfide bond site (two sites between heavy chains, and two sites between a heavy chain and a light chain) in the antibody.

The drug-linker of the present invention includes exatecan, which is a topoisomerase I inhibitor, as a component. Exatecan is the compound represented by formula (2):

[Chem. 50]

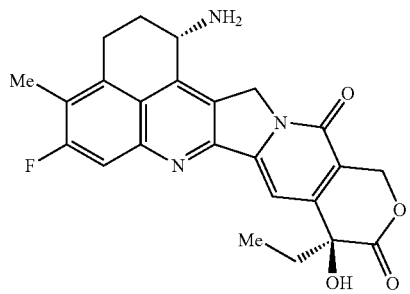

(2)

and is a camptothecin derivative having an antitumor effect.

The antibody-drug conjugate used in the present invention can also be represented by formula (16):

[Chem. 51]

wherein the drug-linker is conjugated to an antibody via a thioether bond. The meaning of n is the same as that of what is called the average number of conjugated drug molecules (DAR; Drug-to-Antibody Ratio), and indicates the average number of units of the drug-linker conjugated per antibody molecule.

After migrating into cancer cells, the antibody-drug conjugate used in the present invention releases the compound represented by formula (18):

[Chem. 52]

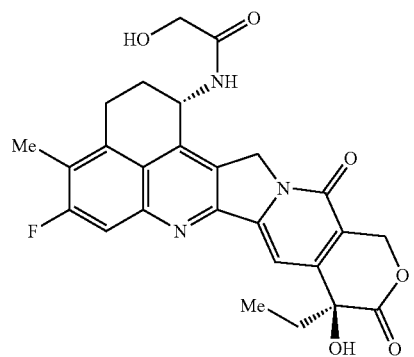

(18)

and thereby exerts an anti-tumor effect.

The compound represented by formula (18) is inferred to be the original source of the antitumor activity of the antibody-drug conjugate produced by the present invention, and has been confirmed to have a topoisomerase I inhibitory effect (Ogitani Y. et al., Clinical Cancer Research, 2016 Oct. 15; 22(20):5097-5108, Epub 2016 Mar. 29).

The compound represented by formula (18) is inferred to be formed by decomposition of an aminal structure of the compound represented by formula (17):

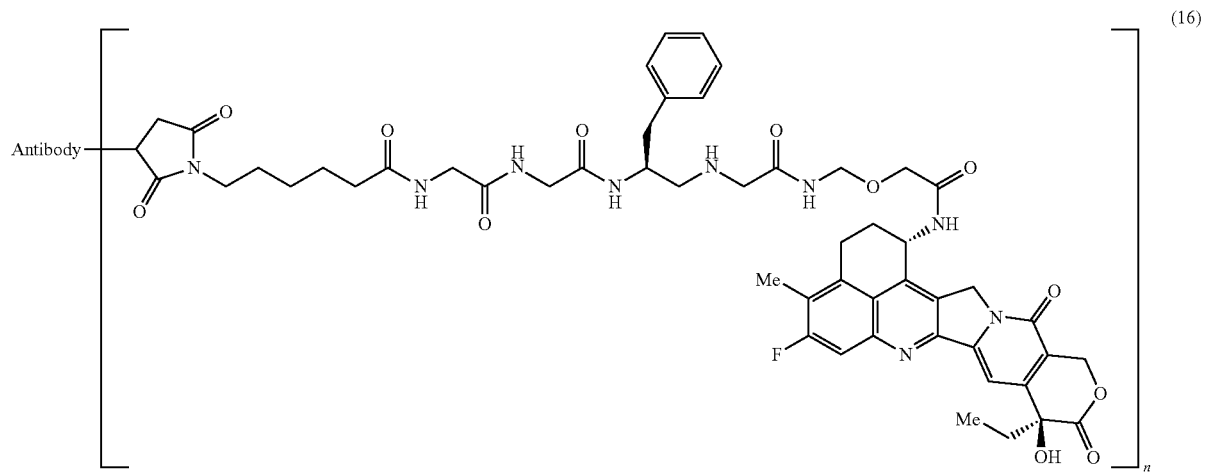

(16)

[Chem. 53]

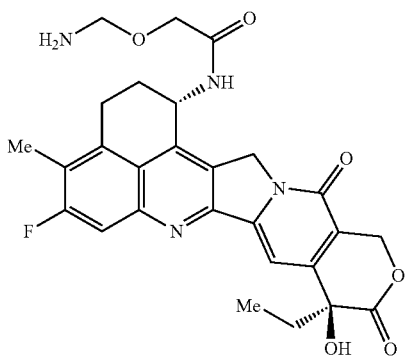

which is inferred to be formed by cleavage at the linker part of the antibody-drug conjugate produced by the present invention.

The antibody-drug conjugate produced by the present invention is known to have a bystander effect (Ogitani Y. et al., Cancer Science (2016) 107, 1039-1046).

The bystander effect is exerted through a process in which the antibody-drug conjugate produced by the present invention is internalized in cancer cells expressing a target and the compound represented by formula (18) released then exerts an antitumor effect also on cancer cells which are present therearound and not expressing the target.

[Production of Exatecan]

The production of exatecan according to the present invention can be performed by the following method:

[Chem. 54]

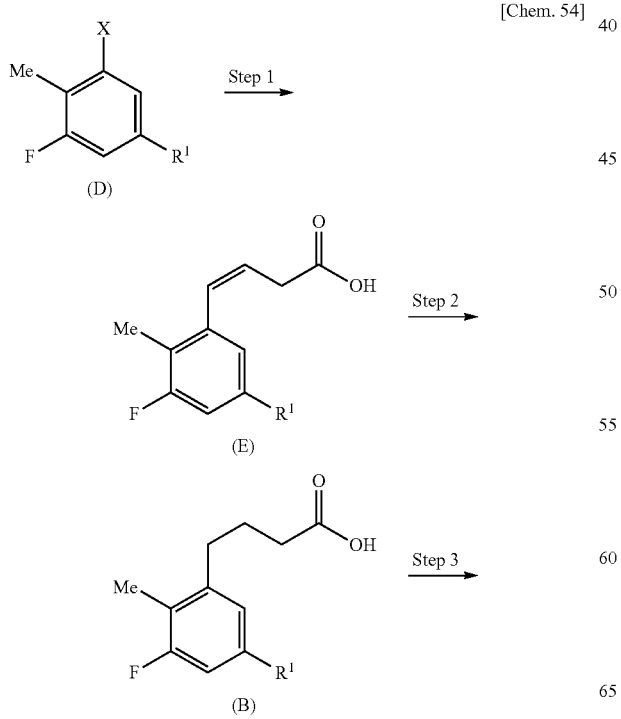

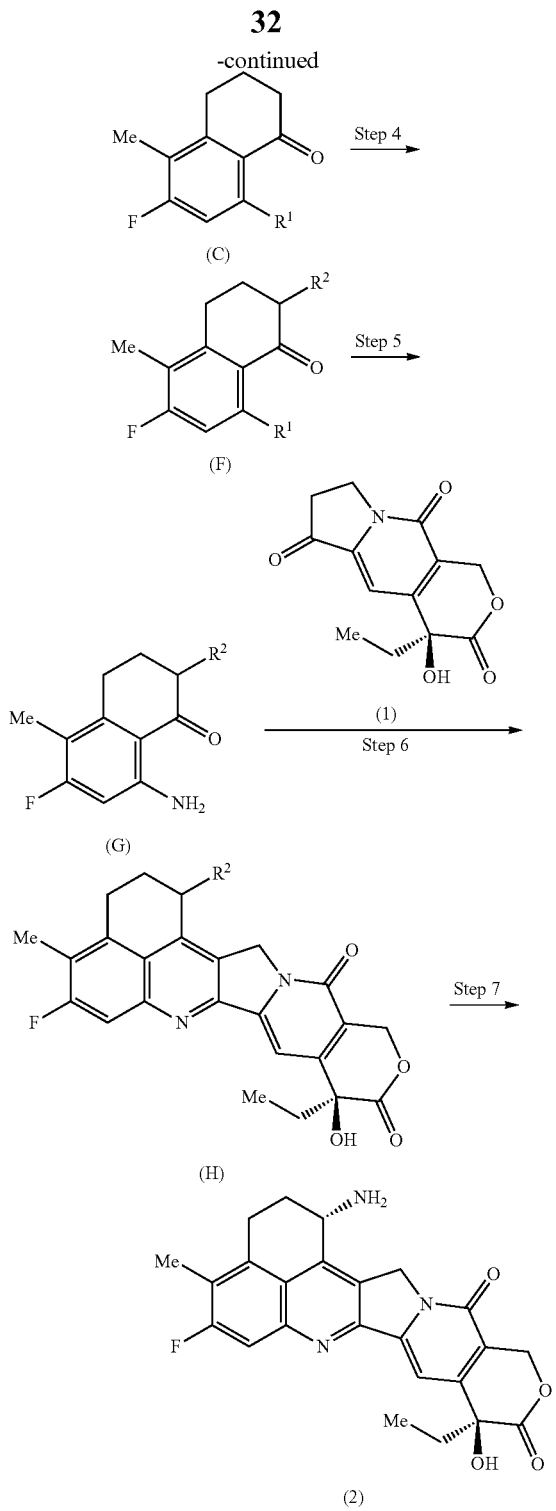

In the scheme, X represents a leaving group, preferably represents a bromo group, an iodo group, a trifluoromethanesulfonyloxy group, or an arylsulfonyloxy group, more preferably represents a bromo group or an iodo group, and even more preferably a bromo group; $R^1$ represents an amino group protected with a protecting group, preferably represents an amino group protected with an acetyl group, a methoxyacetyl group, a trifluoroacetyl group, a trichloroacetyl group, a pivaloyl group, a formyl group, or a benzoyl group, more preferably represents an amino group protected with an acetyl group or a trifluoroacetyl group, and even more preferably represents an amino group protected with an acetyl group; and $R^2$ represents a protected amino group, preferably represents an amino group protected with an acetyl group, a methoxyacetyl group, a trifluoroacetyl group, a trichloroacetyl group, a pivaloyl group, a formyl group, or a benzoyl group, more preferably represents an amino group protected with an acetyl group or a trifluoroacetyl group, and even more preferably represents an amino group protected with an acetyl group.

Step 1:

This step is a step of coupling a compound represented by formula (D) with 3-butenoic acid to convert the compound into a compound represented by formula (E). The compound represented by formula (D) can be produced with reference to a known method. The amount of 3-butenoic acid used in this step is not limited as long as the reaction proceeds, and is preferably 1 to 1.5 equivalents based on the compound represented by formula (D).

The coupling reaction can be performed in the presence of a transition metal catalyst, preferably in the presence of a palladium catalyst. The palladium catalyst used in this step is not particularly limited as long as the reaction proceeds, and, for example, divalent palladium salts such as palladium (II) acetate, palladium(II) trifluoroacetate, palladium(II) chloride, palladium(II) bromide, palladium(II) iodide, and bis(triphenylphosphine)palladium(II) chloride, complexes thereof, zero-valent palladium metals such as palladium black, palladium carbon, tetrakistriphenylphosphinepalladium(0), bis(dibenzylideneacetone)palladium(0), and complexes thereof can be used, and palladium(II) acetate can preferably be used. The amount of the palladium catalyst used in this step is not limited as long as the reaction proceeds, and is preferably 0.003 to 0.03 equivalents based on the compound represented by formula (D).

Moreover, in this step, in addition to the above palladium catalyst, a ligand for forming a palladium complex in the reaction system can preferably be used. Examples of the ligand that can be used in this step include triphenyl phosphine, tri(o-tolyl)phosphine, tri(3-methoxyphenyl)phosphine, tri(4-chlorophenyl)phosphine, tri(2-furyl)phosphine, tri(2-thienyl)phosphine, 1,2-bis(diphenylphosphino)ethane, and Buchwald ligands (such as 2-dicyclohexylphosphino-2',6'-dimethoxybiphenyl (SPhos) and 2-dicyclohexylphosphino-2',4',6'-triisopropylbiphenyl (XPhos)), and tri(o-tolyl) phosphine can preferably be used. The amount of the ligand used in this step is not limited as long as the reaction proceeds, and is preferably 0.006 to 0.06 equivalents based on the compound represented by formula (D).

This step can be suitably performed in the presence of a base. The base used in the present step is not particularly limited as long as the reaction proceeds, and examples include organic bases such as triethylamine, tributylamine, diisopropylethylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, and 1,5-diazabicyclo[4.3.0]undec-7-ene, and inorganic bases such as potassium carbonate, potassium hydroxide, potassium hydrogen carbonate, sodium carbonate, sodium hydroxide, sodium hydrogen carbonate, sodium acetate, potassium acetate, sodium methoxide, sodium ethoxide, and potassium tert-butoxide; preferably include triethylamine, tributylamine, diisopropylethylamine, potassium carbonate, potassium hydroxide, potassium hydrogen carbonate, sodium carbonate, sodium hydroxide, sodium hydrogen carbonate, sodium acetate, and potassium acetate; and more preferably include diisopropylethylamine. The amount of the base used in this step is not limited as long as the reaction proceeds, and is preferably 2 to 3 equivalents based on the compound represented by formula (D).

The solvent used in this step is not particularly limited as long as it does not inhibit the reaction, and, for example, acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof can be used, and tetrahydrofuran is preferred.

The reaction temperature of this step is not limited as long as the reaction proceeds, and is preferably 45 to 85° C., and more preferably a temperature at which tetrahydrofuran is thermally refluxed. The reaction time of this step is not limited as long as the reaction proceeds, and is preferably 2.5 to 10 hours.

The compound represented by formula (E) can preferably be purified by performing the steps of dissolving the compound represented by formula (E) in a basic aqueous solution to wash the compound represented by formula (E) with a first organic solvent and separating the solvents, and then adding an acid to the basic aqueous solution to extract the compound represented by formula (E) with a second organic solvent and separating the solvents. The first organic solvent is preferably 2-methyltetrahydrofuran. The second organic solvent is preferably 2-methyltetrahydrofuran. The basic aqueous solution is preferably an aqueous sodium hydroxide solution.

E and Z forms of the compound represented by formula (E) exist as geometric isomers, and both are encompassed within the compound represented by formula (E) and are thus encompassed within the scope of the present invention. The compound represented by formula (E) of the present invention may be a mixture of the E and Z forms, and the mixture can be directly used in the next step.

In this step, a 3-butenoic acid ester can also be used in place of 3-butenoic acid. In such a case, the product obtained by coupling the compound represented by formula (D) with a 3-butenoic acid ester can be hydrolyzed to convert the compound into the compound represented by formula (E).

Step 2:

This step is a step of reducing the compound represented by formula (E) to convert the compound into a compound represented by formula (B).

The reduction in this step is not limited as long as the reaction proceeds, and can preferably be performed under a hydrogen atmosphere (preferably in a hydrogen stream of 0.05 to 0.6 MPa) using a palladium catalyst, a platinum catalyst, a nickel catalyst, a ruthenium catalyst, or a rhodium catalyst, more preferably it can be performed using a palladium catalyst, even more preferably it can be performed using palladium carbon, and still more preferably it can be performed using 5% palladium carbon. The amount of 5% palladium carbon used in this step is not limited as long as the reaction proceeds, and is preferably 5 to 80% by weight based on the compound represented by formula (D) used in step 1.

The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably 2-methyltetrahydrofuran.

The reaction temperature of this step is not limited as long as the reaction proceeds, and is preferably 20 to 60° C. The reaction time of this step is not limited as long as the reaction proceeds, and is preferably 0.5 to 2 hours.

Step 3:

This step is a step of subjecting the compound represented by formula (B) to intramolecular cyclization to convert the compound into a compound represented by formula (C). Intramolecular cyclization can preferably be performed by an intramolecular Friedel-Crafts acylation reaction. Concerning the intramolecular Friedel-Crafts acylation reaction in this step, the method is not limited as long as the reaction proceeds, and preferred examples include a method involving trifluoroacetic anhydride and a method involving thionyl chloride, sulfuryl chloride, oxalyl chloride, phosphorus oxychloride, phosphorus trichloride, or phosphorus pentachloride, more preferably a method involving trifluoroacetic anhydride or thionyl chloride, and even more preferably a method involving trifluoroacetic anhydride. The amount of trifluoroacetic anhydride used in this step is not limited as long as the reaction proceeds, and is preferably 1 to 3 equivalents based on the compound represented by formula (B). The amount of thionyl chloride used in this step is not limited as long as the reaction proceeds, and is preferably 1 to 3 equivalents based on the compound represented by formula (B).

In the case of a method involving trifluoroacetic anhydride, this step is preferably performed in the presence of acid, and is more preferably performed in the presence of trifluoroacetic acid. In the case of a method involving thionyl chloride, sulfuryl chloride, oxalyl chloride, phosphorus oxychloride, phosphorus trichloride, or phosphorus pentachloride, this step is preferably performed in the presence of aluminium chloride. The amount of aluminium chloride used in this step is not limited as long as the reaction proceeds, and is preferably 1 to 5 equivalents based on the compound represented by formula (B).

The solvent used in this step is not particularly limited as long as it does not inhibit the reaction, and examples include dichloromethane, chloroform, diethyl ether, 1,2-dimethoxyethane, hexane, pentane, heptane, cyclohexane, ethylcyclohexane, benzene, toluene, and chlorobenzene, and mixed solvents thereof, and preferably methylene chloride. In the case of a method involving trifluoroacetic acid, trifluoroacetic acid can preferably be included as a solvent.

The reaction temperature of this step is not limited as long as the reaction proceeds, and in the case of a method involving trifluoroacetic anhydride, the reaction temperature is preferably −10° C. to 20° C., and in the case of a method involving thionyl chloride, the reaction temperature is preferably 10° C. to 40° C. The reaction time of this step is not limited as long as the reaction proceeds, and in the case of a method involving trifluoroacetic anhydride, the reaction time is preferably 2 hours to 8 hours, and in the case of a method involving thionyl chloride, the reaction time is preferably 1 hour to 4 hours.

This step can also be divided into the following two sub-steps:

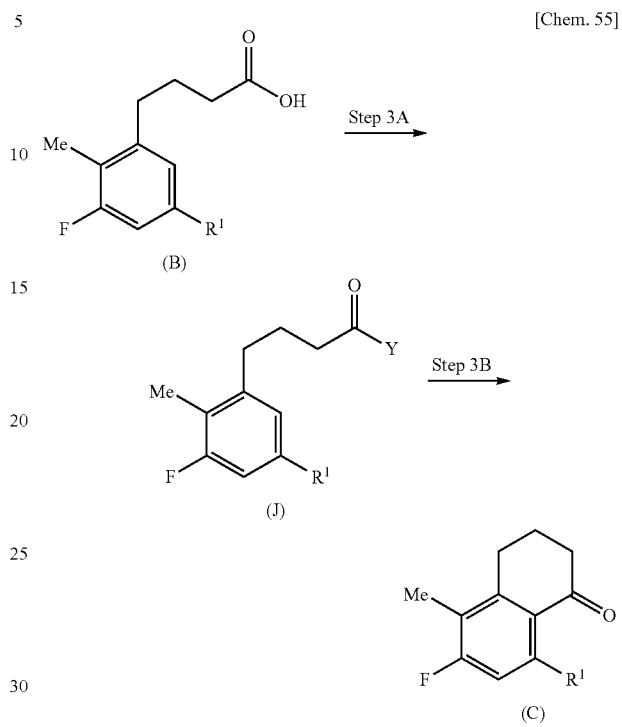

[Chem. 55]

In the scheme, Y represents a leaving group, preferably represents a chloro group, a bromo group, an iodo group, a fluoro group, or a trifluoroacetoxy group, and more preferably represents a chloro group or a trifluoroacetoxy group; and $R^1$ represents an amino group protected with a protecting group, preferably represents an amino group protected with an acetyl group, a methoxyacetyl group, a trifluoroacetyl group, a trichloroacetyl group, a pivaloyl group, a formyl group, or a benzoyl group, more preferably represents an amino group protected with an acetyl group or a trifluoroacetyl group, and even more preferably represents an amino group protected with an acetyl group.

Step 3A is a step of converting the compound represented by formula (B) into a compound represented by formula (J).

When Y is a chloro group, this step can preferably be performed by a method involving thionyl chloride, sulfuryl chloride, oxalyl chloride, phosphorus oxychloride, phosphorus trichloride, or phosphorus pentachloride, and this step can be more preferably performed by a method involving thionyl chloride. The amount of thionyl chloride used in this step is not limited as long as the reaction proceeds, and is preferably 1 to 3 equivalents based on the compound represented by formula (B). When Y is a trifluoroacetoxy group, this step can preferably be performed by a method involving trifluoroacetic anhydride. The amount of trifluoroacetic anhydride used in this step is not limited as long as the reaction proceeds, and is preferably 1 to 3 equivalents based on the compound represented by formula (B). The solvent used in this step is not particularly limited as long as it does not inhibit the reaction, and examples include dichloromethane, chloroform, diethyl ether, 1,2-dimethoxyethane, hexane, pentane, heptane, cyclohexane, ethylcyclohexane, benzene, toluene, chlorobenzene, trifluoroacetic acid, and mixed solvents thereof, preferably methylene chloride in the case of a method involving thionyl chloride, and preferably trifluoroacetic acid in the case of a method involving trifluoroacetic anhydride.

Step 3B is a step of converting the compound represented by formula (J) into a compound represented by formula (C). In the case of a method involving thionyl chloride, this step can preferably be performed in the presence of aluminium chloride. The amount of aluminium chloride used in this step is not limited as long as the reaction proceeds, and is preferably 1 to 5 equivalents based on the compound represented by formula (B). In the case of a method involving trifluoroacetic anhydride, this step can preferably be performed in the presence of an acid, and this step can more preferably be performed in the presence of trifluoroacetic acid.

The reaction temperature of step 3A and step 3B is not limited as long as the reactions proceed, and in the case of a method involving thionyl chloride, the reaction temperature is preferably 10° C. to 40° C., and in the case of a method involving trifluoroacetic anhydride, the reaction temperature is preferably −10° C. to 20° C. The total reaction time of step 3A and step 3B is not limited as long as the reaction proceeds, and in the case of a method involving thionyl chloride, the total reaction time is preferably 1 hour to 4 hours, and in the case of a method involving trifluoroacetic anhydride, the total reaction time is preferably 2 hours to 8 hours.

Step 4:

Step 4 is a step of converting the compound represented by formula (C) into a compound represented by formula (F). This step can preferably be performed by the sub-steps of (i) nitrosating (or oximating) the α-position of the carbonyl group, (ii) introducing a protecting group to the nitrogen atom derived from the nitroso group (or the oxime group), and (iii) reducing. Sub-steps (ii) and (iii) may be performed in a reversed order, or may be simultaneously performed.

The nitrosating agent (or the oximating agent) used in sub-step (i) is not particularly limited as long as the α-position of the carbonyl group of the compound represented by formula (C) can be nitrosated (or oximated), and nitrous acid esters can preferably be used, amyl nitrite, n-butyl nitrite, and tert-butyl nitrite can more preferably be used, and amyl nitrite can even more preferably be used. The amount of amyl nitrite used in sub-step (i) is not limited as long as the reaction proceeds, and is preferably 1 to 1.6 equivalents based on the compound represented by formula (C).

A base is preferably used in sub-step (i). The base used in sub-step (i) is not particularly limited as long as it is applicable to the nitrosation (or the oximation) of the α-position of the carbonyl group of the compound represented by formula (C), and potassium tert-butoxide can preferably be used. The amount of potassium tert-butoxide used in sub-step (i) is not limited as long as the reaction proceeds, and is preferably 1 to 1.5 equivalents based on the compound represented by formula (C).

The solvent used in sub-step (i) is not particularly limited as long as it does not inhibit the reaction, and examples include diethyl ether, 1,2-dimethoxyethane, tetrahydrofuran, 2-methyltetrahydrofuran, 1,4-dioxane, hexane, pentane, heptane, cyclohexane, ethylcyclohexane, benzene, toluene, chlorobenzene, dimethyl sulfoxide, and mixed solvents thereof, and preferably tetrahydrofuran.

The reaction temperature of sub-step (i) is not limited as long as the reaction proceeds, and is preferably −10 to 20° C. The reaction time of this sub-step is not limited as long as the reaction proceeds, and is preferably 1.5 to 30 hours.

The reaction conditions of sub-step (ii) can be suitably set according to the type of protecting group for amino group $R^2$. When $R^2$ is an amino group protected with an acetyl group, acetic anhydride in acetic acid can preferably be used in sub-step (ii).

Sub-step (iii) can be performed under a hydrogen atmosphere (preferably in a hydrogen stream at 0.15 to 1.2 MPa) using, for example, a platinum carbon catalyst or zinc powder, can preferably be performed using a platinum carbon catalyst, and can more preferably be performed using a 2% or 5% platinum carbon catalyst. The amount of the 2% or 5% platinum carbon catalyst is not limited as long as the reaction proceeds, and is preferably 5 to 60% by weight based on the compound represented by formula (C). In sub-step (iii), a solvent as used in sub-step (ii) can be used.

The reaction temperature of sub-steps (ii) and (iii) is not limited as long as the reactions proceed, and is preferably 0 to 40° C. The total reaction time of sub-steps (ii) and (iii) is not limited as long as the reactions proceed, and is preferably 2 to 8 hours.

Step 5:

This step is the step of selectively deprotecting the protecting group for the aromatic amino group of the compound represented by formula (F) to convert the compound into a compound represented by formula (G). The reaction conditions of this step can suitably be set according to the type of the protecting group for amino groups $R^1$ and $R^2$. When $R^1$ and $R^2$ are amino groups protected with an acetyl group, this step can preferably be performed using hydrochloric acid, and can more preferably be performed using 2N hydrochloric acid/ethanol.

The reaction temperature of this step is not limited as long as the reaction proceeds, and is preferably 40 to 60° C. The reaction time of this step is not limited as long as the reaction proceeds, and is preferably 2 to 14 hours.

Step 6:

This step is a step of condensing the compound represented by formula (G) with a compound represented by formula (1) to convert the compound into a compound represented by formula (H). The compound represented by formula (1) can be produced with reference to descriptions in U.S. Pat. No. 4,778,891 or the like, or a commercially available compound can be used. The amount of the compound represented by formula (1) used in this step is not limited as long as the reaction proceeds, and is preferably 0.8 to 1.2 equivalents based on the compound represented by formula (G).

This step is performed in the presence of an acid catalyst. A preferred example of the acid catalyst used in this step can be pyridinium p-toluenesulfonate. The amount of the acid catalyst used in this step is not limited as long as the reaction proceeds, and is preferably 0.03 to 0.3 equivalents based on the compound represented by formula (G).

This step is preferably performed in a solvent containing cresol or phenol, and more preferably performed in toluene containing o-cresol. Due to the presence of o-cresol or phenol, the compound represented by formula (H) is precipitated in an improved manner, and effects such as an improved yield and a shortened reaction time can be observed.

The reaction temperature of this step is not limited as long as the reaction proceeds, and is preferably 90 to 130° C., and more preferably a temperature at which toluene is thermally refluxed. The reaction time of this step is not limited as long as the reaction proceeds, and is preferably 16 to 64 hours.

This step is considered to proceed via a compound represented by formula (K) and a compound represented by formula (L) as reaction intermediates.

[Chem. 56]

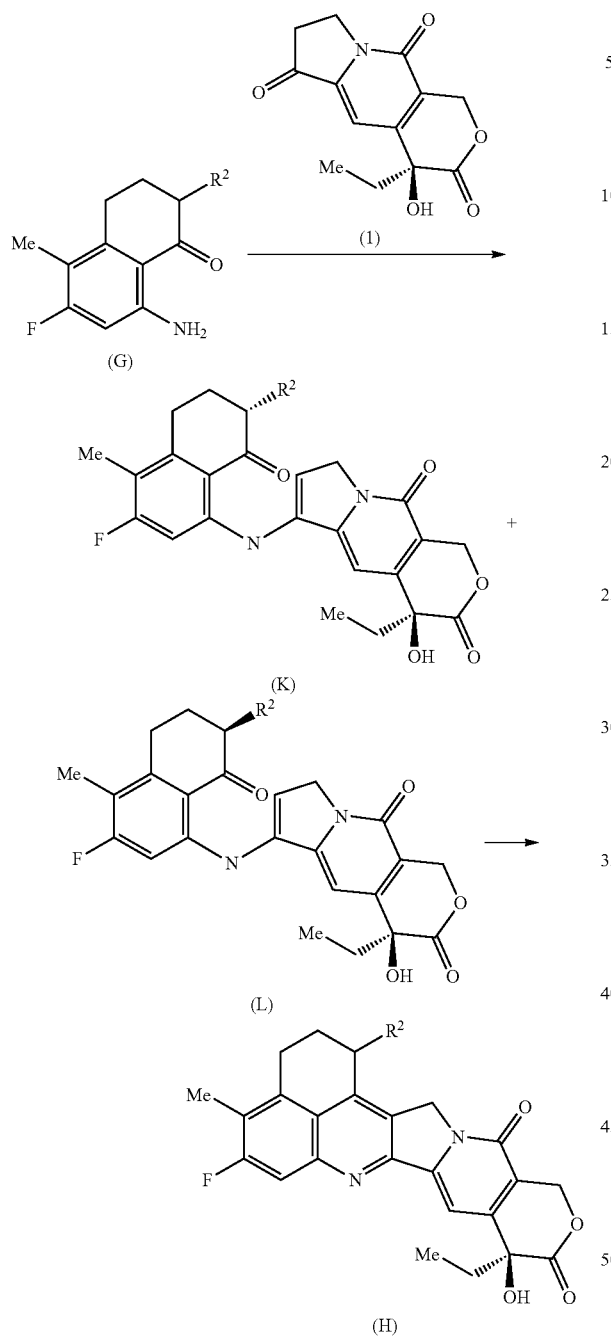

Step 7:

This step is a step of converting a compound represented by formula (H) into a compound represented by formula (2). The compound represented by formula (2) may be a salt or even a hydrate, and both are encompassed within the scope of a "compound represented by formula (2)" in the present invention.

This step can preferably be performed in the presence of acid, and more preferably in the presence of methanesulfonic acid and water.

The solvent used in this step is not particularly limited as long as it does not inhibit the reaction, preferably solvents containing 2-methoxyethanol and ethylcyclohexane can be used, and, moreover, in the case of including the above acid as a solvent, a mixed solvent of methanesulfonic acid, water, 2-methoxyethanol, and ethylcyclohexane can more preferably be used.

This step is not limited as long as the reaction proceeds, and can preferably be performed at 80 to 160° C. and can more preferably be performed at a temperature at which the mixed solvent of methanesulfonic acid, water, 2-methoxyethanol, and ethylcyclohexane is thermally refluxed. The reaction time of this step is not limited as long as the reaction proceeds, and is preferably 4 to 16 hours.

The compound represented by formula (2) can preferably be obtained as a methanesulfonic acid salt, can more preferably be obtained as a methanesulfonic acid m-hydrate wherein m is 0 to 3, can even more preferably be obtained as a methanesulfonic acid salt anhydrate, a methanesulfonic acid salt monohydrate, a methanesulfonic acid salt dihydrate, or a methanesulfonic acid salt trihydrate, and can still more preferably be obtained as a methanesulphonic acid dihydrate, any of which can be used in the production method of the present invention. The number of water molecules in the hydrates can be controlled by regulating the humidity available when obtaining and drying crystals.

The compound represented by formula (2) can more preferably be produced according to the following method.

[Chem. 57]

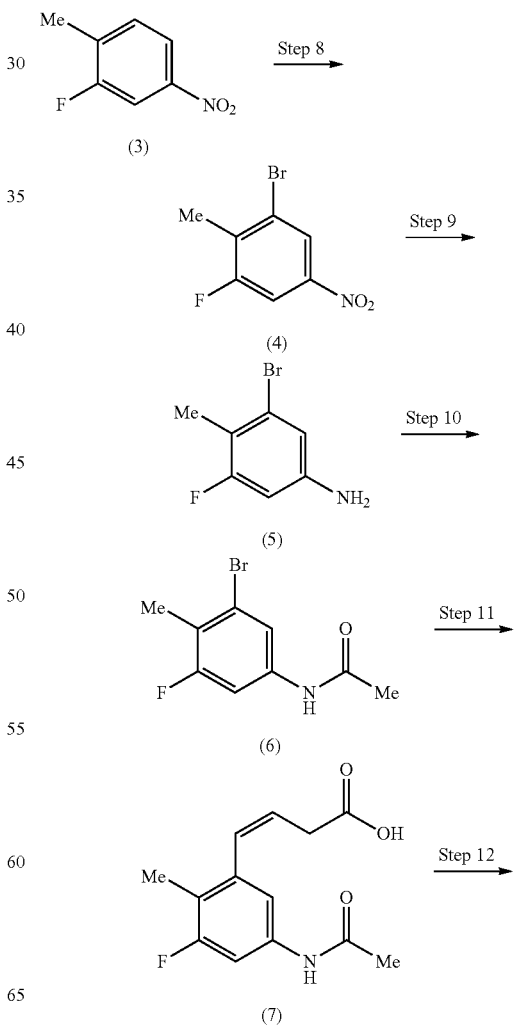

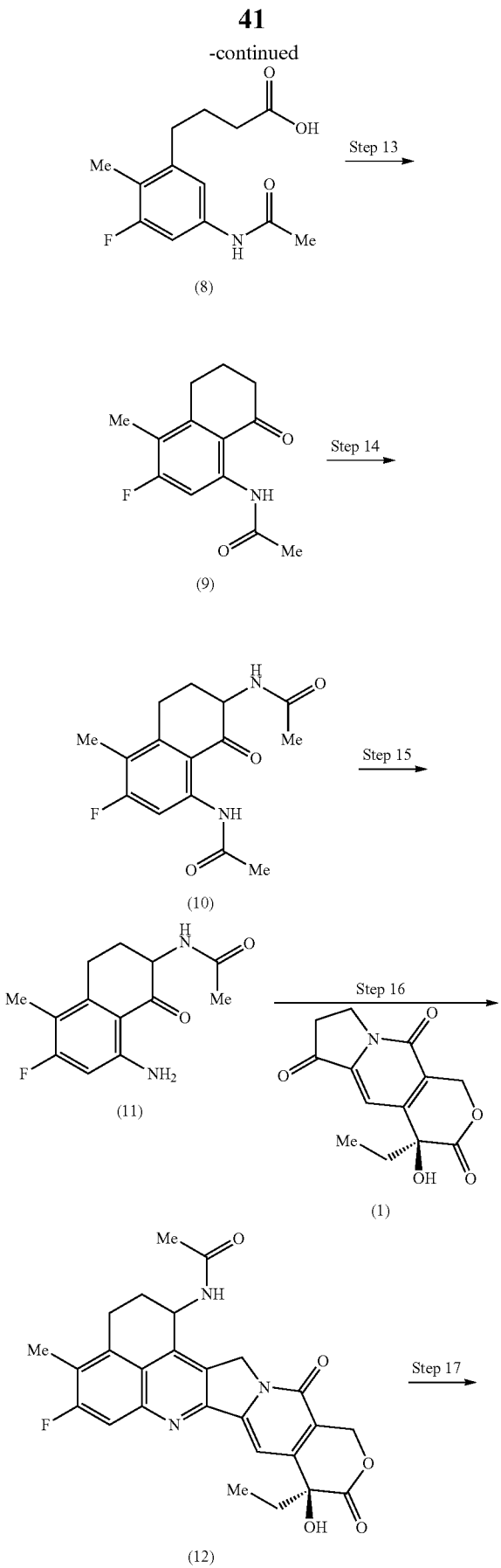

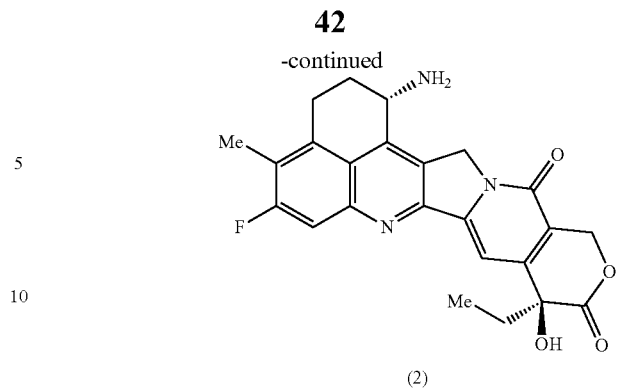

Step 8:

This step is a step of brominating the compound represented by formula (3) to convert the compound into a compound represented by formula (4). As the compound represented by formula (3), a compound produced by a known method or a commercially available compound can be used.

The brominating agent used in this step is not limited as long as the reaction proceeds, and examples include bromine and N-bromosuccinimide, and preferably N-bromosuccinimide. The amount of N-bromosuccinimide used in this step is not limited as long as the reaction proceeds, and is preferably 1 to 1.5 equivalents based on the compound represented by formula (3). This step can preferably be performed in a mixed solvent of sulfuric acid and a further solvent.

The further solvent is not particularly limited as long as it does not inhibit the reaction, and examples include dichloromethane, chloroform, diethyl ether, 1,2-dimethoxyethane, hexane, pentane, heptane, cyclohexane, ethylcyclohexane, benzene, toluene, chlorobenzene, and mixed solvents thereof, and preferably heptane.

The reaction temperature of this step is not limited as long as the reaction proceeds, and is preferably 50 to 70° C. The reaction time of this step is not limited as long as the reaction proceeds, and is preferably 0.5 to 2 hours.

Step 9:

This step is a step of reducing the nitro group of the compound represented by formula (4) to an amino group to convert the compound into a compound represented by formula (5). The reducing agent used in this step is not limited as long as it does not allow debromination to proceed and is capable of selectively reducing only the nitro group, preferably a platinum carbon catalyst can be used in the presence of hydrogen (preferably in a hydrogen stream of 0.05 to 0.2 MPa), and more preferably a 1% platinum carbon catalyst can be used. The amount of the platinum carbon catalyst used in this step is not limited as long as the reaction proceeds, and is preferably 5 to 40% by weight based on the compound represented by formula (3) used in step 8. The solvent used in this step is not particularly limited as long as it does not inhibit the reaction, and examples include methanol, ethanol, 1,2-dimethoxyethane, tetrahydrofuran, 2-methyltetrahydrofuran, 1,4-dioxane, ethyl acetate, and water, and mixed solvents thereof, and preferably ethyl acetate. The reaction temperature of this step is not limited as long as the reaction proceeds, and is preferably 50 to 70° C. The reaction time of this step is not limited as long as the reaction proceeds, and is preferably 2 to 8 hours.

Step 10:

This step is a step of acetylating the amino group of the compound represented by formula (5) to convert the compound into a compound represented by formula (6). Examples of the acetylating agent used in this step include acetic anhydride and acetyl chloride, and preferably acetic anhydride. The amount of acetic anhydride used in this step is not limited as long as the reaction proceeds, and is preferably 0.5 to 1 equivalent based on the compound represented by formula (3) used in step 8. A base can preferably be used in this step. The base is not limited as long as the reaction proceeds, and is preferably triethylamine. The amount of the base is not limited as long as the reaction proceeds, and is preferably 0.75 to 1.5 equivalents based on the compound represented by formula (3) used in step 8. The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably ethyl acetate. The reaction temperature of this step is not limited as long as the reaction proceeds, and is preferably 10 to 40° C. The reaction time of this step is not limited as long as the reaction proceeds, and is preferably 3 to 12 hours.

Step 11:

This step is a step of coupling the compound represented by formula (6) with 3-butenoic acid to convert the compound into a compound represented by formula (7). This step can be performed in the same manner as the method described in step 1.

E and Z forms of the compound represented by formula (7) exist as geometric isomers, and both are encompassed within the compound represented by formula (7) and are thus encompassed within the scope of the present invention. The compound represented by formula (7) of the present invention may be a mixture of the E and Z forms, and the mixture can be directly used in the next step.

Step 12:

This step is a step of reducing the compound represented by formula (7) to convert the compound into a compound represented by formula (8).

The reduction in this step is not limited as long as the reaction proceeds, and can preferably be performed under a hydrogen atmosphere (preferably in a hydrogen stream of 0.05 to 0.2 MPa) using a palladium catalyst, a platinum catalyst, a nickel catalyst, a ruthenium catalyst, or a rhodium catalyst, more preferably can be performed using a palladium catalyst, and even more preferably can be performed using palladium carbon, and still more preferably 5% palladium carbon can be used. The amount of 5% palladium carbon used in this step is not limited as long as the reaction proceeds, and is preferably 5 to 40% by weight based on the compound represented by formula (7) used in step 11.

The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably 2-methyltetrahydrofuran.

The reaction temperature of this step is not limited as long as the reaction proceeds, and is preferably 20 to 60° C. The reaction time of this step is not limited as long as the reaction proceeds, and is preferably 0.5 to 2 hours.

Step 13:

This step is a step of subjecting the compound represented by formula (8) to intramolecular cyclization to convert the compound into a compound represented by formula (9). This step can be performed in the same manner as the method described in step 3.

Step 14:

This step is a step of converting the compound represented by formula (9) into a compound represented by formula (10). This step can be performed in the same manner as the method described in step 4.

Step 15:

This step is a step of selectively deprotecting the protecting group for the aromatic amino group of the compound represented by formula (10) to convert the compound into a compound represented by formula (11). This step can be performed in the same manner as the method described in step 5.

Step 16:

This step is a step of condensing the compound represented by formula (11) with a compound represented by formula (1) to convert the compound into a compound represented by formula (12). This step can be performed in the same manner as the method described in step 6.

This step is considered to proceed via a compound represented by formula (30) and/or a compound represented by formula (31) as a reaction intermediate.

[Chem. 58]

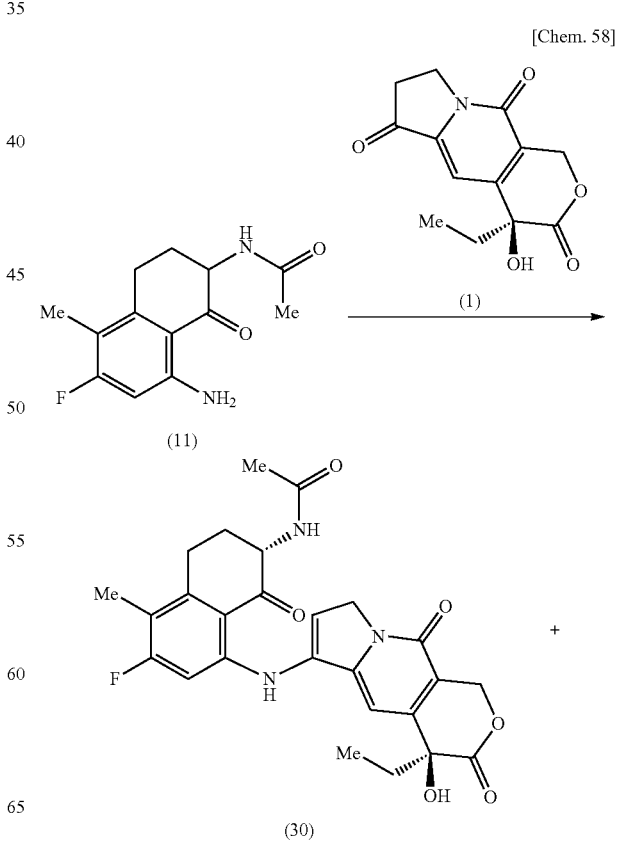

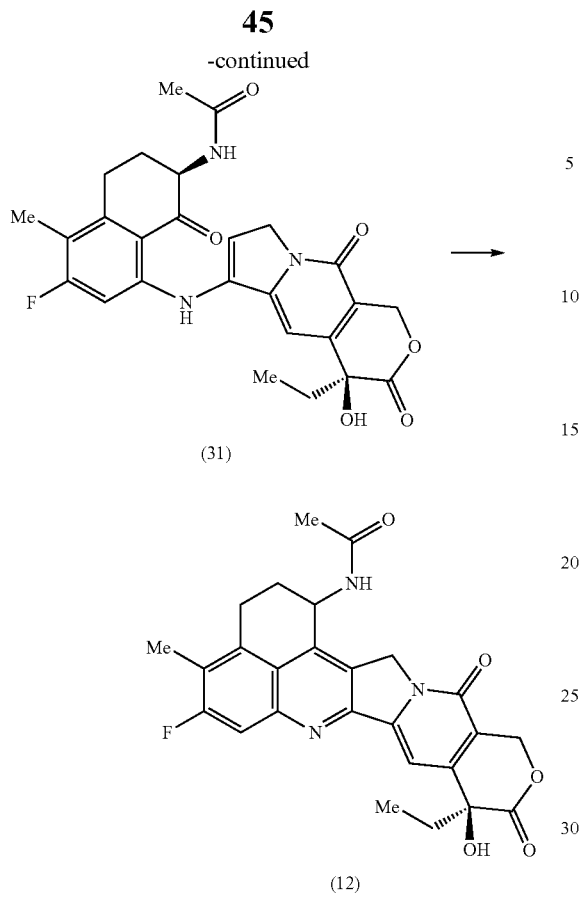
Step 17:
This step is a step of converting the compound represented by formula (12) into the compound represented by formula (2). This step can be performed in the same manner as the method described in step 7.
The compound represented by formula (2) can also be produced according to the following method.
[Chem. 59]
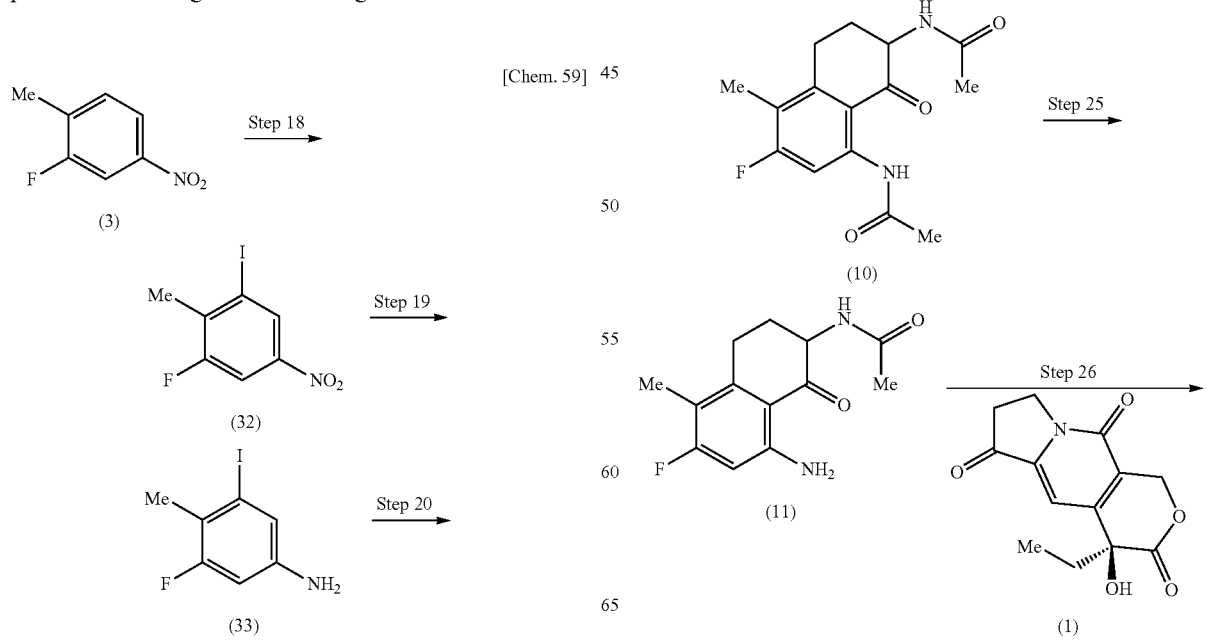

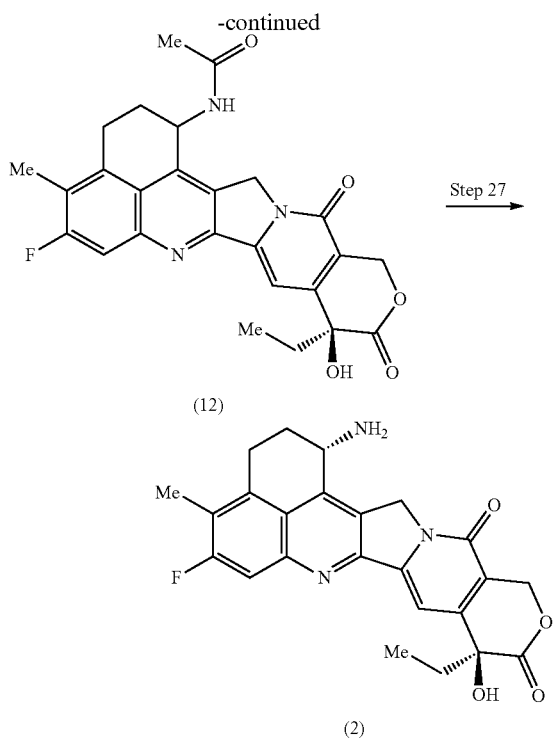

Step 18:

This step is a step of iodinating the compound represented by formula (3) to convert the compound into a compound represented by formula (32). As the compound represented by formula (3), a compound produced by a known method or a commercially available compound can be used.

The iodinating agent used in this step is not limited as long as the reaction proceeds, and examples include iodine and N-iodosuccinimide, and preferably N-iodosuccinimide. The amount of N-iodosuccinimide used in this step is not limited as long as the reaction proceeds, and is preferably 1 to 2 equivalents based on the compound represented by formula (3). This step can preferably be performed in a mixed solvent of sulfuric acid and a further solvent.

The further solvent is not particularly limited as long as it does not inhibit the reaction, and examples include dichloromethane, chloroform, diethyl ether, 1,2-dimethoxyethane, hexane, pentane, heptane, cyclohexane, ethylcyclohexane, benzene, toluene, chlorobenzene, and mixed solvents thereof, and preferably heptane.

The reaction temperature of this step is not limited as long as the reaction proceeds, and is preferably −10 to 10° C. The reaction time of this step is not limited as long as the reaction proceeds, and is preferably 1 to 4 hours.

Step 19:

This step is a step of reducing the nitro group of the compound represented by formula (32) to an amino group to convert the compound into a compound represented by formula (33). The reducing agent used in this step is not limited as long as it does not allow deiodination to proceed and is capable of selectively reducing only the nitro group, and preferably a platinum carbon catalyst can be used in the presence of hydrogen (preferably in a hydrogen stream of 0.05 to 0.2 MPa). The amount of the platinum carbon catalyst used in this step is not limited as long as the reaction proceeds, and is preferably 5 to 40% by weight based on the compound represented by formula (3) used in step 18. The solvent used in this step is not particularly limited as long as it does not inhibit the reaction, and examples include methanol, ethanol, 1,2-dimethoxyethane, tetrahydrofuran, 2-methyltetrahydrofuran, 1,4-dioxane, ethyl acetate, and water, and mixed solvents thereof, and preferably ethyl acetate. The reaction temperature of this step is not limited as long as the reaction proceeds, and is preferably 50 to 70° C. The reaction time of this step is not limited as long as the reaction proceeds, and is preferably 2 to 8 hours.

Step 20:

This step is a step of acetylating the amino group of the compound represented by formula (33) to convert the compound into a compound represented by formula (34). Examples of the acetylating agent used in this step include acetic anhydride and acetyl chloride, and preferably acetic anhydride. The amount of acetic anhydride used in this step is not limited as long as the reaction proceeds, and is preferably 0.5 to 1 equivalent based on the compound represented by formula (3) used in step 18. A base can preferably be used in this step. The base is not limited as long as the reaction proceeds, and is preferably triethylamine. The amount of the base is not limited as long as the reaction proceeds, and is preferably 0.75 to 1.5 equivalents based on the compound represented by formula (3) used in step 18. The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably ethyl acetate. The reaction temperature of this step is not limited as long as the reaction proceeds, and is preferably 10 to 40° C. The reaction time of this step is not limited as long as the reaction proceeds, and is preferably 3 to 12 hours.

Step 21:

This step is a step of coupling the compound represented by formula (34) with 3-butenoic acid to convert the compound into a compound represented by formula (7). This step can be performed in the same manner as the method described in step 1.

Step 22:

This step is a step of reducing the compound represented by formula (7) to convert the compound into a compound represented by formula (8).

This step can be performed in the same manner as step 12, but since the catalyst activity may be impaired by the residual iodide ions, this step is preferably performed with a larger amount of a catalyst and a higher hydrogen pressure than those in step 12.

The reduction in this step is not limited as long as the reaction proceeds, and can preferably be performed under a hydrogen atmosphere (preferably in a hydrogen stream of 0.15 to 0.6 MPa) using a palladium catalyst, a platinum catalyst, a nickel catalyst, a ruthenium catalyst, or a rhodium catalyst, more preferably can be performed using a palladium catalyst, and even more preferably can be performed using palladium carbon, and still more preferably 5% palladium carbon can be used. The amount of 5% palladium carbon used in this step is not limited as long as the reaction proceeds, and is preferably 20 to 160% by weight based on the compound represented by formula (34) used in step 21.

The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably 2-methyltetrahydrofuran.

The reaction temperature of this step is not limited as long as the reaction proceeds, and is preferably 20 to 60° C. The reaction time of this step is not limited as long as the reaction proceeds, and is preferably 4 to 16 hours.

Step 23:
This step is a step of subjecting the compound represented by formula (8) to intramolecular cyclization to convert the compound into a compound represented by formula (9). This step can be performed in the same manner as the method described in step 3.

Step 24:
This step is a step of converting the compound represented by formula (9) into a compound represented by formula (10). This step can be performed in the same manner as the method described in step 4.

Step 25:
This step is a step of selectively deprotecting the protecting group for the aromatic amino group of the compound represented by formula (10) to convert the compound into a compound represented by formula (11). This step can be performed in the same manner as the method described in step 5.

Step 26:
This step is a step of condensing the compound represented by formula (11) with the compound represented by formula (1) to convert the compound into a compound represented by formula (12). This step can be performed in the same manner as the method described in step 16.

Step 27:
This step is a step of converting the compound represented by formula (12) into the compound represented by formula (2). This step can be performed in the same manner as the method described in step 7.

In the reaction of each of the above steps, after completion of the reaction, the target compound of each step can be isolated from the reaction mixture according to a method well known in the field of organic chemistry. The target compound can be obtained by, for example, (i) filtering off insoluble matter such as a catalyst as necessary, (ii) adding water and a solvent that is immiscible with water (such as methylene chloride, diethyl ether, ethyl acetate, or 2-methyltetrahydrofuran) to the reaction mixture to extract the target compound, (iii) washing the organic layer with water and drying the organic layer using a desiccant such as anhydrous magnesium sulfate, and (iv) distilling off the solvent. While the resulting target compound can be further purified, as necessary, by a method well known in the field of organic chemistry (such as recrystallization, reprecipitation, silica gel column chromatography, or high performance liquid chromatography), preferably the production method of the present invention can be performed without using chromatography.

The compound represented by formula (2) obtained by the production method of the present invention can preferably be used to produce an antibody-drug conjugate in which the drug-linker represented by formula (15) is conjugated to an antibody via a thioether bond, but is not limited thereto, and the compound represented by formula (2) can also be used for the production of an antibody-drug conjugate having another chemical structure and for other applications.

[Production of Drug-Linker Intermediate]

The drug-linker intermediate preferably used in the production of the antibody-drug conjugate of the present invention is the compound represented by formula (14).

[Chem. 60]

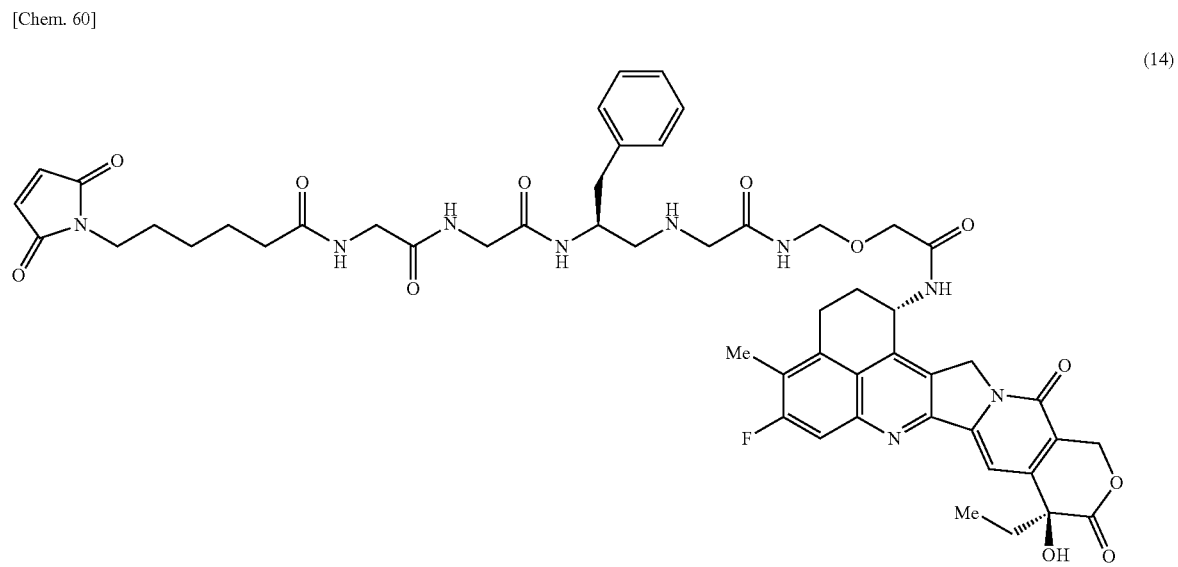

(14)

The compound represented by formula (14) can be produced as follows.

[Chem. 61]

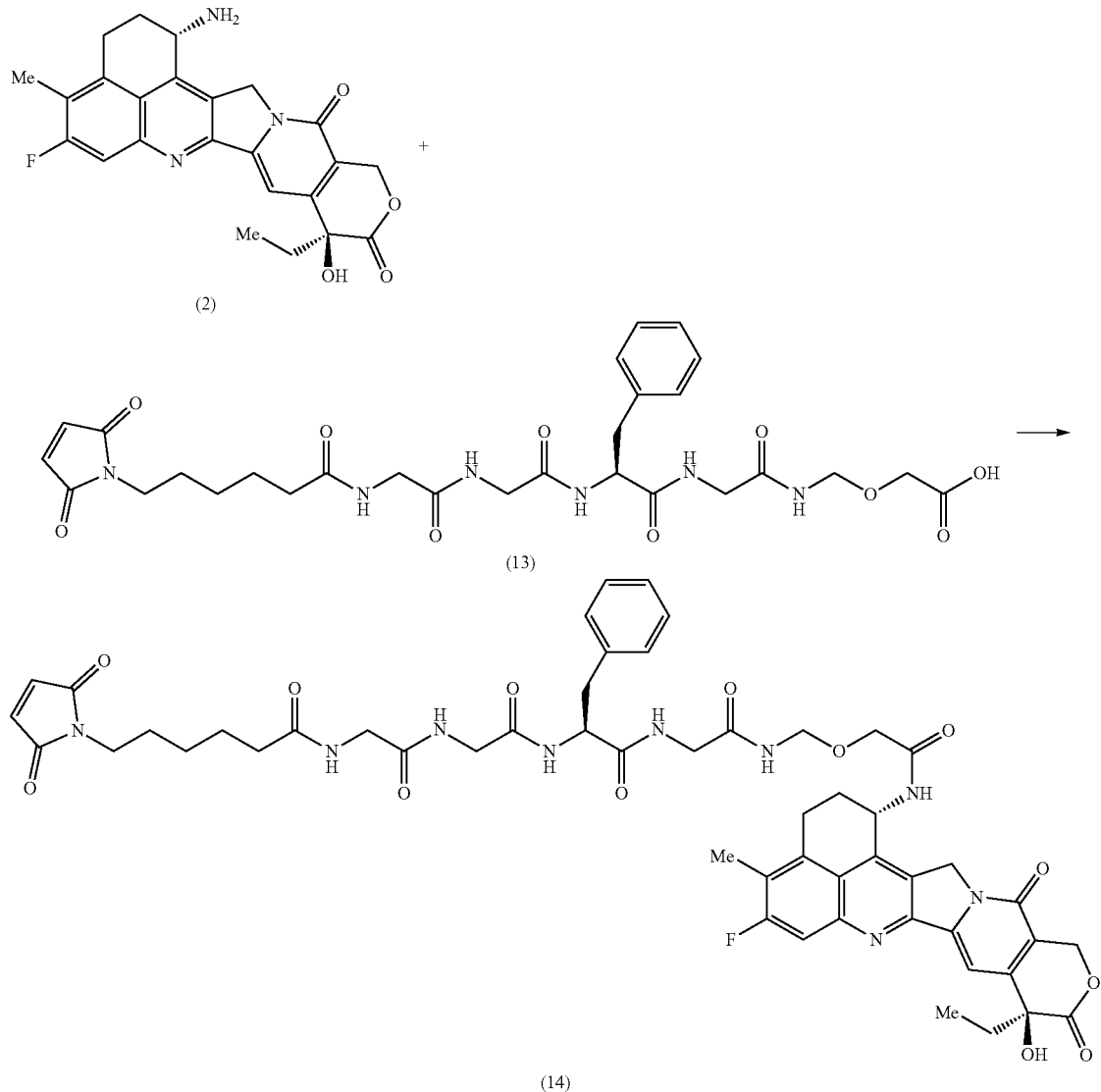

As the compound represented by formula (2), a compound produced by the production method of the present invention can be used. The compound represented by formula (13) can be produced with reference to descriptions in International Publication No. WO 2014/057687, International Publication No. WO 2015/098099, International Publication No. WO 2015/115091, and International Publication No. WO 2015/155998.

Conversion to the compound represented by formula (14) can be performed by derivatizing the compound represented by formula (13) to an active ester, a mixed acid anhydride, an acid halide, or the like, and reacting it with the compound represented by formula (2) preferably in the presence of a base.

An active ester can be produced by, for example, reacting the compound represented by formula (13) with a condensing agent such as N,N'-dicyclohexylcarbodiimide (DCC) or 1-ethyl-3-(3-dimethylaminopropyl)carbodiimide hydrochloride (WSCD-HCl), and an additive such as 1-hydroxy-benzotriazole (HOBt), 1-hydroxy-7-azabenzotriazole (HOAt), N-hydroxysuccinimide, or p-nitrophenol. The active ester can also be produced by reacting the compound represented by formula (13) with a condensing agent such as O-(7-azabenzotriazol-1-yl)-N,N,N',N'-tetramethyluronium hexafluorophosphate pentafluorophenyl trifluoroacetate (HATU), O-(benzotriazol-1-yl)-N,N,N',N'-tetramethyluronium hexafluorophosphate (HBTU), diethyl cyanophosphonate, or 4-(4,6-dimethoxy-1,3,5-triazin-2-yl)-4-methylmorpholinium chloride (DMTMM).

A mixed acid anhydride can be produced by, for example, reacting the compound represented by formula (13) with isobutyl chlorocarbonate, in the presence of a base as necessary.

A acid halide can be produced by treating the compound represented by formula (13) with an acid halide such as thionyl chloride or oxalyl chloride, in the presence of a base as necessary.

The base used in this step is not particularly limited as long as the reaction proceeds, and examples include organic bases such as triethylamine, tributylamine, diisopropylethylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, and 1,5-diazabicyclo[4.3.0]undec-7-ene, and inorganic bases such as potassium carbonate, potassium hydroxide, potassium hydrogen carbonate, sodium carbonate, sodium hydroxide, sodium hydrogen carbonate, sodium acetate, potassium acetate, sodium methoxide, sodium ethoxide, and potassium tert-butoxide; preferably triethylamine, tributylamine, diisopropylethylamine, potassium carbonate, potassium hydroxide, potassium hydrogen carbonate, sodium carbonate, sodium hydroxide, sodium hydrogen carbonate, sodium acetate, and potassium acetate; and more preferably triethylamine, diisopropylethylamine, and N-methylmorpholine.

The solvent used in this step is not particularly limited as long as it does not inhibit the reaction, and examples include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and preferably acetonitrile, dichloromethane, methanol, tetrahydrofuran, 1,4-dioxane, N,N-dimethylformamide, N,N-dimethylacetamide, 1-methyl-2-pyrrolidone, dimethyl sulfoxide, and water, and mixed solvents thereof.

[Production of Antibody]

An antibody for use in the production of the antibody-drug conjugate of the present invention may be derived from any species, and is preferably an antibody derived from a human, a rat, a mouse, or a rabbit. In cases where the antibody is derived from species other than human species, it is preferably chimerized or humanized using a well-known technique. The antibody of the present invention may be a polyclonal antibody or a monoclonal antibody and is preferably a monoclonal antibody.

The antibody for use in the production of the antibody-drug conjugate of the present invention is an antibody preferably having a characteristic of being capable of targeting cancer cells, and is preferably an antibody possessing, for example, the property of recognizing a cancer cell, the property of binding to a cancer cell, the property of internalizing in a cancer cell, and/or cytocidal activity against cancer cells.

The binding activity of the antibody against cancer cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added into the culture system at varying concentrations to determine inhibitory activity against focus formation, colony formation, and spheroid growth. The antitumor activity can be confirmed in vivo, for example, by administering the antibody to a nude mouse with a transplanted cancer cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against cancer cells, it is important and also preferred that the antibody should have the property of internalizing to migrate into cancer cells.

The antibody for use in the production of the antibody-drug conjugate of the present invention can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The antibody for use in the production of the antibody-drug conjugate of the present invention is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), an antibody obtained by grafting a part of the amino acid residues of the framework of a heterologous antibody as well as the CDR sequence of the heterologous antibody to a human antibody by a CDR-grafting method (International Publication No. WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002) 43 (7), p. 2301-2308; Carmen, S. et. al., Briefings in Functional Genomics and Proteomics (2002), 1(2), p. 189-203; Siriwardena, D. et. al., Ophthalmology (2002) 109(3), p. 427-431, etc.) can be exemplified.

In the present invention, modified variants of the antibody for use in the production of the antibody-drug conjugate of the present invention are also included. The modified variant refers to a variant obtained by subjecting the antibody according to the present invention to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present invention, for example, an enzyme-labeled antibody, a fluorescence-labeled antibody, and an affinity-labeled antibody are also included in the meaning of the modified variant. Such a modified variant of the antibody according to the present invention is useful for improving the stability and blood retention of the antibody, reducing the antigenicity thereof, detecting or isolating an antibody or an antigen, and so on.

Further, by regulating the modification of a glycan which is linked to the antibody according to the present invention (glycosylation, defucosylation, etc.), it is possible to enhance antibody-dependent cellular cytotoxic activity. As the technique for regulating the modification of a glycan of antibodies, International Publication No. WO 99/54342, International Publication No. WO 00/61739, International Publication No. WO 02/31140, etc. are known. However, the technique is not limited thereto. In the antibody according to the present invention, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variant having a deletion at the carboxyl terminus of the heavy chain of the antibody according to the present invention is not limited to the above variants as long as the antigen-binding affinity and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified.

As isotypes of the antibody according to the present invention, for example, IgG (IgG1, IgG2, IgG3, IgG4) can be exemplified, and IgG1 or IgG2 can be exemplified preferably.

Examples of antibodies applicable to the production of the antibody-drug conjugate of the present invention can include, but are not particularly limited to, an anti-HER2 antibody, an anti-HER3 antibody, an anti-TROP2 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, and an anti-GPR20 antibody, and preferably an anti-HER2 antibody, an anti-HER3 antibody, an anti-TROP2 antibody, an anti-B7-H3 antibody, and an anti-GPR20 antibody can be exemplified.

In the present invention, the term "anti-HER2 antibody" refers to an antibody which specifically binds to HER2 (Human Epidermal Growth Factor Receptor Type 2; ErbB-2), and preferably has an activity of internalizing in HER2-expressing cells by binding to HER2.

Examples of the anti-HER2 antibody include trastuzumab (U.S. Pat. No. 5,821,337) and pertuzumab (International Publication No. WO 01/00245), and trastuzumab can be preferably exemplified.

In the present invention, the term "trastuzumab" is a humanized anti-HER2 monoclonal antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

In the present invention, the term "anti-HER3 antibody" refers to an antibody which specifically binds to HER3

(Human Epidermal Growth Factor Receptor Type 3; ErbB-3), and preferably has an activity of internalizing in HER3-expressing cells by binding to HER3 on the surface of the HER3-expressing cells.

Examples of the anti-HER3 antibody include patritumab (U3-1287), U1-59 (International Publication No. WO 2007/077028), MM-121 (seribantumab), an anti-ERBB3 antibody described in International Publication No. WO 2008/100624, RG-7116 (lumretuzumab), and LJM-716 (elgemtumab), and patritumab and U1-59 can be preferably exemplified.

In the present invention, the term "anti-TROP2 antibody" refers to an antibody which specifically binds to TROP2 (TACSTD2: Tumor-associated calcium signal transducer 2; EGP-1), and preferably has an activity of internalizing in TROP2-expressing cells by binding to TROP2.

Examples of the anti-TROP2 antibody include hTINA1-H1L1 (International Publication No. WO 2015/098099).

In the present invention, the term "anti-B7-H3 antibody" refers to an antibody which specifically binds to B7-H3 (B cell antigen #7 homolog 3; PD-L3; CD276), and preferably has an activity of internalizing in B7-H3-expressing cells by binding to B7-H3.

Examples of the anti-B7-H3 antibody include M30-H1-L4 (International Publication No. WO 2014/057687).

In the present invention, the term "anti-GPR20 antibody" refers to an antibody which specifically binds to GPR20 (G protein-coupled receptor 20), and preferably has an activity of internalizing in GPR20-expressing cells by binding to GPR20.

Examples of the anti-GPR20 antibody include h046-H4e/L7 (International Publication No. WO 2018/135501).

[Conjugation Between the Antibody and the Drug-Linker Intermediate]

The antibody-drug conjugate according to the present invention can be produced by reacting a drug-linker intermediate (preferably the compound represented by formula (14)) and an antibody having a thiol group (alternatively referred to as a sulfhydryl group).

The antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl) phosphine hydrochloride (TCEP) per interchain disulfide within the antibody and reacting with the antibody in a buffer solution containing a chelating agent such as ethylenediamine tetraacetic acid (EDTA), an antibody having a sulfhydryl group with partially or completely reduced interchain disulfides within the antibody can be obtained.

Further, by using 2 to 20 molar equivalents of the drug-linker intermediate (preferably the compound represented by formula (14)) per antibody having a sulfhydryl group, an antibody-drug conjugate in which 2 to 8 drug molecules are conjugated per antibody molecule can be produced.

The average number of conjugated drug molecules per antibody molecule of the antibody-drug conjugate produced can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the antibody and the drug-linker intermediate and calculation of the average number of conjugated drug molecules per antibody molecule of the antibody-drug conjugate can be performed with reference to descriptions in International Publication No. WO 2014/057687, International Publication No. WO 2015/098099, International Publication No. WO 2015/115091, International Publication No. WO 2015/155998, International Publication No. WO 2018/135501, and so on.

In the present invention, the term "anti-HER2 antibody-drug conjugate" refers to an antibody-drug conjugate in which the antibody in the antibody-drug conjugate is an anti-HER2 antibody.

The anti-HER2 antibody is preferably an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2; or an antibody comprising a heavy chain consisting of the amino acid sequence represented by SEQ ID NO: 1 and a light chain consisting of the amino acid sequence represented by SEQ ID NO: 2.

The average number of units of the drug-linker conjugated per antibody molecule in the anti-HER2 antibody-drug conjugate produced by the present invention is preferably 2 to 8, more preferably 3 to 8, even more preferably 7 to 8, even more preferably 7.5 to 8, and even more preferably about 8.

The anti-HER2 antibody-drug conjugate can be produced with reference to descriptions in International Publication No. WO 2015/115091 by using a drug-linker intermediate (preferably the compound represented by formula (14)) produced by the production method of the present invention.

In the present invention, the term "anti-HER3 antibody-drug conjugate" refers to an antibody-drug conjugate in which the antibody in the antibody-drug conjugate is an anti-HER3 antibody.

The anti-HER3 antibody is preferably an antibody comprising a heavy chain consisting of the amino acid sequence represented by SEQ ID NO: 3 and a light chain consisting of the amino acid sequence represented by SEQ ID NO: 4, or a variant of the antibody in which a lysine residue at the carboxyl terminus of the heavy chain is deleted.

The average number of units of the drug-linker conjugated per antibody molecule in the anti-HER3 antibody-drug conjugate produced by the present invention is preferably 2 to 8, more preferably 3 to 8, even more preferably 7 to 8, even more preferably 7.5 to 8, and even more preferably about 8.

The anti-HER3 antibody-drug conjugate can be produced with reference to descriptions in International Publication No. WO 2015/155998 by using a drug-linker intermediate (preferably the compound represented by formula (14)) produced by the production method of the present invention.

In the present invention, the term "anti-TROP2 antibody-drug conjugate" refers to an antibody-drug conjugate in which the antibody in the antibody-drug conjugate is an anti-TROP2 antibody.

The anti-TROP2 antibody is preferably an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or a variant of the antibody in which a lysine residue at the carboxyl terminus of the heavy chain is deleted.

The average number of units of the drug-linker conjugated per antibody molecule in the anti-TROP2 antibody-drug conjugate produced by the present invention is preferably 2 to 8, more preferably 3 to 5, even more preferably 3.5 to 4.5, and even more preferably about 4.

The anti-TROP2 antibody-drug conjugate can be produced with reference to descriptions in International Publication No. WO 2015/098099 by using a drug-linker intermediate (preferably the compound represented by formula (14)) produced by the production method of the present invention.

In the present invention, the term "anti-B7-H3 antibody-drug conjugate" refers to an antibody-drug conjugate in which the antibody in the antibody-drug conjugate is an anti-B7-H3 antibody.

The anti-B7-H3 antibody is preferably an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or a variant of the antibody in which a lysine residue at the carboxyl terminus of the heavy chain is deleted.

The average number of units of the drug-linker conjugated per antibody molecule in the anti-B7-H3 antibody-drug conjugate produced by the present invention is preferably 2 to 8, more preferably 3 to 5, even more preferably 3.5 to 4.5, and even more preferably about 4.

The anti-B7-H3 antibody-drug conjugate can be produced with reference to descriptions in International Publication No. WO 2014/057687 by using a drug-linker intermediate (preferably the compound represented by formula (14)) produced by the production method of the present invention.

In the present invention, the term "anti-GPR20 antibody-drug conjugate" refers to an antibody-drug conjugate in which the antibody in the antibody-drug conjugate is an anti-GPR20 antibody.

The anti-GPR20 antibody is preferably an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10, or a variant of the antibody in which a lysine residue at the carboxyl terminus of the heavy chain is deleted.

The average number of units of the drug-linker conjugated per antibody molecule in the anti-GPR20 antibody-drug conjugate produced by the present invention is preferably 2 to 8, more preferably 3 to 8, even more preferably 7 to 8, even more preferably 7.5 to 8, and even more preferably about 8.

The anti-GPR20 antibody-drug conjugate can be produced with reference to descriptions in International Publication No. WO 2018/135501 by using a drug-linker intermediate (preferably the compound represented by formula (14)) produced by the production method of the present invention.

[Pharmaceutical Compositions]

The antibody-drug conjugate produced by the present invention can contain at least one pharmaceutically suitable ingredient and be administered. The pharmaceutically suitable ingredient can be suitably selected and applied from formulation additives or the like that are generally used in the art according to the dosage, administration concentration, and so on of the antibody-drug conjugate produced by the present invention. For example, the antibody-drug conjugate produced by the present invention can be administered as a pharmaceutical composition containing a buffer such as a histidine buffer, an excipient such as sucrose or trehalose, and a surfactant such as polysorbate 80 or polysorbate 20.

The pharmaceutical composition containing the antibody-drug conjugate produced by the present invention can be expected to exert a therapeutic effect by application as a systemic therapy to patients, and additionally, by local application to cancer tissues.

The pharmaceutical composition containing the antibody-drug conjugate produced by the present invention can be preferably used for a mammal, and can be more preferably used for a human.

The pharmaceutical composition containing the antibody-drug conjugate produced by the present invention can be preferably used as an injection, can be more preferably used as an aqueous injection or a lyophilized injection, and can be even more preferably used as a lyophilized injection.

In the case that the pharmaceutical composition containing the antibody-drug conjugate produced by the present invention is an aqueous injection, preferably it can be diluted with a suitable diluent and then intravenously administered by drip infusion. Examples of the diluent include glucose solution (preferably a 5% glucose solution) and physiological saline.

In the case that the pharmaceutical composition containing the antibody-drug conjugate produced by the present invention is a lyophilized injection, preferably it can be dissolved in water for injection, and then, a necessary amount can be diluted with a suitable diluent and then intravenously administered by drip infusion. Examples of the diluent include a glucose solution (preferably a 5% glucose solution) and physiological saline.

Examples of administration routes that can be used for administering the pharmaceutical composition containing the antibody-drug conjugate produced by the invention can include intravenous, intradermal, subcutaneous, intramuscular, and intraperitoneal routes, and intravenous route can be preferably exemplified.

The antibody-drug conjugate produced by the present invention can be administered to a human at intervals of once a day to every 180 days, preferably can be administered at intervals of once a week, every 2 weeks, every 3 weeks, or every 4 weeks, and even more preferably can be administered at intervals of once every 3 weeks. Also, the antibody-drug conjugate produced by the present invention can be administered at a dosage of about 0.001 to 100 mg/kg per dose, and preferably administered at a dosage of 0.8 to 12.4 mg/kg per dose. In the case that the antibody-drug conjugate produced by the present invention is an anti-HER2 antibody-drug conjugate, it can be preferably administered at a dosage of 5.4, 6.4, or 7.4 mg/kg per dose, and more preferably can be administered at a dosage of 5.4 mg/kg or 6.4 mg/kg per dose.

The pharmaceutical composition containing the antibody-drug conjugate produced by the present invention can be used for treating cancer, and can be preferably used for treating at least one type of cancer selected from the group consisting of breast cancer, stomach cancer (also called gastric adenocarcinoma), colorectal cancer (also called colon and rectal cancer, and including colon cancer and rectal cancer), lung cancer (including small cell lung cancer and non-small cell lung cancer), esophageal cancer, salivary gland cancer, esophagogastric junction adenocarcinoma, bile duct cancer, Paget's disease, pancreatic cancer, ovarian cancer, uterine carcinosarcoma, urothelial cancer, prostate cancer, bladder cancer, gastrointestinal stromal tumor, digestive tract stromal tumor, cervical cancer, squamous cell carcinoma, peritoneal cancer, liver cancer, hepatocellular cancer, colon cancer, rectal cancer, endometrial cancer, uterine cancer, kidney cancer, vulvar cancer, thyroid cancer, penile cancer, leukemia, malignant lymphoma, plasmacytoma, myeloma, neuroepithelial tumor, nerve sheath tumor, head-and-neck cancer, skin cancer, pharyngeal cancer, gallbladder cancer, bile duct cancer, mesothelioma, and sarcoma. For example, when the antibody-drug conjugate produced by the present invention is an anti-HER2 antibody-drug conjugate, the antibody-drug conjugate can be more preferably used for treating at least one type of cancer selected from the group consisting of breast cancer, stomach cancer, colorectal cancer, non-small cell lung cancer, esophageal cancer, salivary gland cancer, esophagogastric junction adenocarcinoma, bile duct cancer, Paget's disease, pancreatic cancer, ovarian cancer, and uterine carcinosarcoma, can be more preferably used for treating at least one type of cancer selected from the group consisting of breast cancer, stomach cancer, colorectal cancer, non-small cell lung cancer, esophageal cancer, salivary gland cancer, gastroesophageal junction adenocarcinoma, bile duct cancer, and Paget's disease, and can be even more preferably used for treating breast cancer, stomach cancer, colorectal cancer, or non-small cell lung cancer.

The pharmaceutical composition containing the antibody-drug conjugate produced by the present invention can be selectively used as an agent for drug therapy, which is a main method for treating cancer, and as a result, can delay development of cancer cells, inhibit growth thereof, and further kill cancer cells. These effects can allow cancer patients to be free from symptoms caused by cancer or achieve improvement in QOL of cancer patients and attain a therapeutic effect by sustaining the lives of the cancer patients. Even if the pharmaceutical composition and therapeutic method of the present invention do not accomplish killing cancer cells, they can achieve higher QOL of cancer patients while achieving longer-term survival, by inhibiting or controlling the growth of cancer cells.

In such drug therapy, the pharmaceutical composition containing the antibody-drug conjugate produced by the present invention can be used as an agent alone and, in addition, can also be used in combination with an additional therapy in adjuvant therapy and can be combined with surgery, radiotherapy, hormone therapy, or the like. Furthermore, the pharmaceutical composition can also be used as drug therapy in neoadjuvant therapy.

In addition to the therapeutic use as described above, for example, a prophylactic effect such as suppressing the growth of small metastatic cancer cells and further killing them can also be expected for the pharmaceutical composition containing the antibody-drug conjugate produced by the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The pharmaceutical composition containing the antibody-drug conjugate produced by the present invention can be administered in combination with other cancer treating agents. The anti-cancer effect may be enhanced accordingly. Examples of other cancer treating agents used in such purposes include 5-fluorouracil (5-FU), pertuzumab, trastuzumab, paclitaxel, carboplatin, cisplatin, gemcitabine, capecitabine, irinotecan (CPT-11), docetaxel, pemetrexed, sorafenib, vinblastin, vinorelbine, everolimus, tanespimycin, bevacizumab, oxaliplatin, lapatinib, trastuzumab emtansine (T-DM1) or agents described in International Publication No. WO 2003/038043, LH-RH analogues (leuprorelin, goserelin, or the like), estramustine phosphate, estrogen antagonists (tamoxifen, raloxifene, or the like), and aromatase inhibitors (anastrozole, letrozole, exemestane, and the like), but are not limited as long as they are agents having an antitumor activity.

EXAMPLES

The present invention is described in more detail below by way of examples. However, the present invention is not limited to these.

In the Examples, the terms "$^1$H-NMR" and "$^{13}$C-NMR" mean "nuclear magnetic resonance spectrum". Within parentheses, CDCl$_3$ means deuterated chloroform which is a measuring solvent, DMSO-d$_6$ means deuterated dimethyl sulfoxide which is a measuring solvent, and D$_2$O means deuterium oxide which is a measuring solvent. TMS (tetramethylsilane) was used as an internal standard. The meanings of multiplicity in 1H-NMR are s=singlet, d=doublet, t=triplet, q=quartet, quint=quintet, m=multiplet, and brs=broad singlet.

Example 1

N-(3-Bromo-5-fluoro-4-methylphenyl)acetamide

[Chem. 62]

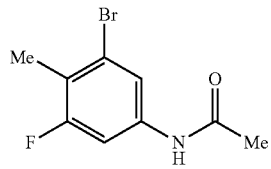

(6)

A solution of 2-fluoro-1-methyl-4-nitrobenzene (10.0 g, 64.5 mmol) in concentrated sulfuric acid (90% or more, 50 mL) and heptane (50 mL) was heated to about 60° C., and then N-bromosuccinimide (13.8 g, 77.4 mmol) was added in six divided portions. The mixture was stirred at about 60° C. for 1 hour and then cooled to room temperature. The resulting reaction solution was added to cold water (50 mL). After toluene (50 mL) was added for separation, the aqueous layer was removed. Then, the organic layer was washed with water (50 mL), a 6.5 wt % aqueous sodium hydrogencarbonate solution (50 mL), and a 5 wt % aqueous sodium sulfite solution (50 mL). Water (50 mL) and activated carbon (1.0 g) were added to the resulting aqueous layer, the mixture was stirred for 1 hour at room temperature, and then insoluble matter was separated by filtration and washed with toluene (20 mL). After the aqueous layer was removed from the filtrate, the organic layer was concentrated under reduced pressure. Ethyl acetate (100 mL) was added to the concentrated residue (about 30 mL), and the mixture was concentrated again under reduced pressure to give a solution of 1-bromo-3-fluoro-2-methyl-5-nitrobenzene in ethyl acetate (about 30 mL).

A suspension was obtained by adding a 1% platinum carbon catalyst (2.0 g) and ethyl acetate (120 mL) to the solution of 1-bromo-3-fluoro-2-methyl-5-nitrobenzene in ethyl acetate (about 30 mL) and the atmosphere was replaced with nitrogen and then replaced with hydrogen. The mixture was stirred at about 60° C. for 4 hours in a hydrogen stream (0.1 MPa) and cooled to room temperature. Insoluble matter was separated by filtration from the resulting suspension, and the insoluble matter was washed with ethyl acetate (30 mL). The filtrate was washed twice with a 0.5 N hydrochloric acid solution (100 mL) to give an organic layer. The aqueous layer at this time was extracted with ethyl acetate (50 mL) to give an organic layer, and the organic layers were combined. Then, the organic layer was washed with a 6.5 wt % aqueous sodium hydrogencarbonate solution (50 mL) and 5 wt % brine (50 mL), and the resulting organic layer was concentrated under reduced pressure. Ethyl acetate (50 mL) was added to the concentrated residue (about 30 mL), and the mixture was concentrated again under reduced pressure to give a solution of 3-bromo-5-fluoro-4-methylaniline in ethyl acetate (about 30 mL).

Triethylamine (7.2 mL, 51.8 mmol) and acetic anhydride (3.3 mL, 34.4 mmol) were added to a solution obtained by adding ethyl acetate (30 mL) to the solution of 3-bromo-5-fluoro-4-methylaniline in ethyl acetate (about 29 mL), and the mixture was stirred at room temperature for 6 hours. After 10 wt % brine (50 mL) was added to the resulting reaction solution for separation, the aqueous layer was removed. The resulting organic layer was concentrated under reduced pressure, then ethyl acetate (50 mL) was added, and the mixture was concentrated again under reduced pressure. Ethyl acetate (80 mL) was added to the concentrated residue (about 30 mL), a 4 N hydrochloric acid/ethyl acetate solution (10.9 mL, 43.7 mmol) was added, and then the mixture was stirred at room temperature for 1 hour. Insoluble matter was separated by filtration and washed with ethyl acetate (40 mL). After 10 wt % brine (40 mL) was added to the filtrate, a 25 wt % aqueous sodium hydroxide solution (5.6 g) was added to regulate the pH to about 7. After the aqueous layer was removed, the organic layer was concentrated under reduced pressure. Toluene (100 mL) was added to the concentrated residue (about 30 mL), and the concentrated residue (about 30 mL) concentrated under reduced pressure was stirred at 50° C. for 5 hours and then cooled to room temperature. The mixture was stirred at room temperature for 12 hours, then cooled to 3° C., and stirred for 2 hours. The precipitated crystals were collected by filtration and washed with cold toluene (20 mL) and 75% cold aqueous acetonitrile (20 mL). The resulting crystals were dried at 40° C. under reduced pressure to give N-(3-bromo-5-fluoro-4-methylphenyl)acetamide as white crystals (5.7 g, yield 37%).

$^1$H-NMR (500 MHz, CDCl$_3$) δ 7.41 (1H, s), 7.39 (1H, d, J=9.2 Hz), 7.20 (1H, brs), 2.27 (3H, d, J=2.0 Hz), 2.17 (3H, s)

Example 2

4-[5-(Acetylamino)-3-fluoro-2-methylphenyl]butanoic acid

[Chem. 63]

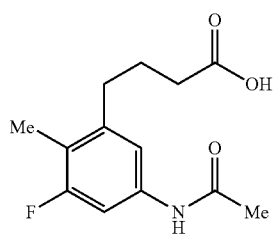

(8)

A solution of N-(3-bromo-5-fluoro-4-methylphenyl)acetamide (30.0 g, 121.9 mmol), 3-butenoic acid (12.4 mL, 146.3 mmol), and diisopropylethylamine (46.0 mL, 268.2 mmol) in tetrahydrofuran (120 mL) and water (30 mL) was degassed under reduced pressure and the atmosphere was replaced with nitrogen, and then tri(o-tolyl)phosphine (1.1 g, 3.7 mmol) was added. Again the mixture was degassed under reduced pressure and the atmosphere was replaced with nitrogen, then palladium(II) acetate (0.4 g, 1.8 mmol) was added, and the mixture was degassed under reduced pressure, the atmosphere was replaced with nitrogen, and then thermally refluxed for 5 hours. Activated carbon (3.0 g) was added to the reaction solution that had been cooled to room temperature, and the mixture was stirred at room temperature for 1 hour. Insoluble matter was separated by filtration and washed with 20% aqueous tetrahydrofuran (60 mL). 2-Methyltetrahydrofuran (300 mL) and water (300 mL) were added to the filtrate, and a 25 wt % aqueous sodium hydroxide solution (23.4 g, 146.3 mmol) was added. The organic layer was removed, 2-methyltetrahydrofuran (300 mL) and concentrated hydrochloric acid (36%, 22.2 g, 219.4 mmol) were added to the aqueous layer, and then sodium chloride (30 g) was added. After separation, the aqueous layer was removed, and the organic layer was washed with 10 wt % brine (90 mL). The resulting organic layer was concentrated under reduced pressure to give a solution of 4-[5-(acetylamino)-3-fluoro-2-methylphenyl]-3-butenoic acid containing geometric isomers in 2-methyltetrahydrofuran (about 150 mL).

A suspension was obtained by adding 2-methyltetrahydrofuran (308 mL) and 5% palladium carbon (5.6 g) to the solution of 4-[5-(acetylamino)-3-fluoro-2-methylphenyl]-3-butenoic acid containing geometric isomers in 2-methyltetrahydrofuran (about 140 mL) and the atmosphere was replaced with nitrogen and then replaced with hydrogen. The mixture was stirred at about 40° C. for 1 hour in a hydrogen stream (0.1 MPa) and cooled to room temperature. Insoluble matter was separated by filtration from the resulting suspension and washed with 2-methyltetrahydrofuran (112 mL). Water (140 mL) was added to the filtrate, and the pH was regulated to about 2 with a 1 N hydrochloric acid solution. After separation, the aqueous layer was removed, and the resulting organic layer was concentrated under reduced pressure. Ethyl acetate (420 mL) was added to the concentrated residue, and the mixture was concentrated under reduced pressure. Again, ethyl acetate (420 mL) was added, and the mixture was concentrated under reduced pressure to give a concentrated residue (about 170 mL). After the concentrated residue was stirred at 50° C. for 5 hours, heptane (140 mL) was added, and the mixture was cooled to room temperature. The precipitated crystals were collected by filtration and washed with ethyl acetate/heptane (3/7) (84 mL). The resulting crystals were dried under reduced pressure to give 4-[5-(acetylamino)-3-fluoro-2-methylphenyl]butanoic acid as white crystals (26.1 g, yield 91%).

$^1$H-NMR (500 MHz, DMSO-d$_6$) δ 12.08 (1H, brs), 9.97 (1H, s), 7.42 (1H, dd, J=12.5, 2.0 Hz), 7.05 (1H, d, J=1.5 Hz), 2.59-2.54 (2H, m), 2.28 (2H, t, J=7.3 Hz), 2.10 (3H, d, J=2.0 Hz), 2.02 (3H, s), 1.71 (2H, quint, J=7.5 Hz)

Example 3-1

N-(3-Fluoro-4-methyl-8-oxo-5,6,7,8-tetrahydronaphthalen-1-yl)acetamide

[Chem. 64]

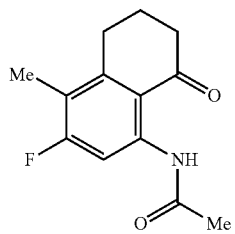

(9)

After a solution of 4-[5-(acetylamino)-3-fluoro-2-methylphenyl]butanoic acid (12.0 g, 47.4 mmol) and trifluoroacetic acid (24 mL) was cooled to 4° C., trifluoroacetic anhydride (13.4 mL, 94.8 mmol) was added dropwise, and the mixture was stirred at about 4° C. for 4 hours. The resulting reaction solution was added dropwise to 50% aqueous acetonitrile (120 mL) that had been cooled to 5° C. After the pH was regulated to about 7 with a 25 wt % aqueous sodium hydroxide solution (77.3 g), water (59 mL) was added. Then, the temperature was returned to room temperature, and the precipitated crystals were collected by filtration and washed with water (60 mL) and 75% aqueous acetonitrile (60 mL). The resulting crystals were dried under reduced pressure to give N-(3-fluoro-4-methyl-8-oxo-5,6,7,8-tetrahydronaphthalen-1-yl)acetamide as pale yellowish white crystals (10.2 g, yield 92%).

$^1$H-NMR (400 MHz, CDCl$_3$) δ 12.31 (1H, brs), 8.43 (1H, d, J=12.8 Hz), 2.88 (2H, t, J=12.0 Hz), 2.66 (2H, dd, J=7.2, 6.0 Hz), 2.22 (3H, s), 2.17 (3H, d, J=2.0 Hz), 2.09 (3H, quint, J=6.4 Hz)

Example 3-2

N-(3-Fluoro-4-methyl-8-oxo-5,6,7,8-tetrahydronaphthalen-1-yl)acetamide

[Chem. 65]

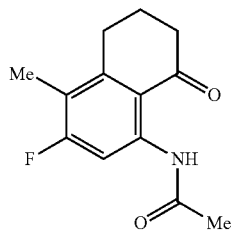

(9)

After a solution of 4-[5-(acetylamino)-3-fluoro-2-methylphenyl]butanoic acid (5.0 g, 19.7 mmol) and trifluoroacetic acid (10 mL) was cooled to 2° C., trifluoroacetic anhydride (5.6 mL, 39.5 mmol) was added dropwise, and the mixture was stirred at about 5° C. for 3 hours. To the reaction solution 50% aqueous acetonitrile (50 mL) was added dropwise. After the pH was regulated to about 7 with a 25 w/v % aqueous sodium hydroxide solution (33 mL), water (17 mL) was added. Then, the temperature was returned to room temperature, and the precipitated crystals were collected by filtration and washed with water (25 mL) and 75% aqueous acetonitrile (25 mL). The resulting crystals were dried under reduced pressure to give N-(3-fluoro-4-methyl-8-oxo-5,6,7,8-tetrahydronaphthalen-1-yl)acetamide as pale yellowish white crystals (4.3 g, yield 92%).

Example 3-3

N-(3-Fluoro-4-methyl-8-oxo-5,6,7,8-tetrahydronaphthalen-1-yl)acetamide

[Chem. 66]

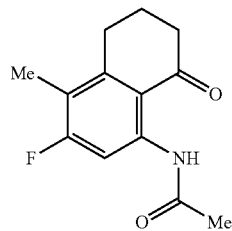

(9)

After a solution of 4-[5-(acetylamino)-3-fluoro-2-methylphenyl]butanoic acid (5.0 g, 19.7 mmol) and trifluoroacetic acid (10 mL) was cooled to 2° C., trifluoroacetic anhydride (5.6 mL, 39.5 mmol) was added dropwise, and the mixture was stirred at about 5° C. for 4 hours. To the reaction solution, 17% aqueous acetonitrile (30 mL) was added dropwise, and then water (20 mL) was added dropwise. After the pH was regulated to about 7 with a 25 w/v % aqueous sodium hydroxide solution (33 mL), water (17 mL) was added. Then, the temperature was returned to room temperature, and the precipitated crystals were collected by filtration and washed with water (25 mL) and 75% aqueous acetonitrile (25 mL). The resulting crystals were dried under reduced pressure to give N-(3-fluoro-4-methyl-8-oxo-5,6,7,8-tetrahydronaphthalen-1-yl)acetamide as pale yellowish white crystals (4.3 g, yield 93%).

Example 4-1

N,N'-(3-Fluoro-4-methyl-8-oxo-5,6,7,8-tetrahydronaphthalen-1,7-diyl)diacetamide

[Chem. 67]

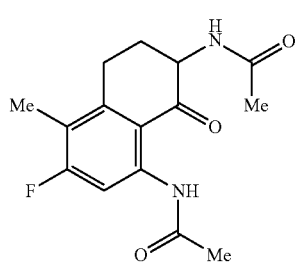

(10)

A solution of N-(3-fluoro-4-methyl-8-oxo-5,6,7,8-tetrahydronaphthalen-1-yl)acetamide (5.0 g, 21.3 mmol) in tetrahydrofuran (75 mL) was cooled to 6° C., and amyl nitrite (3.7 mL, 27.6 mmol) and potassium tert-butoxide (2.9 g, 25.5 mmol) were added. After the mixture was stirred at 3° C. for 17 hours, acetic acid (25 mL) and acetic anhydride (25 mL) were added, and then the temperature was raised. At about 20° C., a 2% platinum carbon catalyst (1.5 g) was added, and the atmosphere of the mixture was replaced with nitrogen and then replaced with hydrogen. The mixture was stirred at room temperature for 4 hours in a hydrogen stream (0.3 MPa). Insoluble matter was separated by filtration from the resulting suspension, and washed with ethyl acetate (25 mL). Activated carbon (0.7 g) was added to the filtrate, the mixture was stirred at room temperature for 1 hour, and then insoluble matter was separated by filtration and washed with ethyl acetate (25 mL). The filtrate was cooled to 1° C., and a 5 N aqueous sodium hydroxide solution (50 mL) was added dropwise. The aqueous layer was removed, and a 5 N aqueous sodium hydroxide solution (50 mL) was added again to remove the aqueous layer. After tetrahydrofuran (35 mL) and water (25 mL) were added to the resulting organic layer, a 5 N aqueous sodium hydroxide solution (25 mL) was added to regulate the pH to about 7. After the temperature was raised to room temperature, the aqueous layer was removed, and the organic layer was washed with 10 wt % brine (25 mL). The resulting organic layer was concentrated under reduced pressure to give a concentrated residue. Ethyl acetate (50 mL) was added to the concentrated residue, and the mixture was concentrated under reduced pressure. The concentrated residue (about 25 mL) that had undergone this operation a total of three times was stirred at 40° C. for 5 hours, then cooled to room temperature, and stirred at 2° C. for 3 hours. The precipitated crystals were collected by filtration and washed with cold ethyl acetate (25 mL) and water (25 mL). The resulting crystals were dried under reduced pressure to give N,N'-(3-fluoro-4-methyl-8-oxo-5,6,7,8-tetrahydronaphthalen-1,7-diyl)diacetamide as white crystals (3.7 g, yield 60%).

$^1$H-NMR (500 MHz, CDCl$_3$) δ 11.76 (1H, s), 8.43 (1H, d, J=13.0 Hz), 6.53 (1H, d, J=4.5 Hz), 4.62 (1H, dt, J=14.0, 5.4 Hz), 3.08-2.96 (2H, m), 2.78-2.72 (1H, m), 2.23 (3H, s), 2.15 (3H, d, J=1.5 Hz), 2.11 (3H, s), 1.88-1.77 (1H, m)

Example 4-2

N,N'-(3-Fluoro-4-methyl-8-oxo-5,6,7,8-tetrahydronaphthalen-1,7-diyl)diacetamide

[Chem. 68]

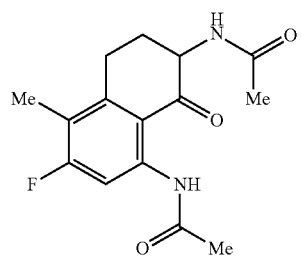

(10)

A solution of N-(3-fluoro-4-methyl-8-oxo-5,6,7,8-tetrahydronaphthalen-1-yl)acetamide (35.0 g, 148.8 mmol) in tetrahydrofuran (525 mL) was cooled to 4° C., and amyl nitrite (25.7 mL, 193.4 mmol) and potassium tert-butoxide (20.0 g, 178.6 mmol) were added. After the mixture was stirred at 1° C. for 17 hours, acetic acid (175 mL) and acetic anhydride (175 mL) were added, and then the temperature was raised. At about 20° C., a 2% platinum carbon catalyst (11.8 g) was added, and the atmosphere of the mixture was replaced with nitrogen and then replaced with hydrogen. The mixture was stirred at room temperature for 3 hours in a hydrogen stream (0.3 MPa). Insoluble matter was separated by filtration from the resulting suspension, and the insoluble matter was washed with ethyl acetate (175 mL). Activated carbon (5.3 g) was added to the filtrate, the mixture was stirred at room temperature for 2 hour, and then insoluble matter was separated by filtration and washed with ethyl acetate (175 mL). The filtrate was cooled to 1° C., and a 5 N aqueous sodium hydroxide solution (350 mL) was added dropwise. The aqueous layer was removed, a 5 N aqueous sodium hydroxide solution (350 mL) was added again to remove the aqueous layer. After tetrahydrofuran (245 mL) and water (175 mL) were added to the resulting organic layer, a 5 N aqueous sodium hydroxide solution (150 mL) was added to regulate the pH to about 7. After the temperature was raised to room temperature, the aqueous layer was removed, and the organic layer was washed with 10 wt % brine (175 mL). The resulting organic layer was concentrated under reduced pressure to give a concentrated residue. Ethyl acetate (350 mL) was added to the concentrated residue, and the mixture was concentrated under reduced pressure. The concentrated residue (about 175 mL) that had undergone this operation a total of three times was stirred at 40° C. for 5 hours, then cooled to room temperature, and stirred at 2° C. for 3 hours. The precipitated crystals were collected by filtration and washed with cold ethyl acetate (175 mL) and water (175 mL). The resulting crystals were dried under reduced pressure to obtain white crystals (25.1 g).

A suspension of the obtained crystals (24.0 g, 82.1 mmol) in 20% aqueous ethanol (300 mL) was heated to 65° C. Activated carbon (4.8 g) was added, the mixture was stirred for 30 minutes at 70° C., then insoluble matter was separated by filtration and washed with 20% aqueous ethanol (72 mL). After water (300 mL) at 60° C. was added dropwise to the filtrate, the mixture was annealed to 2° C. and stirred for 2 hours. The precipitated crystals were collected by filtration and washed with cold 60% aqueous ethanol (120 mL). The resulting crystals were dried under reduced pressure to give N,N'-(3-fluoro-4-methyl-8-oxo-5,6,7,8-tetrahydronaphthalen-1,7-diyl)diacetamide as white crystals (21.6 g, yield 52%).

$^1$H-NMR (500 MHz, CDCl$_3$) δ 11.76 (1H, s), 8.43 (1H, d, J=13.0 Hz), 6.53 (1H, d, J=4.5 Hz), 4.62 (1H, dt, J=14.0, 5.4 Hz), 3.08-2.96 (2H, m), 2.78-2.72 (1H, m), 2.23 (3H, s), 2.15 (3H, d, J=1.5 Hz), 2.11 (3H, s), 1.88-1.77 (1H, m)

Example 4-3

N,N'-(3-Fluoro-4-methyl-8-oxo-5,6,7,8-tetrahydronaphthalen-1,7-diyl)diacetamide

[Chem. 69]

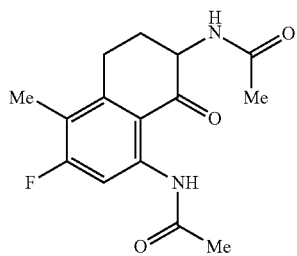

(10)

A solution of N-(3-fluoro-4-methyl-8-oxo-5,6,7,8-tetrahydronaphthalen-1-yl)acetamide (3.0 g, 12.8 mmol) in tetrahydrofuran (45 mL) was cooled to 0° C., and amyl nitrite (2.2 mL, 16.6 mmol) and potassium tert-butoxide (1.7 g, 15.3 mmol) were added. After the mixture was stirred at 3° C. for 3 hours, acetic acid (15 mL) and acetic anhydride (15 mL) were added, the temperature was raised to 20° C., and the mixture was stirred for 1.5 hours. At about 3° C., a 5% platinum carbon catalyst (0.4 g) was added, and the atmosphere of the mixture was replaced with nitrogen and then replaced with hydrogen. The mixture was stirred at about 5° C. for 3 hours in a hydrogen stream (0.6 MPa). Then, the mixture was stirred at about 30° C. for 1 hour, and insoluble matter was separated by filtration, and the insoluble matter was washed with ethyl acetate (15 mL). Activated carbon (0.5 g) was added to the filtrate, the mixture was stirred at room temperature for 2 hours, and then insoluble matter was separated by filtration and washed with ethyl acetate (15 mL). The filtrate was cooled to about 5° C., and a 5 N aqueous sodium hydroxide solution (30 mL) was added dropwise. The aqueous layer was removed, tetrahydrofuran (30 mL) and a 5 N aqueous sodium hydroxide solution (30 mL) were added to remove the aqueous layer. After water (15 mL) was added to the resulting organic layer, a 5 N aqueous sodium hydroxide solution (15 mL) was added to regulate the pH to about 7. After the temperature was raised to room temperature, the aqueous layer was removed, and the organic layer was washed with 10 wt % brine (15 mL). The resulting organic layer was concentrated under reduced pressure to give a concentrated residue. Ethyl acetate (30 mL) was added to the concentrated residue, and the mixture was concentrated under reduced pressure. The concentrated residue (about 15 mL) that had undergone this operation a total of three times was stirred at 40° C. for 5 hours, cooled to room temperature, and stirred at 5° C. for 2 hours or longer. The precipitated crystals were collected by filtration and washed with cold ethyl acetate (15 mL) and water (15 mL). The resulting crystals were dried under reduced pressure to give N,N'-(3-fluoro-4-methyl-8-oxo-5,6,7,8-tetrahydronaphthalen-1,7-diyl)diacetamide as white crystals (2.3 g, yield 62%).

Example 5-1

N-(8-Amino-6-fluoro-5-methyl-1-oxo-1,2,3,4-tetrahydronaphthalen-2-yl)acetamide

[Chem. 70]

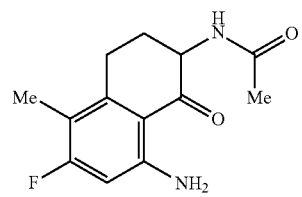

(11)

A suspension of N,N'-(3-fluoro-4-methyl-8-oxo-5,6,7,8-tetrahydronaphthalen-1,7-diyl)diacetamide (3.0 g, 10.3 mmol) in 2N hydrochloric acid/ethanol (30 mL) was stirred at 50° C. for 7 hours. Water (45 mL) was added to the resulting reaction solution, and the mixture was cooled to 1° C. After triethylamine (8.6 mL, 61.6 mmol) at 1° C. was added dropwise, sodium sulfite (26 mg, 0.2 mmol) was added. After the mixture was stirred at 1° C. for 4 hours, the precipitated crystals were collected by filtration and washed with cold 60% aqueous ethanol (30 mL) and water (15 mL). The resulting crystals were dried under reduced pressure to obtain pale green crystals (2.4 g). A suspension of the obtained pale green crystals (1.8 g) in acetone (18 mL) was stirred at 50° C. for 5 hours and then cooled to room temperature. The precipitated crystals were collected by filtration and washed with acetone (9 mL). The resulting crystals were dried at 40° C. under reduced pressure to give N-(8-amino-6-fluoro-5-methyl-1-oxo-1,2,3,4-tetrahydronaphthalen-2-yl)acetamide as pale green crystals (1.6 g, yield 82%).

$^1$H-NMR (400 MHz, DMSO-$d_6$) δ 8.07 (1H, d, J=8.0 Hz), 7.40 (2H, brs), 6.38 (1H, d, J=13.2 Hz), 4.52-4.43 (1H, m), 2.98-2.88 (1H, m), 2.87-2.76 (1H, m), 2.18-2.10 (1H, m), 1.98 (3H, d, J=1.2 Hz), 1.90 (3H, s), 1.88-1.78 (1H, m)

Example 5-2

N-(8-Amino-6-fluoro-5-methyl-1-oxo-1,2,3,4-tetrahydronaphthalen-2-yl)acetamide

[Chem. 71]

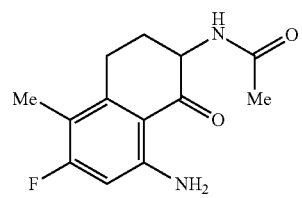

(11)

N,N'-(3-Fluoro-4-methyl-8-oxo-5,6,7,8-tetrahydronaphthalen-1,7-diyl)diacetamide (5.0 g, 17.1 mmol) was added in 5 divided portions to 2N hydrochloric acid/ethanol (75 mL) at room temperature, and the mixture was stirred at 50° C. for 5 hours. Water (113 mL) was added to the resulting reaction solution, and the mixture was cooled to 2° C. After triethylamine (22.5 mL, 161.4 mmol) was added dropwise at 2° C., sodium sulfite (43 mg, 0.3 mmol) was added. After the mixture was stirred at 2° C. for 3 hours, the precipitated crystals were collected by filtration and washed with cold 60% aqueous ethanol (50 mL) and water (25 mL). The resulting crystals were dried under reduced pressure to obtain pale blue crystals (3.9 g). A suspension of the obtained crystals (1.8 g) in acetone (18 mL) was stirred at 50° C. for 5 hours and then cooled to room temperature. The precipitated crystals were collected by filtration and washed with acetone (9 mL). The resulting crystals were dried at 40° C. under reduced pressure to give N-(8-amino-6-fluoro-5-methyl-1-oxo-1,2,3,4-tetrahydronaphthalen-2-yl)acetamide as pale green crystals (1.6 g, yield 80%).

$^1$H-NMR (400 MHz, DMSO-d$_6$) δ 8.07 (1H, d, J=8.0 Hz), 7.40 (2H, brs), 6.38 (1H, d, J=13.2 Hz), 4.52-4.43 (1H, m), 2.98-2.88 (1H, m), 2.87-2.76 (1H, m), 2.18-2.10 (1H, m), 1.98 (3H, d, J=1.2 Hz), 1.90 (3H, s), 1.88-1.78 (1H, m)

Example 6-1

N-[(9S)-9-Ethyl-5-fluoro-9-hydroxy-4-methyl-10, 13-dioxo-2,3,9,10,13,15-hexahydro-1H,12H-benzo[de]pyrano[3',4':6,7]indolizino[1,2-b]quinolin-1-yl]acetamide

[Chem. 72]

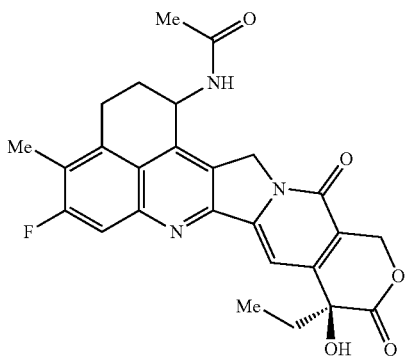

(12)

o-Cresol (510 mL) and pyridinium p-toluenesulfonate (25.6 g, 102 mmol) were added to a suspension of N-(8-amino-6-fluoro-5-methyl-1-oxo-1,2,3,4-tetrahydronaphthalen-2-yl)acetamide (170.0 g, 679 mmol) and (4S)-4-ethyl-4-hydroxy-7,8-dihydro-1H-pyrano[3,4-f]indolizin-3,6,10(4H)-trione (196.7 g, 747 mmol) in toluene (8.5 L), and the mixture was refluxed for 32 hours. Toluene (500 mL) was added, and the mixture was cooled to room temperature and stirred for 2 more hours. The precipitated crystals were filtered, and the crystals separated by filtration were washed with acetone (850 mL). The resulting crystals were dried at 40° C. under reduced pressure to give yellow crystals of N-[(9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide (312.5 g, yield 96%).

$^1$H-NMR (400 MHz, DMSO-d$_6$) δ 0.87 (3H, t, J=7.3 Hz), 1.79-1.88 (2H, m), 1.91 (3H, s), 2.13-2.15 (2H, m), 2.39 (3H, s), 3.13-3.22 (2H, m), 5.20 (2H, dd, J=25.6, 18.9 Hz), 5.42 (2H, s), 5.53-5.57 (1H, m), 6.52 (1H, s), 6.65-6.69 (0.4H, m), 6.75 (0.4H, d, J=7.9 Hz), 6.95-6.99 (0.4H, m), 7.03 (0.4H, d, J=7.3 Hz), 7.13-7.27 (0.4H, m). 7.30 (1H, s), 7.79 (1H, d, J=11.0 Hz), 8.46 (1H, d, J=9.2 Hz), 9.19 (0.4H, s).

$^{13}$C-NMR (100 MHz, DMSO-d$_6$) δ 7.7, 10.9, 10.9, 15.9, 22.6, 23.1, 27.7, 30.3, 44.0, 49.5, 65.2, 72.3, 96.6, 109.7, 109.9, 114.5, 118.7, 119.1, 121.4, 123.6, 123.7, 123.7, 125.3, 125.5, 126.6, 128.2, 128.9, 130.5, 136.2, 136.3, 140.4, 145.2, 147.8, 147.9, 149.9, 152.3, 155.3, 156.6, 160.3, 162.8, 169.1, 172.4.

MS (ESI) (m/z): 478 ([M+H]$^+$).

Example 6-2

N-[(9S)-9-Ethyl-5-fluoro-9-hydroxy-4-methyl-10, 13-dioxo-2,3,9,10,13,15-hexahydro-1H,12H-benzo[de]pyrano[3',4':6,7]indolizino[1,2-b]quinolin-1-yl]acetamide

[Chem. 73]

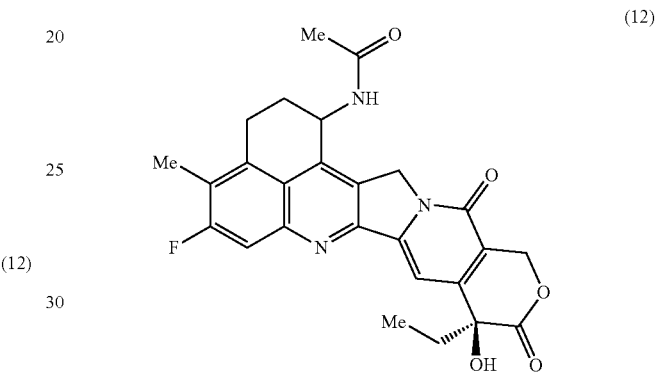

(12)

o-Cresol (7.5 mL) and pyridinium p-toluenesulfonate (0.75 g, 3.00 mmol) were added to a suspension of N-(8-amino-6-fluoro-5-methyl-1-oxo-1,2,3,4-tetrahydronaphthalen-2-yl)acetamide (2.5 g, 9.99 mmol) and (4S)-4-ethyl-4-hydroxy-7,8-dihydro-1H-pyrano[3,4-f]indolizin-3,6,10(4H)-trione (3.42 g, 12.99 mmol) in toluene (125 mL), and the mixture was refluxed for 19 hours (it was confirmed that this step proceeded via a compound represented by formula (30) and a compound represented by formula (31) as reaction intermediates).

Compound represented by formula (30): N-[(2S)-8-{[(4S)-4-Ethyl-4-hydroxy-3,10-dioxo-3,4,8,10-tetrahydro-1H-pyrano[3,4-f]indolizin-6-yl]amino}-6-fluoro-5-methyl-1-oxo-1,2,3,4-tetrahydronaphthalen-2-yl]acetamide

[Chem. 74]

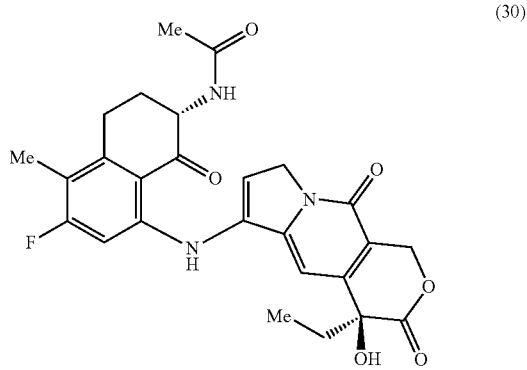

(30)

¹H-NMR (500 MHz, CDCl₃) δ 1.04 (3H, t, J=7.5 Hz), 1.80-1.93 (2H, m), 2.02-2.18 (8H, m), 3.80-3.85 (1H, m), 4.62-4.68 (1H, m), 4.75-4.85 (m, 2H), 5.20-5.33 (m, 2H), 5.70 (1H, d, J=16.0 Hz), 6.35 (1H, s), 6.67 (1H, d, J=5.5 Hz), 6.88 (1H, s), 6.99 (1H, d, J=12.0 Hz), 11.14 (1H, s). MS (ESI) (m/z): 496.5 ([M+H]⁺).

Compound represented by formula (31): N-[(2R)-8-{[(4S)-4-Ethyl-4-hydroxy-3,10-dioxo-3,4,8,10-tetrahydro-1H-pyrano[3,4-f]indolizin-6-yl]amino}-6-fluoro-5-methyl-1-oxo-1,2,3,4-tetrahydronaphthalen-2-yl]acetamide

[Chem. 75]

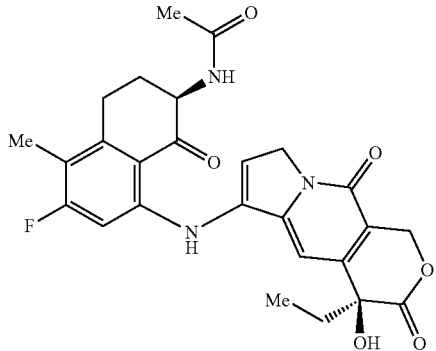

¹H-NMR (500 MHz, CDCl₃) δ 1.03 (3H, t, J=7.5 Hz), 1.80-1.92 (2H, m), 2.02-2.18 (8H, m), 3.79 (1H, s), 4.60-4.68 (1H, m), 4.72-4.87 (m, 2H), 5.28 (1H, d, J=16.0 Hz), 5.70 (1H, d, J=16.0 Hz), 6.35 (1H, s), 6.68 (1H, d, J=4.5 Hz), 6.88 (1H, s), 7.00 (1H, d, J=12.0 Hz), 11.10 (1H, s). MS (ESI) (m/z): 496.6 ([M+H]⁺).

After cooling, the liquid volume was regulated to 135 mL with toluene, and the mixture was stirred for 2 more hours. The precipitated crystals were filtered, and the crystals separated by filtration were washed with acetone (12.5 mL). The resulting crystals were dried at 40° C. under reduced pressure to give yellow crystals of N-[(9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide (4.58 g, yield 96%).

The apparatus data was the same as that of the compound described in Example 6-1.

Example 7-1

(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate dihydrate

[Chem. 76]

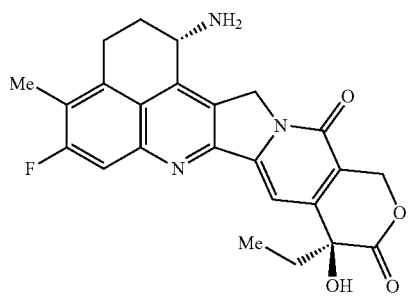

Methanesulfonic acid (1.5 L) was added to a suspension of N-[(9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide (300.0 g, 628 mmol) in 2-methoxyethanol (1.5 L), water (4.5 L), and ethylcyclohexane (1.5 L), and the mixture was refluxed for 8 hours. After the mixture was cooled to room temperature and separated to remove the organic layer, the removed organic layer was concentrated to 3 L under reduced pressure. The concentrate was heated to 40° C., and methanol (6 L) was added dropwise over 30 minutes. After the mixture was stirred for 2 hours, the precipitated crystals were filtered, and the crystals separated by filtration were washed with methanol (1.5 L).

The resulting crystals were dissolved in water (1.2 L), methanol (600 mL), and methanesulfonic acid (1.2 L), activated carbon (15 g) was added, and the mixture was stirred for 30 minutes. After cellulose powder (150 g) was added, and the mixture was stirred for 30 minutes, insoluble matter was separated by filtration and washed with a 50% methanesulfonic acid solution (600 mL) and methanol (600 mL). The filtrate was heated to 40° C., and methanol (4.8 L) was added dropwise over 55 minutes. After the mixture was stirred for 2 hours, the precipitated crystals were filtered, and the crystals separated by filtration were washed with methanol (1.5 L).

The resulting crystals were suspended in ethanol (6 L) and water (600 mL), and the mixture was refluxed for 1.5 hours. After the mixture was cooled to room temperature and stirred for 30 minutes, the precipitated crystals were filtered and washed with ethanol (1.5 L). The resulting crystals were dried at 40° C. under reduced pressure and then humidified for 4 days in air having 40% RH to give colorless crystals of (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate dihydrate (152.3 g, yield 43%).

¹H-NMR (400 MHz, DMSO-d₆, D₂O) δ 0.89 (3H, t, J=7.3 Hz), 1.90 (2H, q, J=7.3 Hz), 2.35 (3H, s), 2.38-2.47 (1H, m), 2.64 (3H, s), 3.04-3.11 (1H, m), 3.30-3.34 (1H, m), 5.08 (1H, s), 5.34 (2H, dd, J=17.7, 15.9 Hz), 5.50 (2H, dd, J=17.7, 10.4 Hz), 7.41 (1H, s), 7.59 (1H, d, J=11.0 Hz).

¹³C-NMR (125 MHz, DMSO-d₆) δ 7.7, 10.9, 11.0, 18.5, 20.8, 24.7, 30.2, 39.5, 44.5, 49.4, 55.9, 65.2, 72.2, 95.3, 96.9, 110.1, 100.3, 119.4, 120.5, 124.6, 124.7, 127.5, 134.2, 135.2, 135.2, 144.8, 147.8, 147.9, 149.9, 152.3, 156.6, 160.6, 162.6, 172.3.

MS (ESI) (m/z): 436 ([M+H]⁺).

Example 7-2

(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate

[Chem. 77]

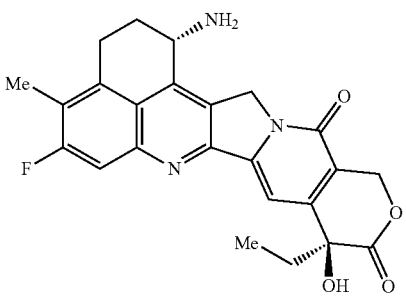

Methanesulfonic acid (18 mL) was added to a suspension of N-[(9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide (3.5 g, 7.3 mmol) in purified water (53 mL), 2-methoxyethanol (18 mL), and ethylcyclohexane (18 mL), and then the atmosphere of the mixture was repeatedly replaced with nitrogen under reduced pressure 3 times (the operation of performing stirring under reduced pressure at 50 mbar and then nitrogen replacement under normal pressure was repeated 3 times). The suspension was heated to 85° C. and then stirred for 11 hours, and cooled to 25° C. after confirming the completion of the reaction. The mixture was concentrated under reduced pressure to 38.5 mL, the concentrate was heated to 40° C., and methanol (18 mL) was added dropwise over 15 minutes. After the mixture was stirred for 6 hours, methanol (53 mL) was added dropwise over 2 hours, and after the mixture was stirred for 2 more hours, the precipitated crystals were filtered, and the crystals separated by filtration were washed with methanol (35 mL).

The resulting crystals were dissolved in a mixed solution of purified water (14 mL) and methanesulfonic acid (14 mL), the mixture was heated to 37° C., then methanol (7 mL), activated carbon (0.35 g), and a filter aid (0.70 g, diatomaceous earth: Celpure C 1000) were added, and nitrogen replacement of the atmosphere under reduced pressure was repeated 3 times (3 times of 50 mbar and normal-pressure nitrogen replacement). After the suspension was stirred for 20 minutes, insoluble matter was separated by filtration and washed with a mixed solution of methanesulfonic acid, purified water, and methanol (7 mL, 7 mL, 3.5 mL) and methanol (7 mL). The filtrate was heated to 37° C., and methanol (10.5 mL) was added dropwise over 15 minutes. After the mixture was stirred for 6 hours, methanol (42 mL) was added dropwise over 1 hour, and after the mixture was stirred for 2 more hours, the precipitated crystals were filtered, and the crystals separated by filtration were washed with methanol (35 mL).

The resulting crystals were suspended in ethanol (70 mL) and water (7 mL) and stirred at 73° C. for 2 hours. After the suspension was cooled to 25° C. and stirred for 2 hours, the precipitated crystals were filtered and washed with ethanol (18 mL). The resulting crystals were dried at 40° C. under reduced pressure to give (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate (1.72 g, yield 44%).

The apparatus data was the same as that of the compound described in Example 7-1.

Example 8

N-(3-Iodo-5-fluoro-4-methylphenyl)acetamide

[Chem. 78]

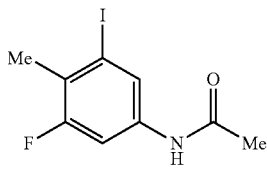

(34)

A solution of 2-fluoro-1-methyl-4-nitrobenzene (5.0 g, 32.3 mmol) in concentrated sulfuric acid (90% or more, 25 mL) and heptane (25 mL) was cooled to about 1° C., and then N-iodosuccinimide (10.2 g, 45.1 mmol) was added in six divided portions. The mixture was stirred at about 2° C. for 2 hours. The resulting reaction solution was added to cold water (25 mL). After toluene (25 mL) was added for separation, the aqueous layer was removed. Then, the organic layer was washed with water (25 mL), a 6.5 wt % aqueous sodium hydrogencarbonate solution (25 mL), a 5 wt % aqueous sodium sulfite solution (25 mL, 3 times), and finally water (25 mL). After the aqueous layer was removed from the filtrate, the organic layer was concentrated under reduced pressure. Ethyl acetate (50 mL) was added to the concentrated residue (about 30 mL), and the mixture was concentrated again under reduced pressure to give a solution of 1-iodo-3-fluoro-2-methyl-5-nitrobenzene in ethyl acetate (about 15 mL).

A suspension was obtained by adding a 1% platinum carbon catalyst (1.1 g) and ethyl acetate (45 mL) to the solution of 1-iodo-3-fluoro-2-methyl-5-nitrobenzene in ethyl acetate (about 15 mL) and the atmosphere was replaced with nitrogen and then replaced with hydrogen. The suspension was stirred at about 60° C. for 5 hours in a hydrogen stream (0.1 MPa) and cooled to room temperature. Insoluble matter was separated by filtration from the resulting suspension and washed with ethyl acetate (15 mL). The filtrate was washed twice with a 0.5N hydrochloric acid solution (50 mL, 25 mL) to obtain an organic layer. The aqueous layer at this time was extracted with ethyl acetate (25 mL) to obtain an organic layer, and the organic layers were combined. Then, the organic layer was washed with a 6.5 wt % aqueous sodium hydrogencarbonate solution (25 mL) and 5 wt % brine (25 mL), and the resulting organic layer was concentrated under reduced pressure to give a solution of 3-iodo-5-fluoro-4-methylaniline in ethyl acetate.

Triethylamine (3.7 mL, 26.8 mmol) and acetic anhydride (1.7 mL, 17.7 mmol) were added to a solution obtained by adding ethyl acetate (25 mL) to the solution of 3-bromo-5-fluoro-4-methylaniline in ethyl acetate (25 mL), and the mixture was stirred at room temperature for 4 hours. After 10 wt % brine (25 mL) was added to the resulting reaction solution for separation, the aqueous layer was removed. The resulting organic layer was concentrated under reduced pressure. Ethyl acetate (50 mL) was added to the concentrated residue, a 4N hydrochloric acid/ethyl acetate solution (5.6 mL, 22.6 mmol) was added, and then the mixture was stirred at room temperature for 15 minutes. Insoluble matter was separated by filtration and washed with ethyl acetate (20 mL). After 10 wt % brine (20 mL) was added to the filtrate, a 25 w/v % aqueous sodium hydroxide solution (2.5 mL) was added to regulate the pH to about 7. After the aqueous layer was removed, the organic layer was concentrated under reduced pressure. Acetonitrile (38 mL) and water (38 mL) were added to the concentrated residue, and the concentrated residue was stirred at 25° C. The precipitated crystals were collected by filtration and washed with 50% aqueous acetonitrile (15 mL). The resulting crystals were dried at 40° C. under reduced pressure to give N-(3-iodo-5-fluoro-4-methylphenyl)acetamide as white crystals (2.8 g, yield 29%).

$^1$H-NMR (500 MHz, CDCl$_3$) δ 7.61 (1H, s), 7.47 (1H, d, J=10.8 Hz), 7.10 (1H, brs), 2.30 (3H, d, J=2.3 Hz), 2.16 (3H, s)

Example 9

4-[5-(Acetylamino)-3-fluoro-2-methylphenyl]butanoic acid

[Chem. 79]

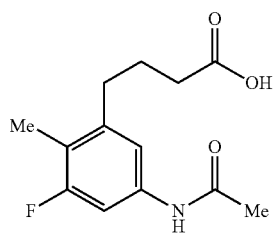

(8)

A solution of N-(3-iodo-5-fluoro-4-methylphenyl)acetamide (2.0 g, 6.8 mmol), 3-butenoic acid (0.7 mL, 8.2 mmol), and diisopropylethylamine (2.6 mL, 15.0 mmol) in tetrahydrofuran (8 mL) and water (2 mL) was degassed under reduced pressure and the atmosphere was replaced with nitrogen, and then tri(o-tolyl)phosphine (62.3 mg, 0.2 mmol) was added. Again the mixture was degassed under reduced pressure and the atmosphere was replaced with nitrogen, then palladium(II) acetate (23.0 mg, 0.1 mmol) was added, and the mixture was degassed under reduced pressure, the atmosphere replaced with nitrogen, and then thermally refluxed for 2 hours. Activated carbon (0.2 g), 2-methyltetrahydrofuran (10 mL), and water (10 mL) were added to the reaction solution that had been cooled to room temperature, and the mixture was stirred at room temperature for 1 hour. Insoluble matter was separated by filtration and washed with 20% aqueous tetrahydrofuran (4 mL). 2-Methyltetrahydrofuran (10 mL) and water (10 mL) were added to the filtrate, and a 25 w/v % aqueous sodium hydroxide solution (1.3 mL, 8.2 mmol) was added. The organic layer was removed, 2-methyltetrahydrofuran (20 mL) and concentrated hydrochloric acid (36%, 1.2 g, 12.3 mmol) were added to the aqueous layer, and then sodium chloride (2 g) was added. After separation, the aqueous layer was removed, and the organic layer was washed with 10 wt % brine (6 mL). The resulting organic layer was concentrated under reduced pressure to give 4-[5-(acetylamino)-3-fluoro-2-methylphenyl]-3-butenoic acid residue containing geometric isomers (1.9 g).

A suspension was obtained by adding 2-methyltetrahydrofuran (30 mL) and 5% palladium carbon (1.7 g) to the 4-[5-(acetylamino)-3-fluoro-2-methylphenyl]-3-butenoic acid residue containing geometric isomers (1.9 g) and the atmosphere was replaced with nitrogen, and then replaced with hydrogen. The mixture was stirred at about 40° C. for 8 hours in a hydrogen stream (0.3 MPa) and cooled to room temperature. Insoluble matter was separated by filtration from the resulting suspension and washed with 2-methyltetrahydrofuran (8 mL). Water (10 mL) was added to the filtrate, and the pH was regulated to about 2 with a 1N hydrochloric acid solution. After separation, the aqueous layer was removed, and the resulting organic layer was concentrated under reduced pressure. Ethyl acetate (10 mL) was added to the concentrated residue, the mixture was heated to about 50° C., then heptane (10 mL) was added, and the mixture was cooled to room temperature. The precipitated crystals were collected by filtration and washed with ethyl acetate/heptane (3/7) (6 mL). The resulting crystals were dried under reduced pressure to give 4-[5-(acetylamino)-3-fluoro-2-methylphenyl]butanoic acid as white crystals (1.4 g, yield 81%).

Example 10

N-(3-Fluoro-4-methyl-8-oxo-5,6,7,8-tetrahydronaphthalen-1-yl)acetamide

[Chem. 80]

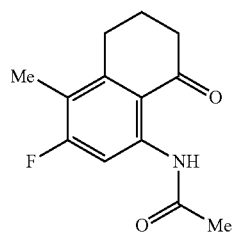

(9)

Aluminium chloride (263 mg, 1.97 mmol) was added to a solution of 4-[5-(acetylamino)-3-fluoro-2-methylphenyl]butanoic acid (200 mg, 0.79 mmol), thionyl chloride (86 µL, 1.18 mmol), and methylene chloride (4 mL) at room temperature under a nitrogen stream, and the mixture was stirred at room temperature for 2 hours. A 1N aqueous hydrochloric acid solution (10 ml) and ethyl acetate (50 ml) were added to the resulting reaction solution. The aqueous layer was removed, the organic layer was washed with water (10 ml), a 6.5 wt % aqueous sodium hydrogencarbonate solution (10 ml), and water (10 ml), and the resulting organic layer was dried over sodium sulfate. Insoluble matter was separated by filtration, the solvent was distilled off under reduced pressure, and the resulting residue was purified by preparative thin layer chromatography (hexane:ethyl acetate=2:1) to give N-(3-fluoro-4-methyl-8-oxo-5,6,7,8-tetrahydronaphthalen-1-yl)acetamide as pale yellowish white crystals (125 mg, yield 67%).

The apparatus data was the same as that of the compound described in Example 3-1.

FREE TEXT OF SEQUENCE LISTING

SEQ ID NO: 1—Amino acid sequence of a heavy chain of the anti-HER2 antibody
SEQ ID NO: 2—Amino acid sequence of a light chain of the anti-HER2 antibody
SEQ ID NO: 3—Amino acid sequence of a heavy chain of the anti-HER3 antibody
SEQ ID NO: 4—Amino acid sequence of a light chain of the anti-HER3 antibody
SEQ ID NO: 5—Amino acid sequence of a heavy chain of the anti-TROP2 antibody
SEQ ID NO: 6—Amino acid sequence of a light chain of the anti-TROP2 antibody
SEQ ID NO: 7—Amino acid sequence of a heavy chain of the anti-B7-H3 antibody
SEQ ID NO: 8—Amino acid sequence of a light chain of the anti-B7-H3 antibody
SEQ ID NO: 9—Amino acid sequence of a heavy chain of the anti-GPR20 antibody
SEQ ID NO: 10—Amino acid sequence of a light chain of the anti-GPR20 antibody

The invention claimed is:

1. A method for producing a compound represented by formula (C):

[Chem. 2]

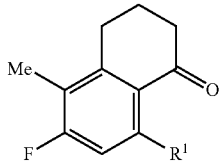

(C)

wherein $R^1$ represents an amino group protected with a protecting group,
the method comprising a step of subjecting a compound represented by formula (B):

[Chem. 1]

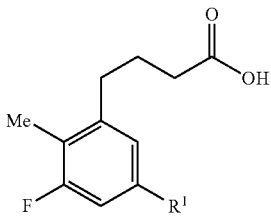

(B)

wherein $R^1$ represents the same meaning as above, to intramolecular cyclization to convert the compound represented by formula (B) into the compound represented by formula (C).

2. The production method according to claim 1, wherein $R^1$ is an amino group protected with an acetyl group, a methoxyacetyl group, a trifluoroacetyl group, a trichloroacetyl group, a pivaloyl group, a formyl group, or a benzoyl group.

3. The production method according to claim 1, wherein R¹ is an amino group protected with an acetyl group or a trifluoroacetyl group.

4. The production method according to claim 1, wherein R¹ is an amino group protected with an acetyl group.

5. The production method according to claim 1, wherein the intramolecular cyclization is performed by a method comprising reacting the compound represented by formula (B) with trifluoroacetic anhydride.

6. The production method according to claim 5, wherein the intramolecular cyclization is performed in a solvent comprising trifluoroacetic acid.

7. The production method according to claim 1, wherein the intramolecular cyclization is performed by a method comprising reacting the compound represented by formula (B) with thionyl chloride.

8. The production method according to claim 7, wherein the intramolecular cyclization is performed in the presence of aluminium chloride.

9. A method for producing a compound represented by formula (C):

[Chem. 4]

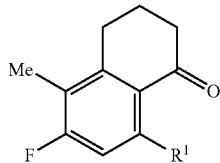

wherein R¹ represents an amino group protected with a protecting group,
the method comprising a step of subjecting a compound represented by formula (J):

[Chem. 3]

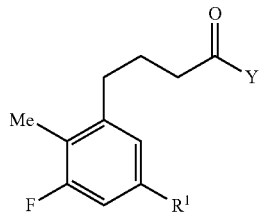

wherein Y represents a leaving group, and R¹ represents the same meaning as above, to intramolecular cyclization to convert the compound represented by formula (J) into the compound represented by formula (C).

10. The production method according to claim 9, wherein R¹ is an amino group protected with an acetyl group, a methoxyacetyl group, a trifluoroacetyl group, a trichloroacetyl group, a pivaloyl group, a formyl group, or a benzoyl group.

11. The production method according to claim 9, wherein R¹ is an amino group protected with an acetyl group or a trifluoroacetyl group.

12. The production method according to claim 9, wherein R¹ is an amino group protected with an acetyl group.

13. The production method according to claim 9, wherein Y is a chloro group.

14. The production method according to claim 9, wherein Y is a trifluoroacetoxy group.

15. The production method according to claim 13, wherein the intramolecular cyclization is performed in the presence of aluminium chloride.

16. The production method according to claim 14, wherein the intramolecular cyclization is performed in a solvent comprising trifluoroacetic acid.

17. A method for producing a compound represented by formula (C):

[Chem. 8]

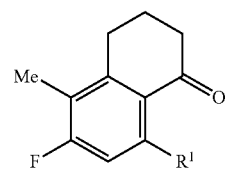

wherein R¹ represents an amino group protected with a protecting group,
the method comprising the steps of:
coupling a compound represented by formula (D):

[Chem. 5]

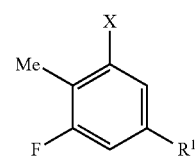

wherein X represents a leaving group, and R¹ represents the same meaning as above, with 3-butenoic acid to convert the compound represented by formula (D) into a compound represented by formula (E):

[Chem. 6]

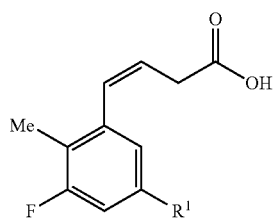

wherein R¹ represents the same meaning as above; then
reducing the compound represented by formula (E) to convert the compound represented by formula (E) into a compound represented by formula (B):

[Chem. 7]

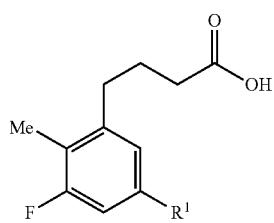
(B)

wherein R¹ represents the same meaning as above; and then subjecting the compound represented by formula (B) to intramolecular cyclization to convert the compound represented by formula (B) into the compound represented by formula (C).

18. The production method according to claim 17, wherein X is a bromo group, an iodo group, a trifluoromethanesulfonyloxy group, or an arylsulfonyloxy group.

19. The production method according to claim 17, wherein X is a bromo group.

20. The production method according to claim 17, wherein X is an iodo group.

21. The production method according to claim 17, wherein R¹ is an amino group protected with an acetyl group, a methoxyacetyl group, a trifluoroacetyl group, a trichloroacetyl group, a pivaloyl group, a formyl group, or a benzoyl group.

22. The production method according to claim 17, wherein R¹ is an amino group protected with an acetyl group or a trifluoroacetyl group.

23. The production method according to claim 17, wherein R¹ is an amino group protected with an acetyl group.

24. The production method according to claim 17, wherein the step of coupling the compound represented by formula (D) with 3-butenoic acid to convert the compound represented by formula (D) into the compound represented by formula (E) is performed in the presence of a palladium complex prepared from palladium(II) acetate and tri(o-tolyl)phosphine.

25. The production method according to claim 17, comprising the steps of: dissolving the compound represented by formula (E) in a basic aqueous solution to wash the compound represented by formula (E) with a first organic solvent and separating the solvents; and then adding an acid to the basic aqueous solution to extract the compound represented by formula (E) with a second organic solvent and separating the solvents.

26. The production method according to claim 25, wherein the first organic solvent is 2-methyltetrahydrofuran.

27. The production method according to claim 25, wherein the second organic solvent is 2-methyltetrahydrofuran.

28. The production method according to claim 25, wherein the basic aqueous solution is an aqueous sodium hydroxide solution.

29. The production method according to claim 17, wherein the step of reducing the compound represented by formula (E) to convert the compound represented by formula (E) into the compound represented by formula (B) is performed by a method comprising reacting the compound represented by formula (E) with hydrogen in a solvent in the presence of a palladium carbon catalyst.

30. The production method according to claim 17, wherein the step of subjecting the compound represented by formula (B) to intramolecular cyclization to convert the compound represented by formula (B) into the compound represented by formula (C) is performed by a method comprising reacting the compound represented by formula (B) with trifluoroacetic anhydride.

31. The production method according to claim 30, wherein the intramolecular cyclization is performed in a solvent comprising trifluoroacetic acid.

32. The production method according to claim 17, wherein the step of subjecting the compound represented by formula (B) to intramolecular cyclization to convert the compound represented by formula (B) into the compound represented by formula (C) is performed by a method comprising reacting the compound represented by formula (B) with thionyl chloride.

33. The production method according to claim 32, wherein the intramolecular cyclization is performed in the presence of aluminium chloride.

34. A method for producing a compound represented by formula (2):

[Chem. 14]

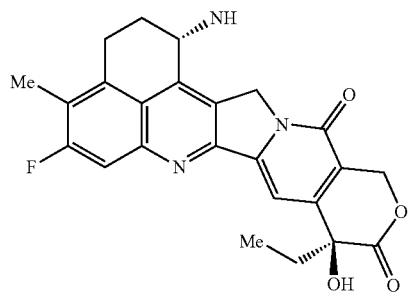
(2)

wherein a compound represented by formula (C):

[Chem. 9]

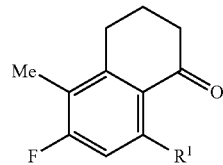
(C)

produced by the method according to claim 1 is used as a starting material, the method comprising the steps of:
converting the compound represented by formula (C) into a compound represented by formula (F):

[Chem. 10]

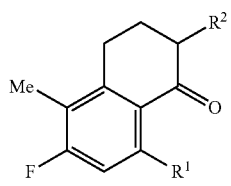
(F)

wherein R¹ represents the same meaning as defined in claim 1, and R² represents an amino group protected with a protecting group; then
converting the compound represented by formula (F) into a compound represented by formula (G):

[Chem. 11]

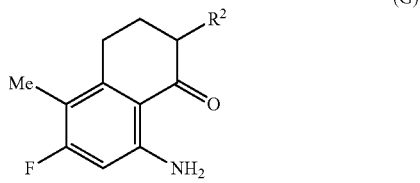
(G)

wherein R² represents the same meaning as above; then condensing the compound represented by formula (G) with a compound represented by formula (1):

[Chem. 12]

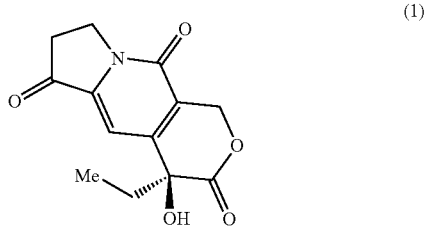
(1)

to convert the compound represented by formula (G) into a compound represented by formula (H):

[Chem. 13]

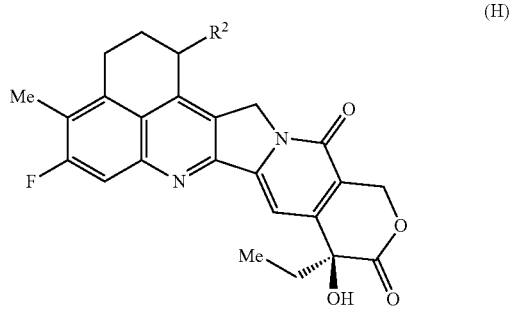
(H)

wherein R² represents the same meaning as above; and then
converting the compound represented by formula (H) into the compound represented by formula (2).

35. The production method according to claim 34, wherein R² is an amino group protected with an acetyl group, a methoxyacetyl group, a trifluoroacetyl group, a trichloroacetyl group, a pivaloyl group, a formyl group, or a benzoyl group.

36. The production method according to claim 34, wherein R² is an amino group protected with an acetyl group or a trifluoroacetyl group.

37. The production method according to claim 34, wherein R² is an amino group protected with an acetyl group.

38. The production method according to claim 34, wherein the step of converting the compound represented by formula (C) into the compound represented by formula (F) comprises the sub-steps of: (i) reacting the compound represented by formula (C) with a nitrous acid ester in the presence of a base to introduce a nitroso group; (ii) introducing a protecting group to a nitrogen atom derived from the nitroso group; and (iii) reducing the compound represented by formula (C) with hydrogen in the presence of a platinum carbon catalyst.

39. The production method according to claim 34, wherein the step of converting the compound represented by formula (F) into the compound represented by formula (G) is performed in a solvent comprising hydrochloric acid/ethanol.

40. The production method according to claim 34, wherein the step of condensing the compound represented by formula (G) with the compound represented by formula (1) to convert the compound represented by formula (G) into the compound represented by formula (H) is performed in a solvent comprising o-cresol.

41. The production method according to claim 34, wherein the step of converting the compound represented by formula (H) into the compound represented by formula (2) is performed in a solvent comprising methanesulfonic acid.

42. The production method according to claim 34, wherein the compound represented by formula (2) is in the form of a methanesulfonic acid salt.

43. The production method according to claim 34, wherein the compound represented by formula (2) is in the form of a methanesulfonic acid salt m-hydrate wherein m is in a range of 0 to 3.

44. The production method according to claim 34, wherein the compound represented by formula (2) is in the form of a methanesulfonic acid salt dihydrate.

45. A method for producing a compound represented by formula (2):

[Chem. 26]

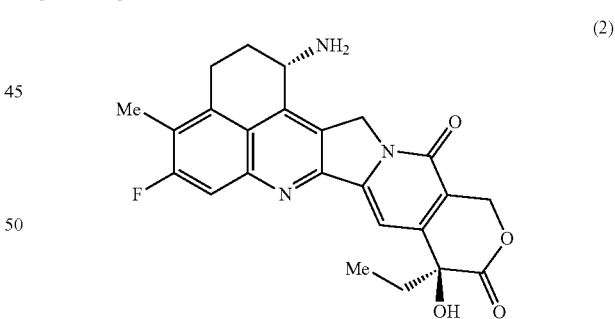
(2)

wherein the method comprises the steps of:
converting a compound represented by formula (3):

[Chem. 15]

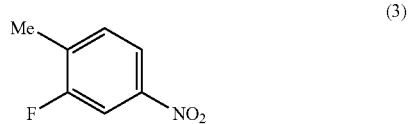
(3)

into a compound represented by formula (4):

[Chem. 16]

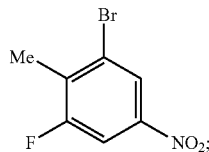
(4)

then
converting the compound represented by formula (4) into a compound represented by formula (5):

[Chem. 17]

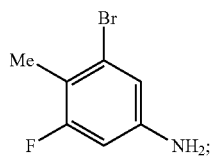
(5)

then
converting the compound represented by formula (5) into a compound represented by formula (6):

[Chem. 18]

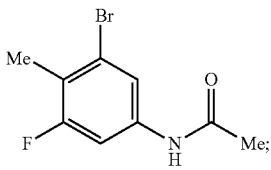
(6)

then
coupling the compound represented by formula (6) with 3-butenoic acid to convert the compound represented by formula (6) into a compound represented by formula (7):

[Chem. 19]

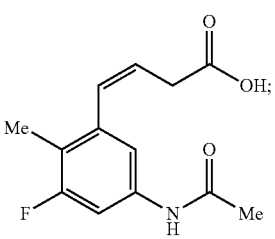
(7)

then
converting the compound represented by formula (7) into a compound represented by formula (8):

[Chem. 20]

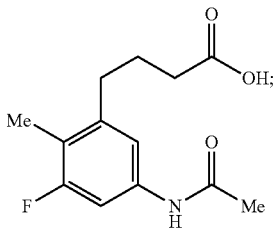
(8)

then
subjecting the compound represented by formula (8) to intramolecular cyclization to convert the compound represented by formula (8) into a compound represented by formula (9):

[Chem. 21]

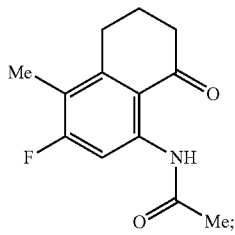
(9)

then
converting the compound represented by formula (9) into a compound represented by formula (10):

[Chem. 22]

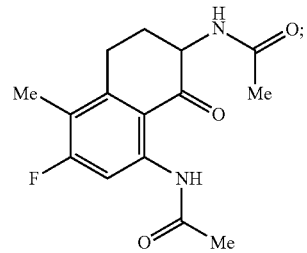
(10)

then
converting the compound represented by formula (10) into a compound represented by formula (11):

[Chem. 23]

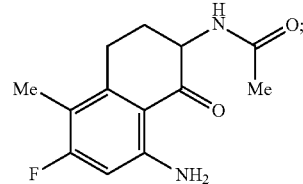
(11)

then
condensing the compound represented by formula (11) with a compound represented by formula (1):

[Chem. 24]

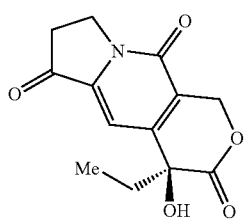
(1)

to convert the compound represented by formula (11) into a compound represented by formula (12):

[Chem. 25]

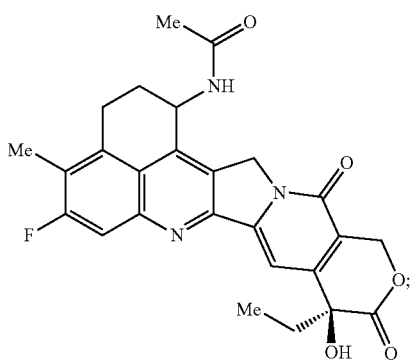
(12)

and then
converting the compound represented by formula (12) into the compound represented by formula (2).

46. The production method according to claim 45, wherein the step of coupling the compound represented by formula (6) with 3-butenoic acid to convert the compound represented by formula (6) into the compound represented by formula (7) is performed in the presence of a palladium complex prepared from palladium(II) acetate and tri(o-tolyl)phosphine.

47. The production method according to claim 45, comprising the steps of: dissolving the compound represented by formula (7) in a basic aqueous solution to wash the compound represented by formula (7) with a first organic solvent and separating the solvents; and then adding an acid to the basic aqueous solution to extract the compound represented by formula (7) with a second organic solvent and separating the solvents.

48. The production method according to claim 47, wherein the first organic solvent is 2-methyltetrahydrofuran.

49. The production method according to claim 47, wherein the second organic solvent is 2-methyltetrahydrofuran.

50. The production method according to claim 46, wherein the basic aqueous solution is an aqueous sodium hydroxide solution.

51. The production method according to claim 45, wherein the step of subjecting the compound represented by formula (8) to intramolecular cyclization to convert the compound represented by formula (8) into the compound represented by formula (9) is performed by a method comprising reacting the compound represented by formula (8) with trifluoroacetic anhydride.

52. The production method according to claim 51, wherein the intramolecular cyclization is performed in a solvent comprising trifluoroacetic acid.

53. The production method according to claim 45, wherein the step of converting the compound represented by formula (9) into the compound represented by formula (10) comprises the sub-steps of: (i) reacting the compound represented by formula (9) with a nitrous acid ester in the presence of a base to introduce a nitroso group; then (ii) introducing a protecting group to a nitrogen atom derived from the nitroso group; and (iii) reducing the compound represented by formula (9) with hydrogen in the presence of a platinum carbon catalyst.

54. The production method according to claim 45, wherein the step of converting the compound represented by formula (10) into the compound represented by formula (11) is performed in a solvent comprising hydrochloric acid/ethanol.

55. The production method according to claim 45, wherein the step of condensing the compound represented by formula (11) with the compound represented by formula (1) to convert the compound represented by formula (11) into the compound represented by formula (12) is performed in a solvent comprising o-cresol.

56. The production method according to claim 45, wherein the step of converting the compound represented by formula (12) into the compound represented by formula (2) is performed in a solvent comprising methanesulfonic acid.

57. The production method according to claim 45, wherein the compound represented by formula (2) is in the form of a methanesulfonic acid salt.

58. The production method according to claim 45, wherein the compound represented by formula (2) is in the form of a methanesulfonic acid salt m-hydrate wherein m is in a range of 0 to 3.

59. The production method according to claim 45, wherein the compound represented by formula (2) is in the form of a methanesulfonic acid salt dihydrate.

60. The production method according to claim 1, wherein no chromatography is used.

61. A compound represented by formula (7):

[Chem. 29]

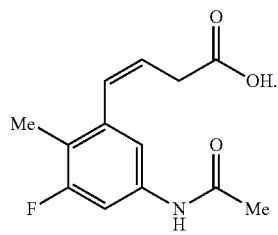
(7)

62. A compound represented by formula (8):

[Chem. 30]

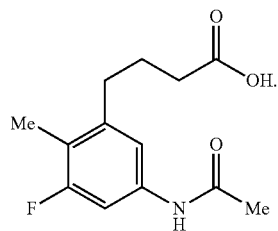
(8)

63. A method for producing a compound represented by formula (14):

[Chem. 33]

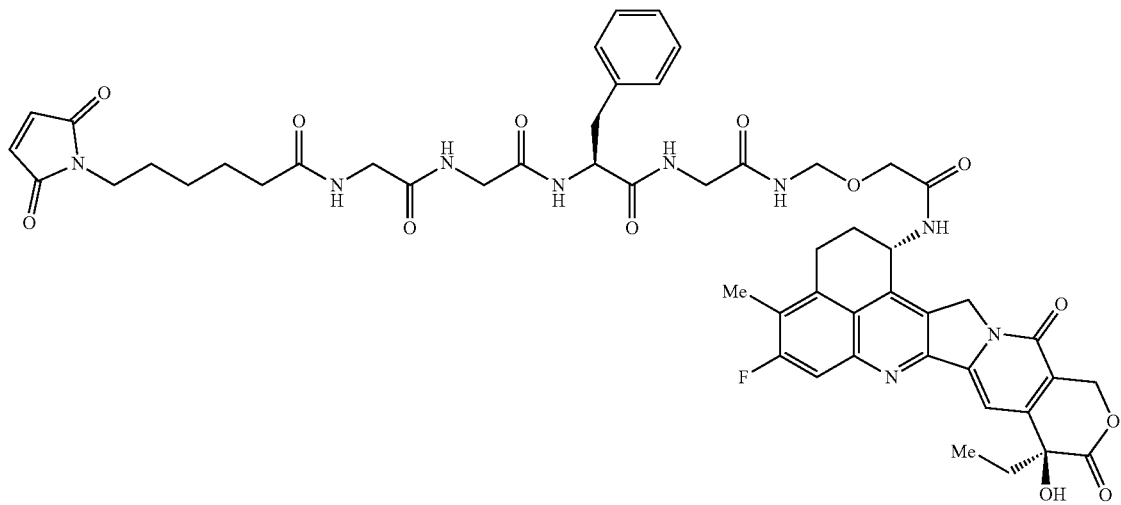
(14)

wherein a compound represented by formula (2):
[Chem. 31]

[Chem. 31]

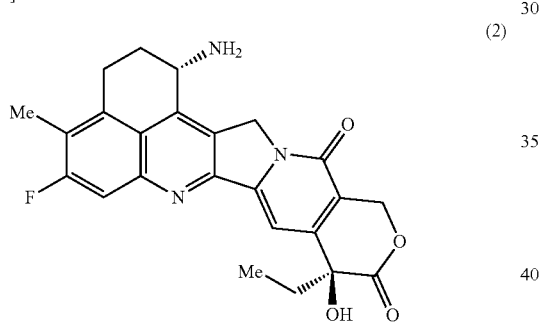
(2)

produced by the method according to claim 34 is used as a starting material, the method comprising the steps of:
condensing the compound represented by formula (2) with a compound represented by formula (13):

[Chem. 32]

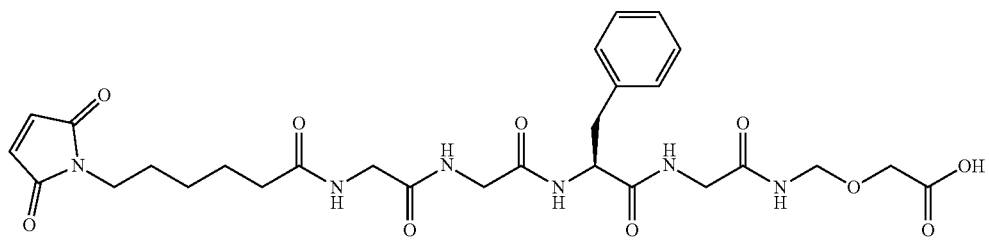
(13)

to convert the compound represented by formula (2) into the compound represented by formula (14).

64. A method for producing an antibody-drug conjugate, in which a drug-linker represented by formula (15):

[Chem. 35]

(15)

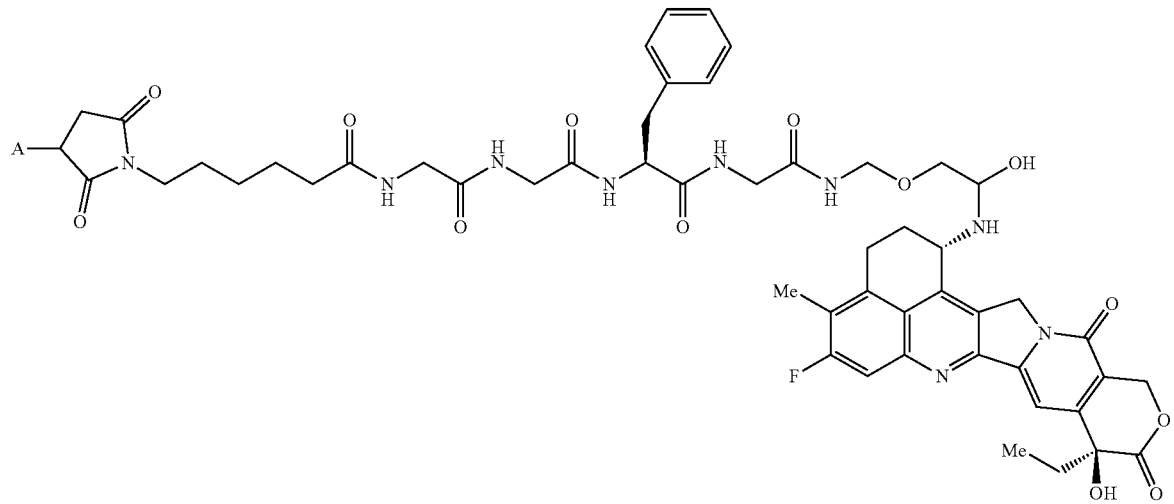

wherein A represents the connecting position to an antibody;
is conjugated to the antibody via a thioether bond,
wherein a compound represented by formula (14):

[Chem. 34]

(14)

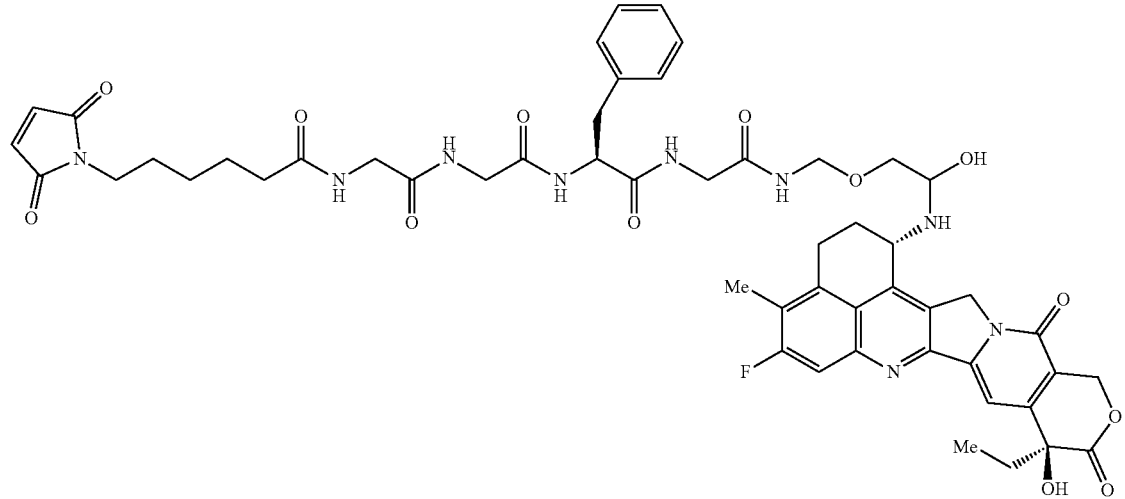

produced by the method according to claim 63 is used as a raw material,
the method comprising the steps of:
(i) reducing an antibody; and then
(ii) reacting the compound represented by formula (14) produced by the method with the reduced antibody.

65. The production method according to claim 64, wherein the antibody is an anti-HER2 antibody, an anti-HER3 antibody, an anti-TROP2 antibody, an anti-B7-H3 antibody, or an anti-GPR20 antibody.

\* \* \* \* \*

SEQUENCE LISTING

<160> NUMBER OF SEQ ID NOS: 10

<210> SEQ ID NO 1
<211> LENGTH: 450
<212> TYPE: PRT
<213> ORGANISM: Artificial Sequence
<220> FEATURE:
<223> OTHER INFORMATION: Heavy chain of anti-HER2 antibody

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Light chain of anti-HER2 antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 447
<212> TYPE: PRT
<213> ORGANISM: Artificial Sequence
<220> FEATURE:
<223> OTHER INFORMATION: Heavy chain of anti-HER3 antibody
```

<400> SEQUENCE: 3

| | | | | | | | | | | | | | | |
|---|---|---|---|---|---|---|---|---|---|---|---|---|---|---|
| Gln | Val | Gln | Leu | Gln | Gln | Trp | Gly | Ala | Gly | Leu | Leu | Lys | Pro | Ser | Glu |
| 1 | | | | 5 | | | | | 10 | | | | | 15 | |
| Thr | Leu | Ser | Leu | Thr | Cys | Ala | Val | Tyr | Gly | Gly | Ser | Phe | Ser | Gly | Tyr |
| | | | 20 | | | | | 25 | | | | | 30 | | |
| Tyr | Trp | Ser | Trp | Ile | Arg | Gln | Pro | Pro | Gly | Lys | Gly | Leu | Glu | Trp | Ile |
| | | 35 | | | | | 40 | | | | | 45 | | | |
| Gly | Glu | Ile | Asn | His | Ser | Gly | Ser | Thr | Asn | Tyr | Asn | Pro | Ser | Leu | Lys |
| 50 | | | | | 55 | | | | | 60 | | | | | |
| Ser | Arg | Val | Thr | Ile | Ser | Val | Glu | Thr | Ser | Lys | Asn | Gln | Phe | Ser | Leu |
| 65 | | | | 70 | | | | | 75 | | | | | 80 | |
| Lys | Leu | Ser | Ser | Val | Thr | Ala | Ala | Asp | Thr | Ala | Val | Tyr | Tyr | Cys | Ala |
| | | | | 85 | | | | | 90 | | | | | 95 | |
| Arg | Asp | Lys | Trp | Thr | Trp | Tyr | Phe | Asp | Leu | Trp | Gly | Arg | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| 130 | | | | | 135 | | | | | 140 | | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| 210 | | | | | 215 | | | | | 220 | | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| 290 | | | | | 295 | | | | | 300 | | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| 370 | | | | | 375 | | | | | 380 | | | | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |
| Asp | Gly | Ser | Phe | Phe | Leu | Tyr | Ser | Lys | Leu | Thr | Val | Asp | Lys | Ser | Arg |

405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 4
<211> LENGTH: 220
<212> TYPE: PRT
<213> ORGANISM: Artificial Sequence
<220> FEATURE:
<223> OTHER INFORMATION: Light chain of anti-HER3 antibody

<400> SEQUENCE: 4

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 5
<211> LENGTH: 470
<212> TYPE: PRT
<213> ORGANISM: Artificial Sequence
<220> FEATURE:
<223> OTHER INFORMATION: Heavy chain of anti-TROP2 antibody

<400> SEQUENCE: 5

Met Lys His Leu Trp Phe Phe Leu Leu Leu Val Ala Ala Pro Arg Trp
1               5                   10                  15

Val Leu Ser Gln Val Gln Leu Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

```
Thr Thr Ala Gly Met Gln Trp Val Arg Gln Ala Pro Gly Gln Gly Leu
 50                  55                  60

Glu Trp Met Gly Trp Ile Asn Thr His Ser Gly Val Pro Lys Tyr Ala
 65                  70                  75                  80

Glu Asp Phe Lys Gly Arg Val Thr Ile Ser Ala Asp Thr Ser Thr Ser
                 85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
            115                 120                 125

Val Trp Gly Gln Gly Thr Leu Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
```

```
                                         465                     470

<210> SEQ ID NO 6
<211> LENGTH: 234
<212> TYPE: PRT
<213> ORGANISM: Artificial Sequence
<220> FEATURE:
<223> OTHER INFORMATION: Light chain of anti-TROP2 antibody

<400> SEQUENCE: 6

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 7
<211> LENGTH: 471
<212> TYPE: PRT
<213> ORGANISM: Artificial Sequence
<220> FEATURE:
<223> OTHER INFORMATION: Heavy chain of anti-B7-H3 antibody

<400> SEQUENCE: 7

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Arg Gln Ala Pro Gly Gln Gly Leu
    50                  55                  60
```

```
Glu Trp Met Gly Tyr Ile Asn Pro Tyr Asn Asp Val Lys Tyr Asn
 65                  70                  75                  80

Glu Lys Phe Lys Gly Arg Val Thr Ile Thr Ala Asp Glu Ser Thr Ser
                 85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

```
<210> SEQ ID NO 8
<211> LENGTH: 233
<212> TYPE: PRT
<213> ORGANISM: Artificial Sequence
<220> FEATURE:
<223> OTHER INFORMATION: Light chain of anti-B7-H3 antibody

<400> SEQUENCE: 8

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 9
<211> LENGTH: 472
<212> TYPE: PRT
<213> ORGANISM: Artificial Sequence
<220> FEATURE:
<223> OTHER INFORMATION: Heavy chain of anti-GPR20 antibody

<400> SEQUENCE: 9

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Ile Ser Trp Ile Arg Gln Ala Pro Gly Gln Gly Leu
    50                  55                  60

Lys Tyr Met Gly Phe Ile Asn Pro Gly Ser Gly His Thr Asn Tyr Asn
65                  70                  75                  80
```

Glu Lys Phe Lys Gly Arg Val Thr Ile Thr Ala Asp Lys Ser Ser Ser
                    85                  90                  95

Thr Ala Thr Met Glu Leu Ser Ser Leu Arg Ser Glu Asp Thr Ala Val
            100                 105                 110

Tyr Tyr Cys Ala Arg Gly Ala Gly Gly Phe Leu Arg Ile Ile Thr Lys
            115                 120                 125

Phe Asp Tyr Trp Gly Gln Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
            210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 10
<211> LENGTH: 234
<212> TYPE: PRT

<213> ORGANISM: Artificial Sequence
<220> FEATURE:
<223> OTHER INFORMATION: Light chain of anti-GPR20 antibody

<400> SEQUENCE: 10

```
Met Val Leu Gln Thr Gln Val Phe Ile Ser Leu Leu Leu Trp Ile Ser
1               5                   10                  15

Gly Ala Tyr Gly Asp Thr Gln Leu Thr Gln Ser Pro Ser Ser Leu Ser
                20                  25                  30

Ala Ser Val Gly Asp Arg Val Thr Ile Thr Cys Arg Ala Ser Lys Ser
            35                  40                  45

Val Ser Thr Tyr Ile His Trp Tyr Gln Gln Lys Pro Gly Lys Gln Pro
    50                  55                  60

Lys Leu Leu Ile Tyr Ser Ala Gly Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Asn Tyr Tyr Cys Gln Gln Ile Asn
                100                 105                 110

Glu Leu Pro Tyr Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

UNITED STATES PATENT AND TRADEMARK OFFICE
CERTIFICATE OF CORRECTION

PATENT NO. : 11,318,212 B2
APPLICATION NO. : 16/642277
DATED : May 3, 2022
INVENTOR(S) : Yoshio Nishi et al.

Page 1 of 1

It is certified that error appears in the above-identified patent and that said Letters Patent is hereby corrected as shown below:

In the Claims

Claim 34, Column 102, Lines 24-37:
Please replace with:
[Chem. 14]

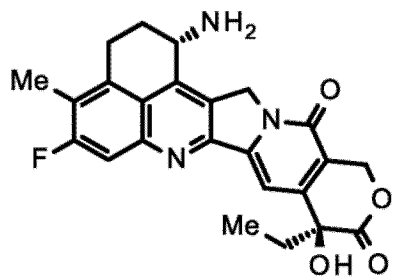

(2)

Signed and Sealed this
Twenty-seventh Day of December, 2022

Katherine Kelly Vidal
*Director of the United States Patent and Trademark Office*